(12) United States Patent
Dadachova et al.

(10) Patent No.: US 11,760,791 B2
(45) Date of Patent: Sep. 19, 2023

(54) MELANIN ANTIBODIES AND USES THEREOF

(71) Applicant: Radimmune Therapeutics, Inc., Tarrytown, NY (US)

(72) Inventors: Ekaterina Dadachova, Saskatoon (CA); David J. Rickles, Manhattan Beach, CA (US)

(73) Assignee: RADIMMUNE THERAPEUTICS, INC., Tarrytown, NY (US)

( * ) Notice: Subject to any disclaimer, the term of this patent is extended or adjusted under 35 U.S.C. 154(b) by 0 days.

(21) Appl. No.: 16/646,994

(22) PCT Filed: Sep. 13, 2018

(86) PCT No.: PCT/US2018/050955
§ 371 (c)(1),
(2) Date: Mar. 12, 2020

(87) PCT Pub. No.: WO2019/055706
PCT Pub. Date: Mar. 21, 2019

(65) Prior Publication Data
US 2020/0262896 A1 Aug. 20, 2020

Related U.S. Application Data

(60) Provisional application No. 62/558,230, filed on Sep. 13, 2017.

(51) Int. Cl.
| | |
|---|---|
| *C07K 16/18* | (2006.01) |
| *A61K 39/395* | (2006.01) |
| *A61P 35/00* | (2006.01) |
| *A61P 35/04* | (2006.01) |
| *C07K 16/28* | (2006.01) |
| *C07K 16/30* | (2006.01) |
| *A61K 9/00* | (2006.01) |
| *A61K 39/00* | (2006.01) |
| *C07K 19/00* | (2006.01) |

(52) U.S. Cl.
CPC ........ *C07K 16/18* (2013.01); *A61K 39/39558* (2013.01); *A61P 35/04* (2018.01); *C07K 16/2818* (2013.01); *C07K 16/2827* (2013.01); *C07K 16/3053* (2013.01); *A61K 9/0019* (2013.01); *A61K 39/00* (2013.01); *A61K 39/3955* (2013.01); *A61K 2039/505* (2013.01); *C07K 19/00* (2013.01); *C07K 2317/24* (2013.01); *C07K 2317/31* (2013.01); *C07K 2317/565* (2013.01); *C07K 2319/00* (2013.01)

(58) Field of Classification Search
CPC ................ C07K 16/18; C07K 2317/24; A61K 39/3955; A61P 35/00
See application file for complete search history.

(56) References Cited

U.S. PATENT DOCUMENTS

| | | | |
|---|---|---|---|
| 7,402,385 B2 | 7/2008 | Dadachova et al. | |
| 2004/0156780 A1 | 8/2004 | Dadachova et al. | |
| 2006/0039858 A1 | 2/2006 | Dadachova et al. | |
| 2011/0300067 A1 | 12/2011 | Dadachova et al. | |
| 2014/0308276 A1 | 10/2014 | Liu et al. | |
| 2015/0119555 A1 | 4/2015 | Jung et al. | |
| 2016/0108123 A1* | 4/2016 | Freeman ..........  | A61K 39/39558 |
| | | | 435/69.6 |

OTHER PUBLICATIONS

Mahoney et al., 2015. Clinical Therapeutics. 37(4): 764-782.*
Rudikoff et al (1982. Proc Natl Acad Sci USA. 79: 1979-1983).*
Almagro Juan C et al: "Humanization of antibodies", Frontiers in Bioscience, Frontiers in Bioscience, Albertson, NY, US, vol. 13, Jan. 1, 2008 (Jan. 1, 2008), pp. 1619-1633
Extended European Search Report dated Apr. 29, 2021, for EP Application No. 18 856 150.0, filed on Sep. 13, 2018, 10 pages.
Balch, C.M. et al. (2009). "Final version of 2009 AJCC melanoma staging and classification," J. Clin. Oncol. 27:6199- 6206.
Fellner, C. (2012). "Ipilimumab (yervoy) Prolongs Survival in Advanced Melanoma: Serious Side Effects and a Hefty Price Tag May Limit Its Use," Pharmacy &Therapeutics 37:503-511.
Dadachova, E. et al. (2004). "Dead cells in melanoma tumors provide abundant antigen for targeted delivery of ionizing radiation by a mAb to melanin," PNAS 101:14865-14870.
Dadachova, E. et al. (2008). "Pre-clinical development of a 188Re-labeled melanin-binding antibody for phase I clinical trial in patients with metastatic melanoma," J. Nucl. Med. vol. 49, Suppl. 1, 327P, 2 total pages.
Genbank accession No. AFX62601.1 (2012). Anti-human DCIR 9E8 immunoglobulin kappa light chain (synthetic construct), located at https://www.ncbi.nlm.nih.gov/protein/AFX62601.1, 2 total pages.
GenBank accession No. ADB20400.1 (2016). Chimeric anti-Burkholderia pseudomallei immunoglobulin heavy chain, partial (synthetic construct), located at https://www.ncbi.nlm.nih.gov/protein/ADB20400.1, 2 total pages.
GenBank accession No. KX346264.1 (2017). Synthetic construct clone 8C3 mAb sequence, 2 total pages.
Hodi, F.S. et al. (2010). "Improved survival with ipilimumab in patients with metastatic melanoma," N. Engl. J. Med. 363:711-723.
International Search Report dated Jan. 28, 2019, for PCT Application No. PCT/US2018/050955, filed on Sep. 13, 2018, 5 pages.
Jurcic, J.G. et al. (2002). "Targeted a particle immunotherapy for myeloid leukemia," Blood 100:1233-1239.
Kirschner, A.S. et al. (1975). "Radiation-dosimetry of 131I-19-iodocholesterol," J. Nucl. Med. 14:713-717.
Klein, M. et al. (2008). "Imaging of metastatic melanoma (MM) with a 188Rhenium (188Re)-labeled melanin binding antibody," J. Nucl. Med. vol. 49, Supplement 1, 52P, 2 total pages.

(Continued)

*Primary Examiner* — Zachary C Howard
(74) *Attorney, Agent, or Firm* — Cooley LLP

(57) ABSTRACT

Provided herein are monoclonal antibodies that specifically bind to melanin. The antibodies may be chimeric or humanized. Also provided herein are methods of use and methods of making the antibodies described. For example, the melanin antibodies may be used therapeutically to treat or prevent melanoma.

21 Claims, 38 Drawing Sheets

Specification includes a Sequence Listing.

(56) References Cited

OTHER PUBLICATIONS

Knipping, K. et al. (2014). "Development of β-lactoglobulin-specific chimeric human IgEk monoclonal antibodies for in vitro safety assessment of whey hydrolysates," PLoS One 9:e106025.

Miller, W.H. et al. (2005). "Evaluation of Beta-Absorbed Fractions in a Mouse Model for $^{90}$Y, $^{188}$Re, $^{166}$Ho, $^{149}$Pm, $^{64}$Cu, and $^{177}$Lu Radionuclides," Cancer Biother. & Biopharm. 20:436-449.

Phillips, G.K. et al. (2015). "Therapeutic uses of anti-PD-1 and anti-PD-L1 antibodies," Int. Immunol. 27:39-46.

Revskaya, E. et al. (2009). "Radioimmunotherapy of experimental human metastatic melanoma with melanin-binding antibodies and in combination with dacarbazine," Clin. Cancer Res. 15:2373-2379.

Sgouros, G. et al. (1999). "Pharmacokinetics and dosimetry of an alpha-particle emitter labeled antibody: 213Bi-HuM195 (anti-CD33) in patients with leukemia," J. Nucl. Med. 40:1935-1946.

Uran, M.E. et al. (2011). "Detection of antibodies against *Paracoccidioides brasiliensis* melanin in in vitro and in vivo studies during infection," Clin. Vaccine Immunol. 18:1680-1688.

Written Opinion of the International Searching Authority dated Jan. 28, 2019, for PCT Application No. PCT/US2018/050955, filed on Sep. 13, 2018, 7 pages.

\* cited by examiner

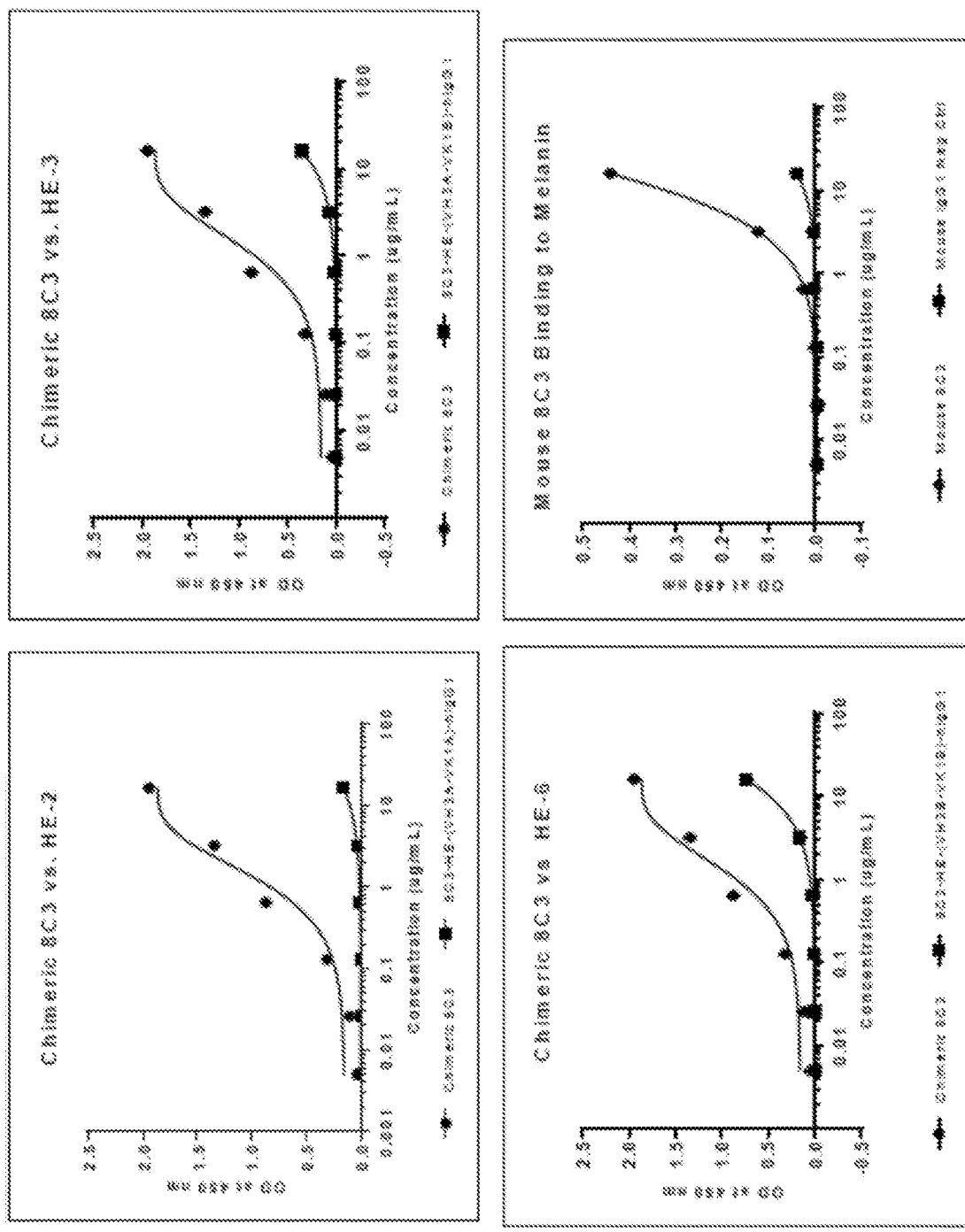
FIG. 2 - continued

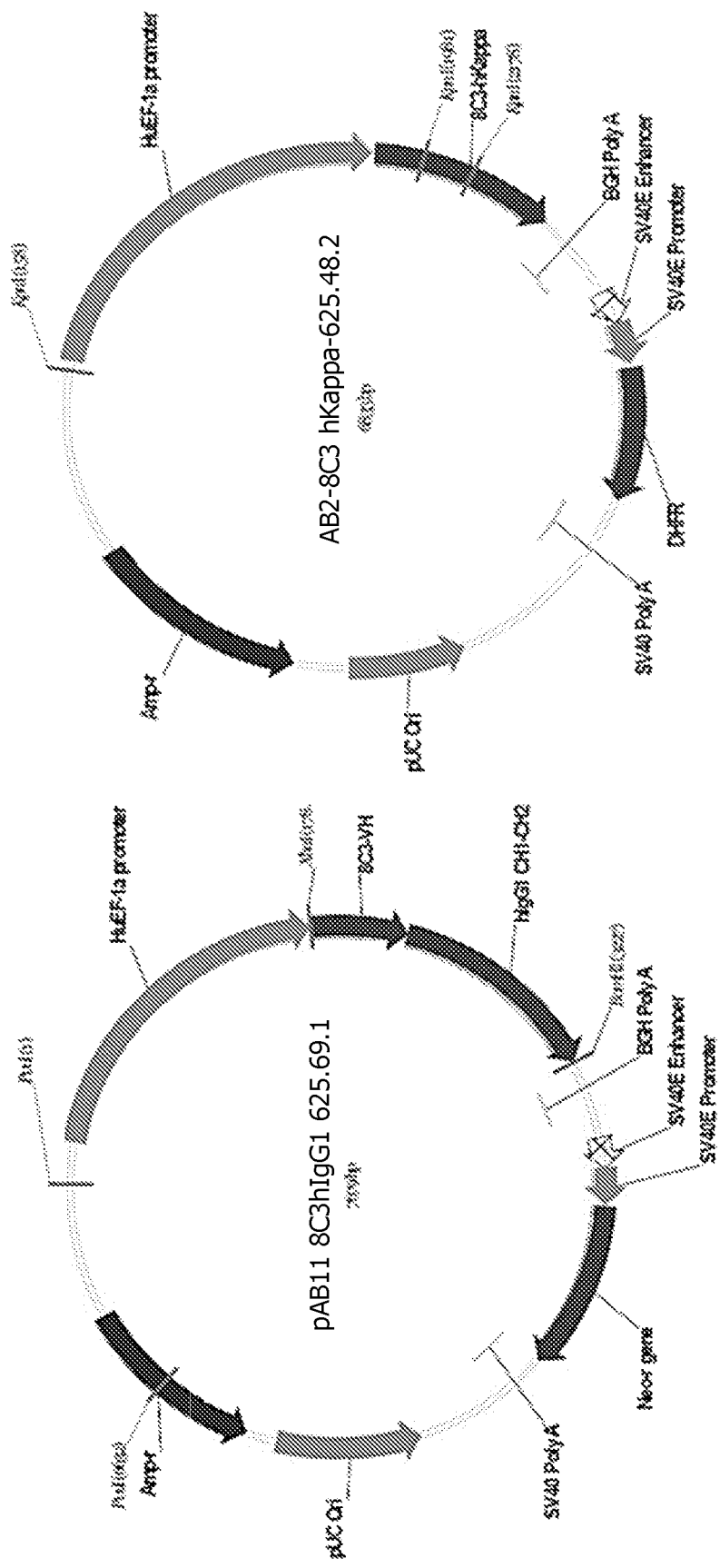

FIG. 5

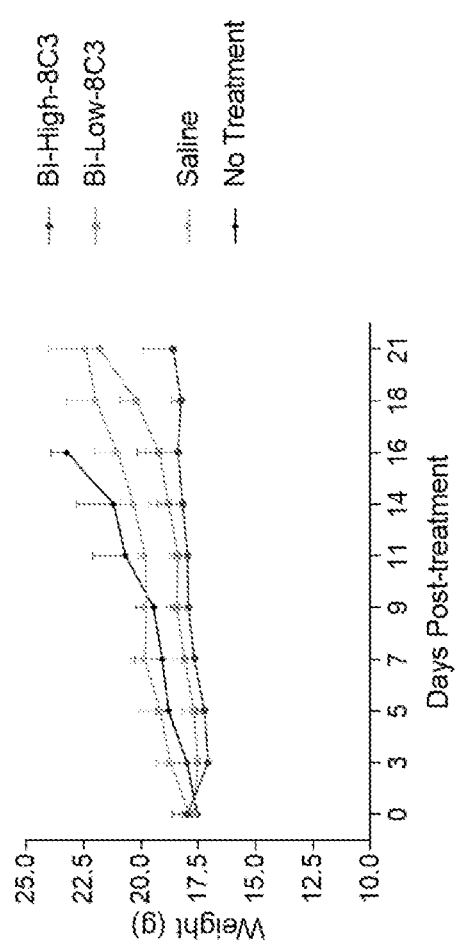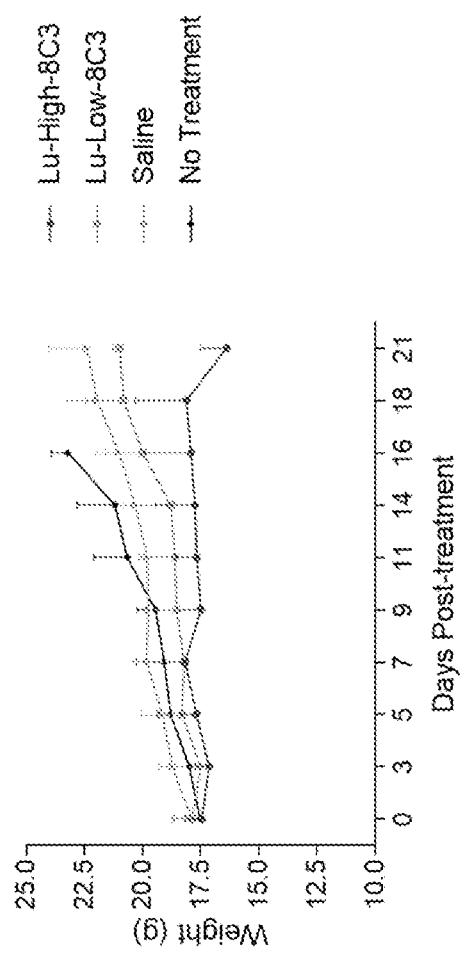
FIG. 14A
FIG. 14B

FIG. 25

| | Antibody ID | Day 11 Titer (µg/mL) | Day 7 Titer (µg/mL) | Ranking |
|---|---|---|---|---|
| Superpool 1 | 14D10 | 129 | 54.9 | 1 |
| | 7B2 | 118.2 | 69.8 | 2 |
| | 18B6 | 106.3 | 31.3 | 3 |
| | 1E12 | 75 | 18.9 | 4 |
| | 14E2 | 72.6 | 37.7 | 5 |
| Superpool 2 | 16B5 | 69.9 | 27.7 | 6 |
| | 12A1 | 61.5 | 42.7 | 7 |
| | 6F10 | 60.2 | 36.3 | 8 |
| | 14G9 | 57.8 | 33.5 | 9 |
| | 13F3 | 55 | 25.3 | 10 |
| Superpool 3 | 16D1 | 46.1 | 22.4 | 11 |
| | 16H4 | 46.1 | 31.9 | 12 |
| | 3C11 | 45.4 | 15.3 | 13 |
| | 14E8 | 44 | 23.6 | 14 |
| | 14E10 | 40.2 | 26.1 | 15 |

FIG. 30

| Clone ID | Day 7 Titer(ug/mL) | Day11 Titer(ug/mL) | Ranking |
|---|---|---|---|
| 1-3D5 | 115.6 | 221.8 | 1 |
| 1-5F6 | 61.3 | 209.6 | 2 |
| 1-16E1 | 86.2 | 190.2 | 3 |
| 1-12C9 | 104.9 | 189.6 | 4 |
| 1-20F10 | 122.3 | 176.1 | 5 |
| 2-11H6 | 96.3 | 163.8 | 6 |
| 2-6A11 | 62.9 | 138.2 | 7 |
| 1-9F6 | 64.5 | 135.2 | 8 |
| 2-1E12 | 73.3 | 134.9 | 9 |
| 2-9B12 | 53.1 | 134.9 | 10 |
| 1-12F12 | 64.9 | 133.7 | 11 |
| 2-11F5 | 91.4 | 129.8 | 12 |
| 1-11H5 | 72.8 | 128.8 | 13 |
| 2-11H12 | 67.4 | 129.3 | 14 |
| 1-14H10 | 72.2 | 128 | 15 |
| 1-4D4 | 73.6 | 125.6 | 16 |
| 2-3H11 | 75.5 | 124.4 | 17 |
| 2-3C7 | 69.4 | 124 | 18 |
| 2-7B5 | 95.2 | 123.8 | 19 |
| 2-18C | 66.5 | 117.7 | 20 |
| 2-11G2 | 53.7 | 117.1 | 21 |
| 2-17C12 | 76.9 | 114.7 | 22 |
| 2-3H6 | 68 | 113 | 23 |
| 2-14G11 | 70.7 | 113.8 | 24 |
| 2-28C3 | 66.8 | 112.8 | 25 |
| 2-5F12 | 29.1 | 109.8 | 26 |
| 1-3H2 | 74.8 | 109.3 | 27 |
| 2-10C7 | 68.3 | 109.9 | 28 |
| 2-17C12 | 55.5 | 106 | 29 |
| 2-3A8 | 49.7 | 106 | 30 |
| 1-9H6 | 26.8 | 105.7 | 31 |
| 2-4G2 | 68.4 | 109.7 | 32 |
| 2-15F12 | 67.7 | 104.4 | 33 |
| 2-2G10 | 75.6 | 100.6 | 34 |
| 2-4H6 | 57.2 | 96.6 | 35 |
| 2-12A6 | 64.5 | 97.6 | 36 |
| 2-11H3 | | | |

FIG. 31

| Clone ID | Max VCD (e6 cells/mL) | Longevity | Titer (mg/L) | Clonality (D0, D1, D2) | Ranking |
|---|---|---|---|---|---|
| 2-3H2 | 9.99 | 17 | 1290.9 | 1,2,2 | 1 |
| 2-3H11 | 12.12 | 15 | 1269.5 | 1,2,4 | 2 |
| 2-11H12 | 12.29 | 15 | 1264.9 | 1,2,4 | 3 |
| 2-20C3 | 16.05 | 14 | 1246.6 | 1,2,4 | 4 |
| 2-1E12 | 11.14 | 16 | 1238.9 | 1,1,3 | 5 |
| 2-8G10 | 14.28 | 15 | 1238 | 1,2,3 | 6 |
| 2-2G10 | 14.26 | 15 | 1204.7 | 1,1,4 | 7 |
| 2-9B12 | 13.08 | 15 | 1186.7 | 1,2,4 | 8 |
| 2-3H6 | 11.74 | 14 | 1184.5 | 1,2,4 | 9 |
| 2-1B2 | 11.41 | 17 | 1167.4 | 1,2,5 | 10 |
| 2-14G11 | 26.56 | 15 | 1159.4 | 1,2,6 | 11 |
| 2-5G7 | 26.05 | 15 | 1159.4 | 1,2,5 | 12 |
| 2-11H3 | 13.65 | 14 | 1125.7 | 1,2,7 | 13 |
| 2-11H6 | 11.90 | 15 | 1116.7 | 1,3,7 | 14 |
| 2-10C7 | 15.39 | 14 | 1100.9 | 1,2,4 | 15 |
| 2-2F12 | 13.05 | 14 | 1099.3 | 1,1,2 | 16 |
| 2-11F5 | 11.06 | 16 | 1092.7 | 0,2,4 | 17 |
| 2-17C12 | 13.75 | 15 | 1073.8 | 1,2,4 | 18 |
| 2-1C7 | 15.81 | 14 | 1029.3 | 1,2,6 | 19 |
| 2-15F12 | 12.49 | 15 | 973.2 | 1,3,4 | 20 |
| 2-12A6 | 9.41 | 14 | 950.2 | 1,2,5 | 21 |
| 2-4H8 | 14.94 | 14 | 898 | 1,2,4 | 22 |
| 2-13A9 | 13.91 | 14 | 873 | 1,2,5 | 23 |
| 2-11G2 | 13.79 | 13 | 825 | 1,2,4 | 24 |
| 1-11H9 | 12.92 | 14 | 789 | 1,2,4 | 25 |
| 1-1D5 | 6.9 | 14 | 742.1 | 1,2,8 | 26 |
| 1-12C9 | 7.51 | 14 | 687.1 | 1,2,3 | 27 |
| 1-16E1 | 9.10 | 14 | 655.6 | 0,2,4 | 28 |

MELANIN ANTIBODIES AND USES THEREOF

CROSS-REFERENCE

This application is a U.S. national stage application, filed under 35 U.S.C. § 371, of International Application No. PCT/US2018/050955, filed on Sep. 13, 2018, which claims the priority benefit of U.S. Provisional Patent Application Ser. No. 62/558,230, filed on Sep. 13, 2017, each of which is incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: RADM_002_01US_SeqList_ST25.txt, date recorded: Jan. 3, 2022, file size 105 kilobytes).

BACKGROUND

Melanoma, the most serious type of skin cancer, develops in the melanin-producing melanocytes. Melanoma can also originate in the uveal tract of the eye, in the mucosal epithelium lining the upper aero-digestive tract, and the intestinal tract. The American Cancer Society estimates that in 2017, about 87,000 new melanomas will be diagnosed and about 9,750 people are expected to die of melanoma, in the United States (https://www.cancer.org/cancer/melanoma-skin-cancer/about/key-statistics.html). Globally, in 2012, melanoma occurred in about 232,000 people and resulted in about 55,000 deaths.

While stage 1 and 2 melanoma can be surgically treated, the aggressive metastatic nature of this malignancy provides a poor prognosis with estimated survival rates of 19%, 13%, and 9% at 3, 5, and 10 years, respectively, for patients with stage IV melanoma. (C M Balch, J E Gershenwald, S J Soong, et al: Final version of 2009 AJCC melanoma staging and classification J Clin Oncol 27: 6199-6206, 2009). Approval by FDA of vemurafenib, which inhibits mutated B-RAF protein, offers hope for 40-60% melanoma patients carrying this mutation. Efforts to restore latent anti-tumor immunity have focused on monoclonal antibody (mAb)-based interventions targeting CTL antigen 4 (CTLA-4) (Hodi F S, O'Day S J, McDermott D F, et al: Improved survival with ipilimumab in patients with metastatic melanoma. N Engl J Med 363:711-723, 2010) and programmed cell death protein 1 (PD-1) on T lymphocytes and its principal ligand (PD-L1) on tumor cells (Phillips G K, Atkins M. Therapeutic uses of anti-PD-1 and anti-PD-L1 antibodies. Int Immunol. 2015; 27(1):39-46). With only a minority of patients experiencing long term progression free survival in response to either anti CTLA-4, or anti PD-1 pathway checkpoint inhibitor immunotherapy, the significant risk of serious autoimmune toxicity associated with these agents, and the high costs of immunotherapy (Fellner, Chris. Ipilimumab (Yervoy) Prolongs Survival in Advanced Melanoma: Serious Side Effects and a Hefty Price Tag May Limit Its Use. *Pharmacy & Therapeutics* 2012:27(9):503-511), there remains an urgent need for other approaches to combat melanoma, especially metastatic melanoma.

SUMMARY

Provided herein are monoclonal antibodies that specifically bind to melanin. The antibodies may be chimeric or humanized. Also provided herein are methods of use and methods of making the antibodies described. For example, the melanin antibodies may be used therapeutically to treat or prevent melanoma.

Accordingly, in one aspect provided herein is a monoclonal antibody that specifically binds to melanin, wherein the antibody is chimeric or humanized.

In some embodiments, the antibody is chimeric. In some embodiments, the antibody is a chimeric mouse-human antibody. In some embodiments, the chimeric antibody comprises mouse variable regions and human constant regions. In some embodiments, the melanin antibody comprises a light chain comprising the amino acid sequence of SEQ ID NO: 1. In some embodiments, the melanin antibody comprises a heavy chain comprising the amino acid sequence of SEQ ID NO: 2. In some embodiments, the melanin antibody comprises a light chain comprising the amino acid sequence of SEQ ID NO: 1 and a heavy chain comprising the amino acid sequence of SEQ ID NO: 2.

In some embodiments, the antibody is humanized. In some embodiments, the antibody is a humanized form from the sequence of a mouse monoclonal antibody. In some embodiments, the antibody is a humanized form from a mouse 8C3 antibody. In some embodiments, the humanized melanin antibody comprises a heavy chain comprising the amino acid sequence of SEQ ID NO: 3 or SEQ ID NO: 4. In some embodiments, the humanized melanin antibody comprises a light chain comprising the amino acid sequence of SEQ ID NO: 5, SEQ ID NO: 6, or SEQ ID NO: 7. In some embodiments, the humanized melanin antibody comprises a heavy chain comprising the amino acid sequence of SEQ ID NO: 3 and a light chain comprising the amino acid sequence of SEQ ID NO: 5. In some embodiments, the humanized melanin antibody comprises a heavy chain comprising the amino acid sequence of SEQ ID NO: 3 and a light chain comprising the amino acid sequence of SEQ ID NO: 6. In some embodiments, the humanized melanin antibody comprises a heavy chain comprising the amino acid sequence of SEQ ID NO: 3 and a light chain comprising the amino acid sequence of SEQ ID NO: 7. In some embodiments, the humanized melanin antibody comprises a heavy chain comprising the amino acid sequence of SEQ ID NO: 4 and a light chain comprising the amino acid sequence of SEQ ID NO: 5. In some embodiments, the humanized melanin antibody comprises a heavy chain comprising the amino acid sequence of SEQ ID NO: 4 and a light chain comprising the amino acid sequence of SEQ ID NO: 6. In some embodiments, the humanized melanin antibody comprises a heavy chain comprising the amino acid sequence of SEQ ID NO: 4 and a light chain comprising the amino acid sequence of SEQ ID NO: 7. In some embodiments, the heavy chain of the humanized melanin antibody comprises at least one of the CDR sequences of SEQ ID NO: 8, SEQ ID NO: 9, or SEQ ID NO: 10. In some embodiments, the light chain of the humanized melanin antibody comprises at least one of the CDR sequences of SEQ ID NO: 11, SEQ ID NO: 12, SEQ ID NO: 13, SEQ ID NO: 14, or SEQ ID NO: 15. In some embodiments, the heavy chain of the humanized melanin antibody comprises at least one of the CDR sequences of SEQ ID NO: 8, SEQ ID NO: 9, or SEQ ID NO: 10, and the light chain of the humanized melanin antibody comprises at least one of the CDR sequences of SEQ ID NO: 11, SEQ ID NO: 12, SEQ ID NO: 13, SEQ ID NO: 14, or SEQ ID NO: 15. In some embodiments, the heavy chain of the humanized melanin antibody comprises the CDR sequences from SEQ ID NO: 8, SEQ ID NO: 9, or SEQ ID NO: 10, and/or the light chain comprises the CDR sequences from SEQ ID NO: 3 or SEQ ID NO: 4.

In some embodiments, the chimeric or humanized monoclonal melanin antibody is an antigen binding fragment.

In some embodiments, the chimeric or humanized monoclonal melanin antibody is a bispecific antibody. In some embodiments, the bispecific antibody comprises a first arm that targets melanin and a second arm that targets an antigen comprising an immune checkpoint inhibitor. In some embodiments, the immune checkpoint inhibitor is CTLA4, PD-1, or PD-L1.

In some embodiments, the chimeric or humanized monoclonal melanin antibody is conjugated to an agent. In some embodiments, the agent is a radionuclide. In some embodiments, the radionuclide is 213-Bi. In some embodiments, the radionuclide is 177-Lu. In some embodiments, the agent is conjugated to the antibody through a linker.

In a related aspect, provided herein is a pharmaceutical composition comprising any one of the chimeric or humanized monoclonal melanin antibodies provided herein, and a pharmacologically acceptable carrier.

In another aspect, provided herein is a method for treating melanoma in a subject, comprising administering a therapeutically effective amount of any one of the monoclonal chimeric or humanized melanin antibodies or compositions comprising such antibodies, as described herein. In a related aspect, provided herein is a therapeutically effective amount of any one of the monoclonal chimeric or humanized melanin antibodies or compositions comprising such antibodies, as described herein for use in treating melanoma.

In some embodiments, the melanoma is metastasized. In some embodiments, the administration selectively induces the cell death of melanoma cells. In some embodiments, the method comprises administering to the subject an effective amount of at least one additional agent. In some embodiments, the agent is an immune checkpoint inhibitor. In some embodiments, the immune checkpoint inhibitor is selected from CTLA-4, PD-1, and PDL-1. In some embodiments, the antibody or composition is administered intravenously.

In another aspect, provided herein is a method of making a conjugated melanin antibody comprising conjugating any one of the monoclonal chimeric or humanized melanin antibodies described herein to an agent. In some embodiments, the agent is a radionuclide. In some embodiments, the radionuclide is 213-Bi. In some embodiments, the radionuclide is 177-Lu.

In another aspect provided herein are polynucleotides encoding the amino acid sequence of any one of the chimeric or humanized monoclonal melanin antibodies provided herein. In some embodiments, the polynucleotide comprises the nucleotide sequence of SEQ ID NO: 17. In some embodiments, the polynucleotide comprises the nucleotide sequence of SEQ ID NO: 18. In some embodiments, the polynucleotide has been codon optimized for expression in a human. Also provided herein are vectors comprising polynucleotides encoding the amino acid sequence of any one of the chimeric or humanized monoclonal melanin antibodies provided herein, and cell lines comprising such vectors. Also provided herein are clonal cell lines expressing any one of the chimeric or humanized monoclonal melanin antibodies provided herein In another aspect, provided herein is a kit comprising any one of the chimeric or humanized monoclonal antibodies or pharmaceutical compositions comprising such antibodies.

All of the above features described herein (including any accompanying claims, abstract and drawings), and/or all of the steps of any method or process so disclosed, may be combined in any combination, except combinations where at least some of such features and/or steps are mutually exclusive.

For a better understanding of the invention, and to show how embodiments of the same may be carries into effect, reference will now be made, by way of example, to the accompanying diagrammatic drawings.

BRIEF DESCRIPTION OF THE DRAWINGS

FIG. 5 show alignments of the heavy chains (SEQ ID NOs: 30-33) of the antibodies described herein.

FIGS. 14A and 14B are a series of graphs depicting body weight of mice treated with either: high dose of 213Bi-h8C3 HE-5, or low dose of 213Bi-h8C3 HE-5, or high dose of 177Lu-h8C3 HE-5, or low dose of 177Lu-h8C3 HE-5, or 80 µg unlabeled ("cold") h8C3 HE-5, or left untreated.

aspartate transaminase (AST), 15C) urea, and 15D) creatinine, in mice treated with either: high dose of 213Bi-h8C3 HE-5, or low dose of 213Bi-h8C3 HE-5, or left untreated.

Figure 16B:
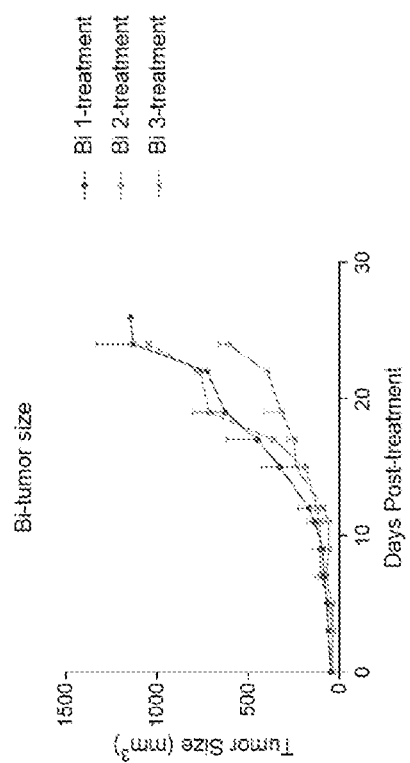
Figure 16A:
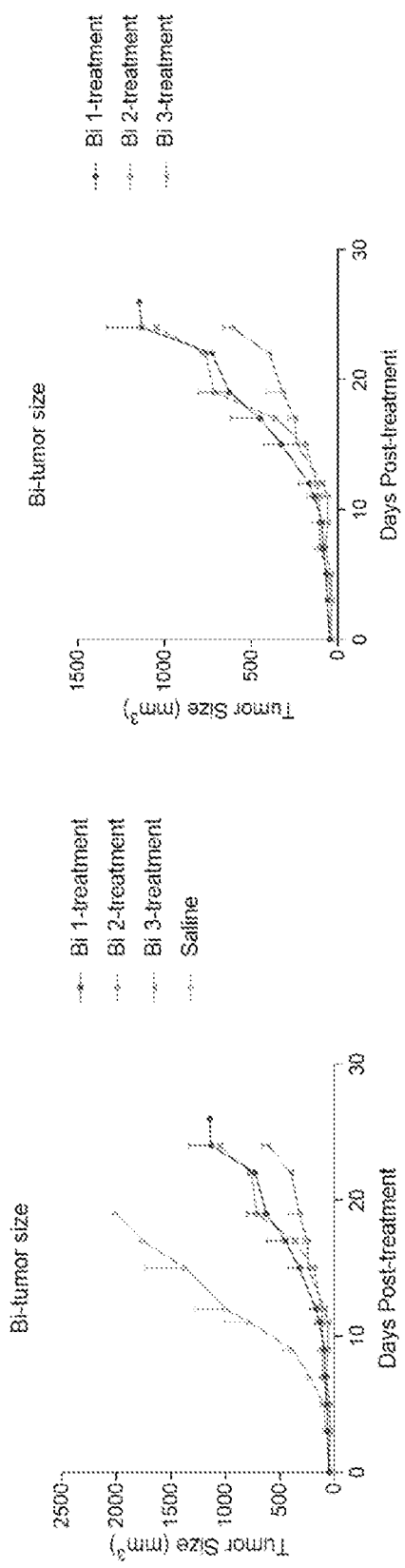
Figure 16C:
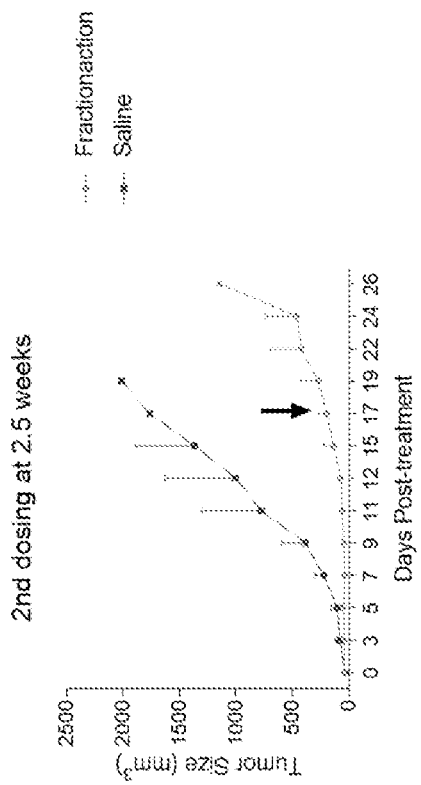

FIGS. 16A-16C are a series of graphs depicting changes in tumor volume in tumor-bearing mice randomized into groups of 8 and treated with either: single dose 400 μCi 213-h8C3 HE-5 on Day 0, or 400 μCi 213-h8C3 HE-5 on Day 0 and on Day 3, or 400 μCi 213-h8C3 HE-5 on Day 0, Day 3 and Day 7. On Day 16 mice in the single dose group were treated with another 400 Ci 213-h8C3 HE-5 dose.

Figure 17:
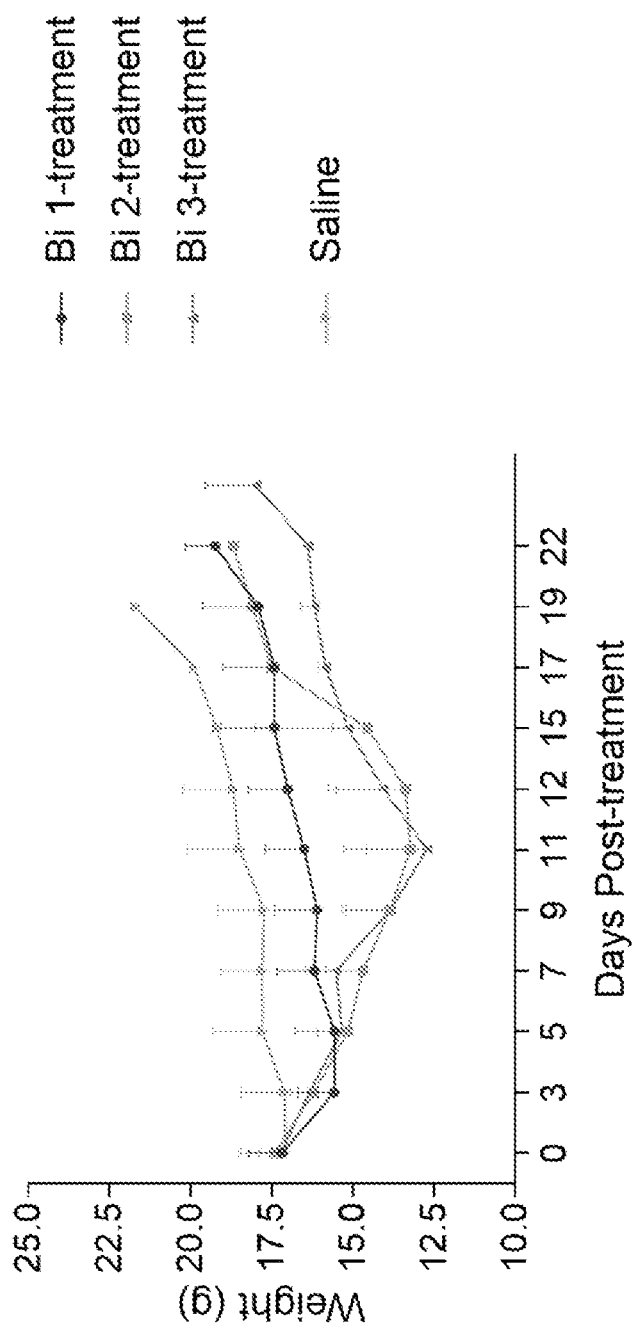

FIG. 17 is a graph depicting changes in body weight in tumor-bearing mice randomized into groups of 8 and treated with either: single dose 400 μCi 213-h8C3 HE-5 on Day 0, or 400 μCi 213-h8C3 HE-5 on Day 0 and on Day 3, or 400 μCi 213-h8C3 HE-5 on Day 0, Day 3 and Day 7. On Day 16 mice in the single dose group were treated with another 400 μCi 213-h8C3 HE-5 dose.

FIG. 18 is a series of graphs depicting blood counts of 18A white blood cells, 18B) red blood cells, 18C) and platelets in tumor-bearing mice randomized into groups of 8 and treated with either: single dose 400 μCi 213-h8C3 HE-5 on Day 0, or 400 μCi 213-h8C3 HE-5 on Day 0 and on Day 3, or 400 μCi 213-h8C3 HE-5 on Day 0, Day 3 and Day 7. On Day 16 mice in the single dose group were treated with another 400 μCi 213-h8C3 HE-5 dose.

FIG. 19 is a series of graphs depicting concentrations of blood analytes: 19A) alanine transaminase (ALT), 19B) aspartate transaminase (AST), 19C) urea, and 19D) creatinine, in tumor-bearing mice randomized into groups of 8 and treated with either: single dose 400 μCi 213-h8C3 HE-5 on Day 0, or 400 μCi 213-h8C3 HE-5 on Day 0 and on Day 3, or 400 μCi 213-h8C3 HE-5 on Day 0, Day 3 and Day 7. On Day 16 mice in the single dose group were treated with another 400 Ci 213-h8C3 HE-5 dose.

Figure 20:
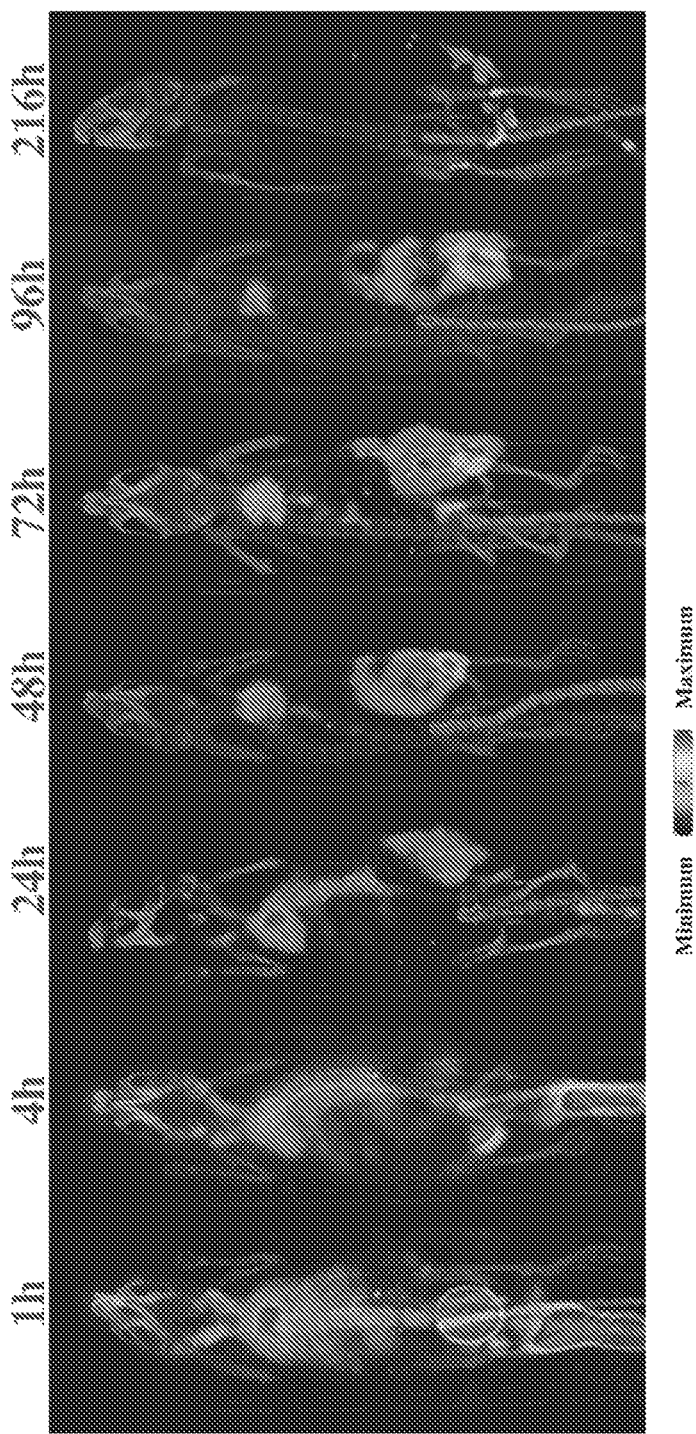

FIG. 20 is a series of microSPECT/CT images of a mouse 1 h, 4 h, 24 h, 48 h, 72 h, 96 h, and 216 h post injection with 200 μCi 111In at a 5:1 mCi/mg specific activity with a CHXA" conjugated h8C3 HE-5 antibody.

Figure 21:
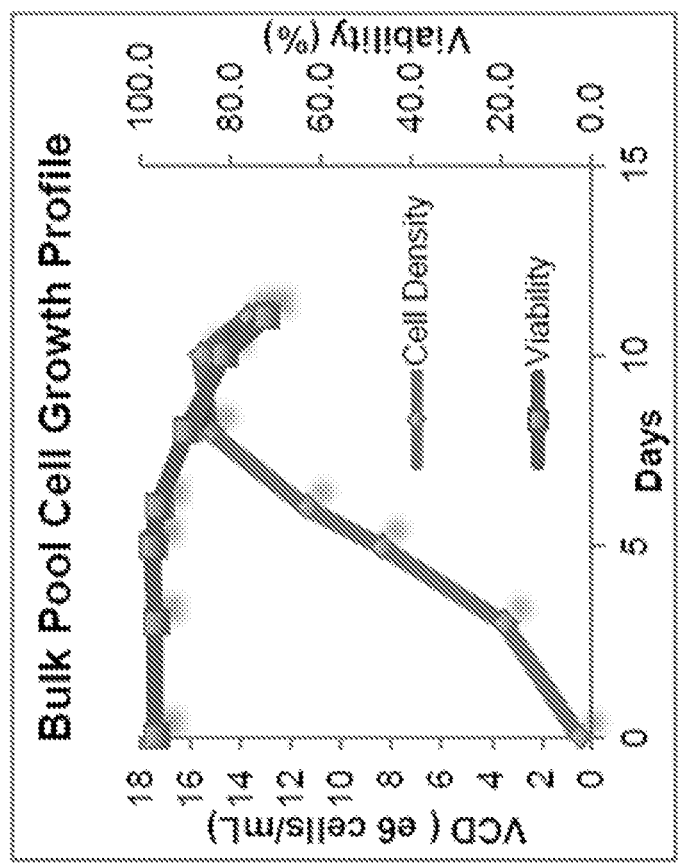

FIG. 21 is a graph depicting bulk pool cell growth.

Figure 22:
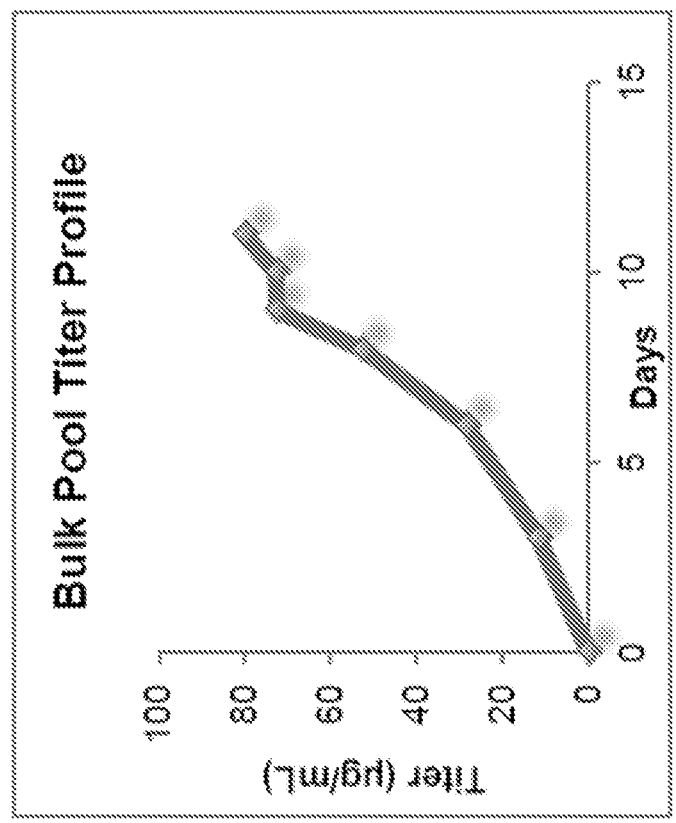

FIG. 22 is a graph depicting the bulk pool titer profile as measured by ForteBio Octet Red.

Figure 23:
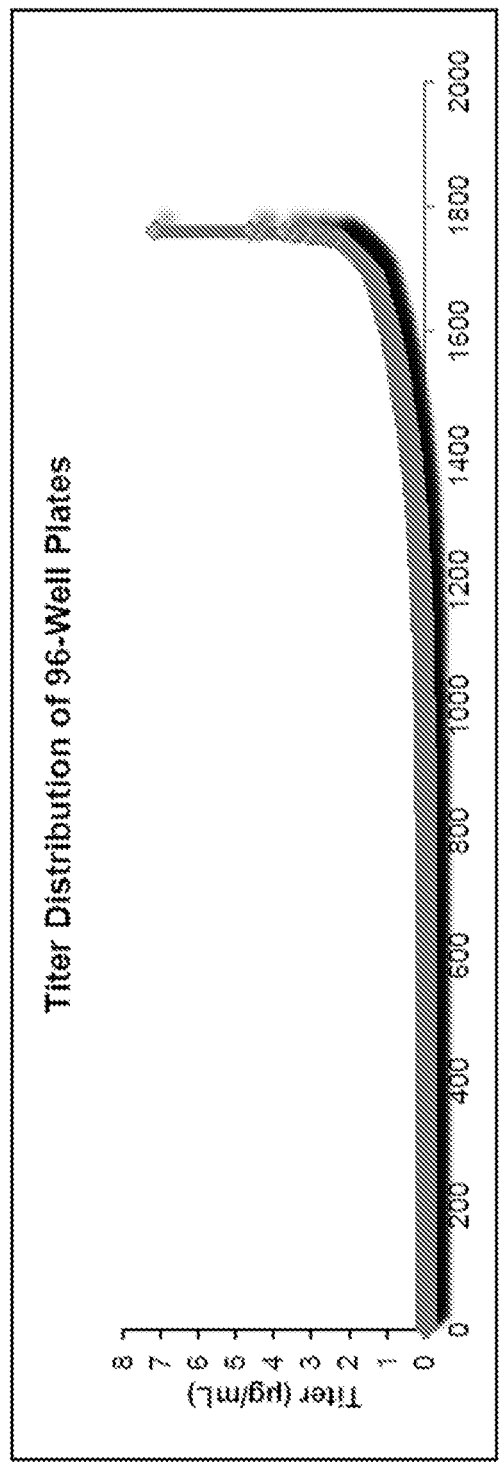

FIG. 23 is a graph depicting the titer profile across 96-well plates of cells expressing antibody.

Figure 24:
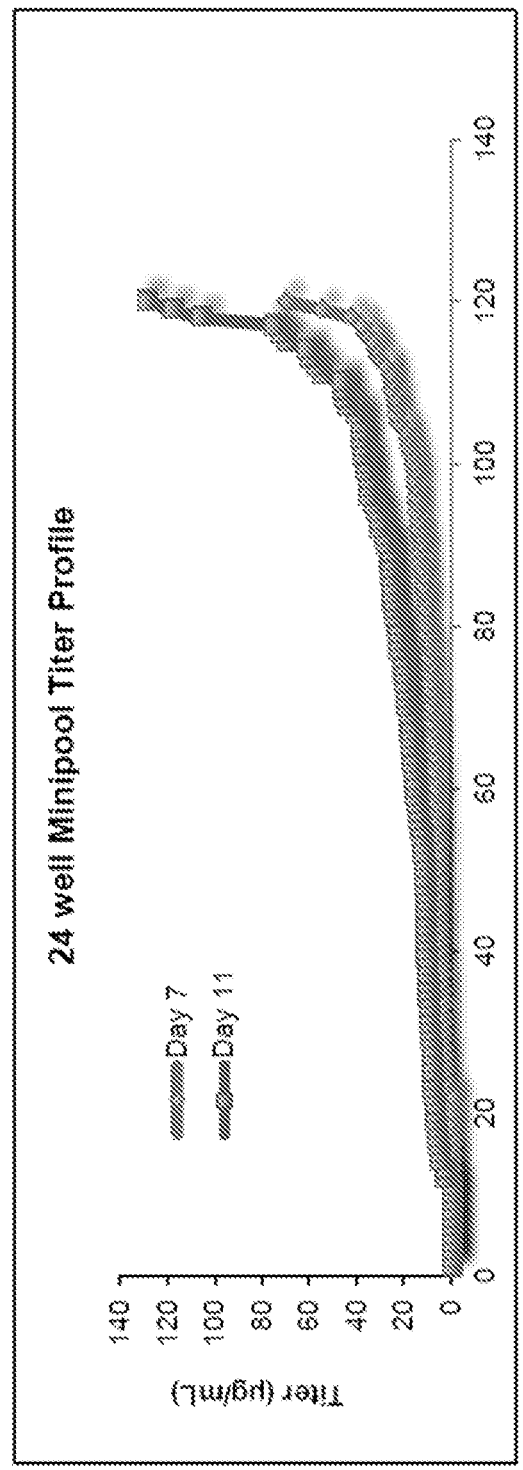

FIG. 24 is a graph depicting the titer profile of the 120-top expressing pools from FIG. 23 selected to grow in 24-well plates. Three super-pools were selected. Super-pool 1 was composed of the three highest expresser mini-pools with titers ranging from 106 to 129 μg/mL, the Super-pool 2 was composed of five mini-pools with titers ranging from 60 to 75 μg/mL and the Super-pool 3 was composed of seven mini-pools with titers ranging from 40 to 58 μg/mL.

FIG. 25 is a chart ranking the highest expressing pools from the 24-well plate screening. Three super-pools were selected. Super-pool 1 was composed of the three highest expresser mini-pools with titers ranging from 106 to 129 μg/mL, the Super-pool 2 was composed of five mini-pools with titers ranging from 60 to 75 μg/mL and the Super-pool 3 was composed of seven mini-pools with titers ranging from 40 to 58 μg/mL.

Figure 26:
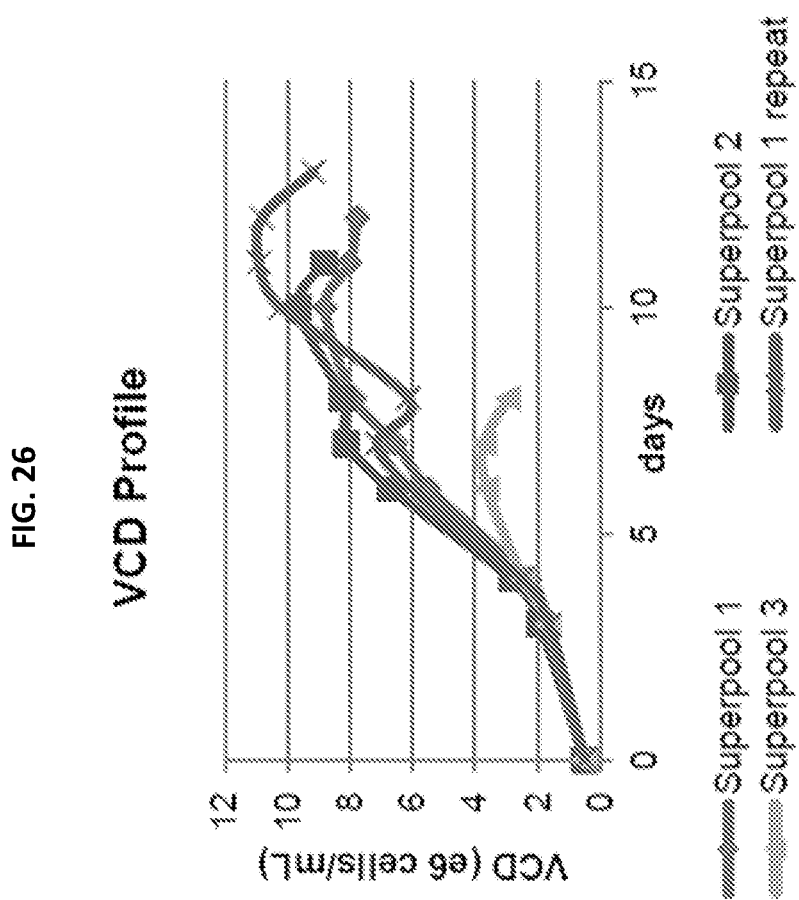

FIG. 26 is a graph depicting the growth curve of each super-pool.

Figure 27:
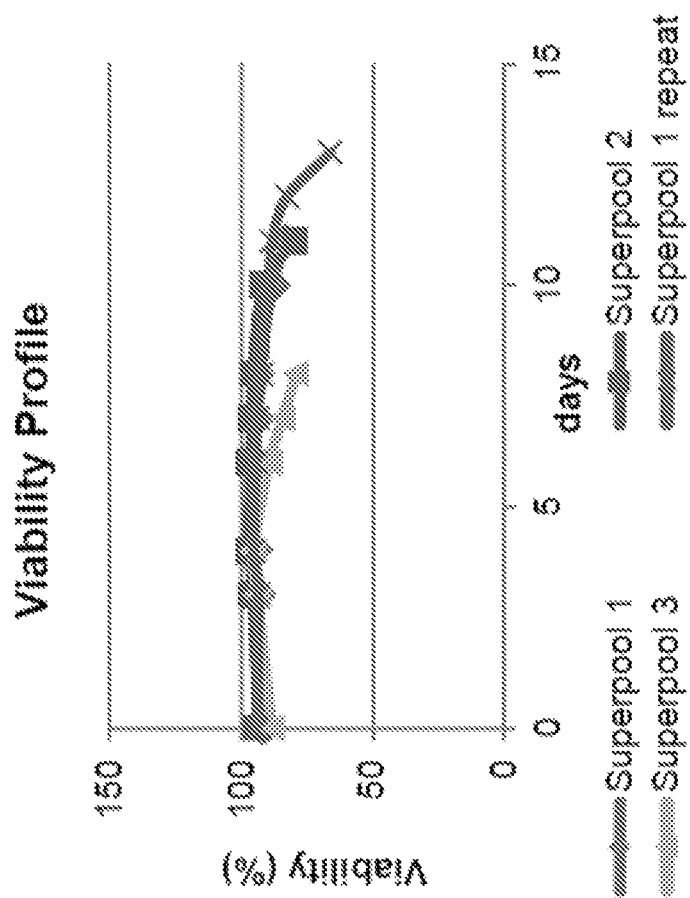

FIG. 27 is a graph depicting the viability of each super-pool.

Figure 28:
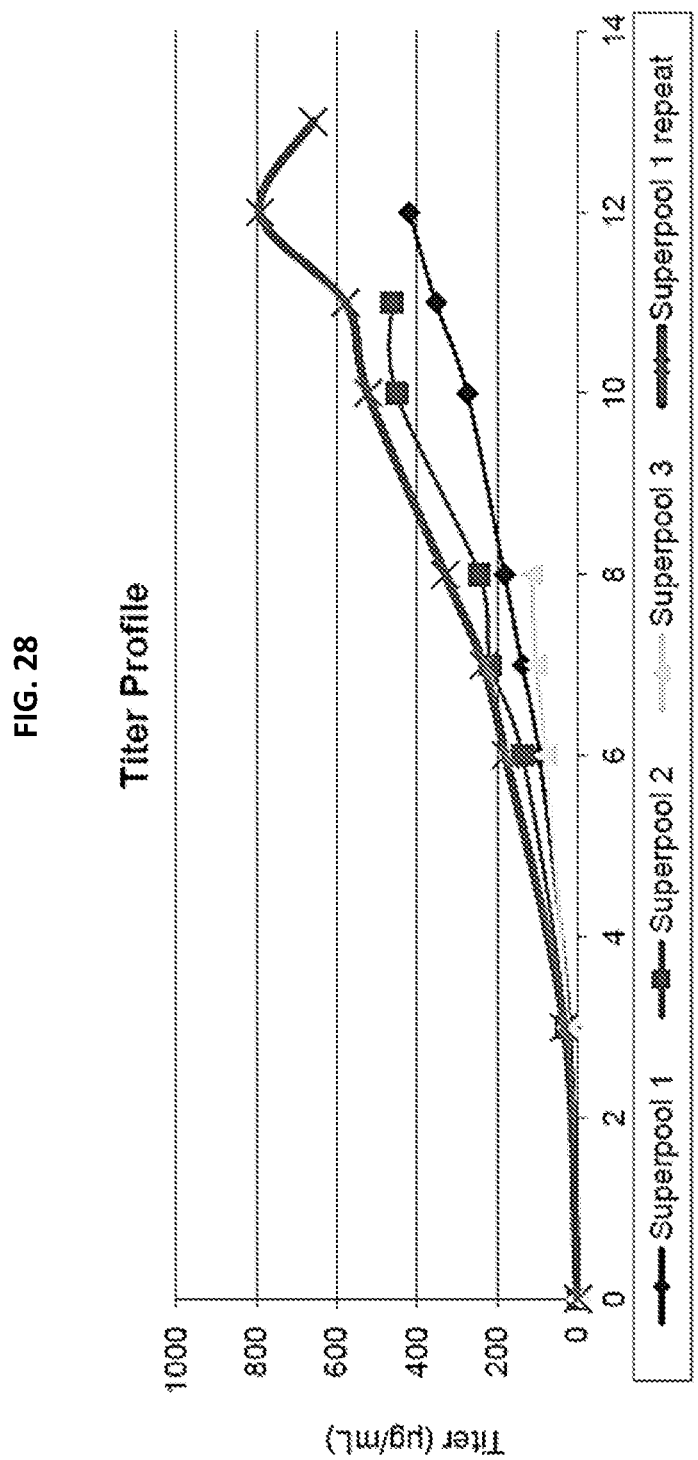

FIG. 28 is a graph depicting the titer profile of each super-pool.

Figure 29:
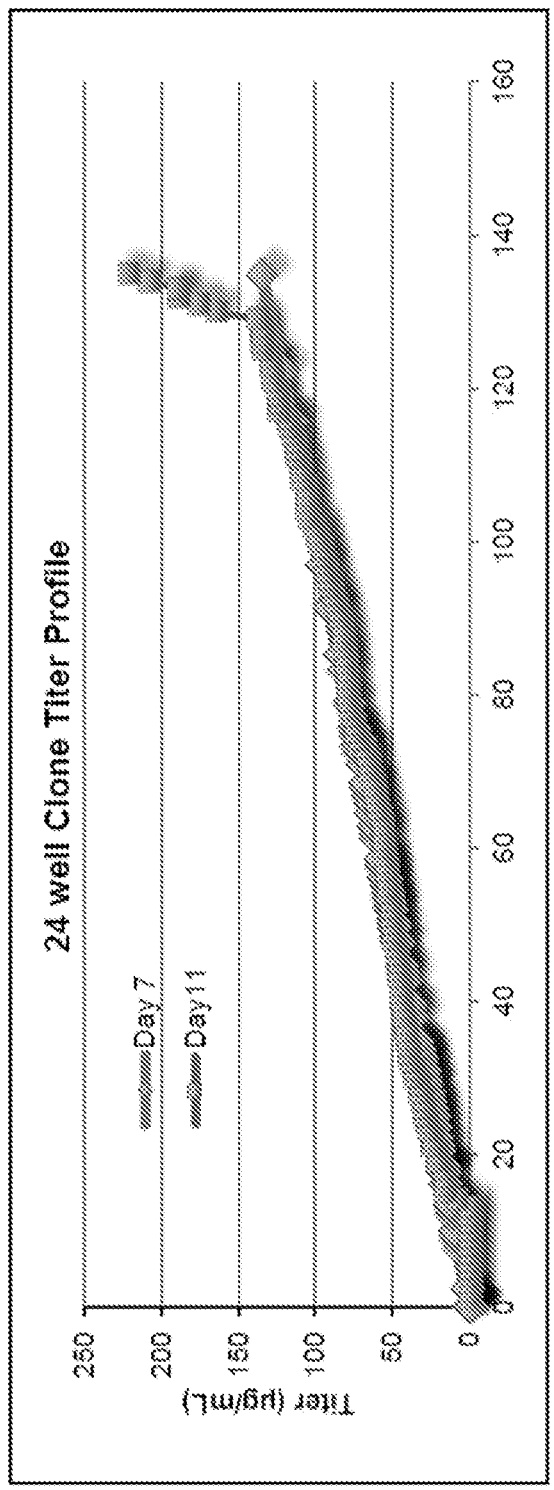

FIG. 29 is a graph depicting the titer profile of clones from the 24-well stage that were ranked based on expression levels measured on day 11 using a ForteBio Octet Red with a Protein A sensor and compared to a standard curve obtained with the 8C3 HE-5 antibody purified from the bulk pool.

FIG. 30 is a chart highlighting the 36 clones with the highest expression levels from the 24-well stage.

FIG. 31 is a chart highlighting the highest expressing clones: Clones 2-3H2, 2-3H11, 2-11H12 and 2-20C3 with respective expression levels of 1.29 g/L, 1.27 g/L, 1.26 g/L, and 1.25 g/L.

DETAILED DESCRIPTION OF THE INVENTION

Provided herein are antibodies that specifically bind to melanin. The antibodies may be chimeric or humanized. Also provided herein are methods of use and methods of making the antibodies described. For example, the melanin antibodies may be used therapeutically to treat or prevent melanoma, comprising administering to a subject in need thereof an antibody or a pharmaceutical composition thereof. The melanin antibodies may also be used for diagnostic purposes, to detect a melanoma in a sample from a subject. Also provided are methods of producing the melanin antibodies described herein.

Unless defined otherwise herein, all technical and scientific terms used herein have the same meaning as commonly understood by one of ordinary skill in the art to which this invention belongs.

Numeric ranges are inclusive of the numbers defining the range.

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

Other definitions of terms may appear throughout the specification.

For any of the structural and functional characteristics described herein, methods of determining these characteristics are known in the art.

Melanin Antibodies

Provided herein are antibodies that specifically bind to melanin. In some embodiments, the melanin is mammalian melanin, e.g. human melanin, or murine melanin. In other embodiments, the melanin is a non-mammalian melanin.

The term "antibody" as used herein throughout is in the broadest sense and includes, but is not limited to, a monoclonal antibody, polyclonal antibody, human antibody, humanized antibody, non-human antibody, chimeric antibody, bispecific antibody, multi-specific antibody, antigen-binding fragments of the antibody (e.g Fab fragment, a Fab'2 fragment, a CDR or a ScFv), antibody-drug conjugates, and other antibody fragments that retain specificity for a melanin antigen.

The antibody can be any of an IgA, IgD, IgE, IgG, or IgM antibody. The IgA antibody can be an IgA1 or an IgA2 antibody. The IgG antibody can be an IgG1, IgG2, IgG2a, IgG2b, IgG3 or IgG4 antibody. A combination of any of these antibodies can also be used.

In some embodiments, the melanin antibody is conjugated for a variety of purposes including, but not limited to, for use in therapeutics, detection, diagnostics, visualization, quantification, sorting, and for use in biological assays.

In some embodiments, the antibody is a humanized antibody that specifically binds to melanin. In some embodiments, the humanized antibody is a humanized version of a mouse monoclonal 8C3 IgG antibody (NCBI GenBank accession number KX346264; Urán M E, Nosanchuk J D, Restrepo A, Hamilton A J, Gómez B L, Cano L E. Detection of antibodies against *Paracoccidioides brasiliensis* melanin in in vitro and in vivo studies during infection. Clin Vaccine Immunol. 2011 October; 18(10):1680-8).

In some embodiments, the antibody is a chimeric antibody that specifically binds to melanin. In an exemplary embodiment, the antibody is a chimeric mouse-human antibody. The chimeric mouse-human antibody can comprise human variable regions and mouse constant regions. In some embodiments, the constant region is of the IgG type, e.g. of the IgG type. In some embodiments, the constant region is not of the IgG type, e.g. not of the human IgG type. In some embodiments, the constant region is of the IgM type, e.g. of the human IgM type. In some embodiments, the constant region is not of the IgM type, e.g. not of the human IgM type.

Table 1 provides exemplary sequences for the antibodies and antigen-binding fragments provided herein.

TABLE 1

Exemplary Melanin Antibody Amino Acid Sequences

SEQ ID NO: 2: Amino Acid Sequence of the Heavy Chain of a melanin Chimeric Antibody
(8C3-hIgG1)
EVQLEESGGGLVQPGGSMKVSCAASGFTFSDAWMDWVRQSPEKGLEWVAEIRSKAHN
HATYYAESVKGRFTISRDDSKSSVYLQMNSLRAEDTGTYYCTRGGYYGNYGFFAYWGQ
GTLVTVSAASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK SEQ ID NO: 1: Amino Acid Sequence of the Light Chain of a melanin Chimeric Antibody
(8C3-hKappa)
DILMTQSPASLAVSLGQRATISCRASESVDSYGTSFMHWYQQKPGQPPKLLIYLASNLES
GVPARFSGSGSRTDFTLTIDPVEADDAATYYCQQNNEYPYTFGGGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC SEQ ID NO: 3: Amino Acid Sequence of the Heavy Chain of a melanin Humanized
Antibody (8C3-HE-VH3A-hIgG1)
EVQLVESGGGLVQPGGSMRVSCAASGFTFSDAWMDWVRQAPGKGLEWVAEIRSKAHN
HATYYAESVKGRFTISRDDSKSTVYLQMNSLRAEDTGTYYCTRGGYYGNYGFFAYWGQ
GTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGK SEQ ID NO: 4: Amino Acid Sequence of the Heavy Chain of a melanin Humanized
Antibody (8C3-HE-VH3B-hIgG1)
EVQLVESGGGLVQPGGSMRVSCAASGFTFSDAWMDWVRQAPGKGLEWVAEIRSKAHN
HATYYADSVKGRFTISRDNSKNTVYLQMNSLRAEDTGVYYCTRGGYYGNYGFFAYWG
QGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK SEQ ID NO: 5: Amino Acid Sequence of the Light Chain of a melanin Humanized Antibody
(8C3-HE-VK1A-hKappa)
DIQMTQSPSSLSVSLGDRATITCRASESVDSYGTSFMHWYQQKPGKPPKLLIYLASNLESG
VPSRFSGSGSRTDFTLTISPVQAEDFATYYCQQNNEYPYTFGQGTKLEIKRTVAAPSVFIFP
PSDEQLKSGTASVVCLLNNFYPREAKVQWKVDNALQSGNSQESVTEQDSKDSTYSLSST
LTLSKADYEKHKVYACEVTHQGLSSPVTKSFNRGEC SEQ ID NO: 6: Amino Acid Sequence of the Light Chain of a melanin Humanized Antibody
(8C3-HE-VK1B-hKappa)
DIQMTQSPSSLSVSVGDRATITCRASESVDSYGTSFMHWYQQKPGKPPKLLIYLASNLQS
GVPSRFSGSGSRTDFTLTISPVQAEDFATYYCQQNNEYPYTFGQGTKLEIKRTVAAPSVFI
FPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC TABLE 1-continued Exemplary Melanin Antibody Amino Acid Sequences

```
SEQ ID NO: 7: Amino Acid Sequence of the Light Chain of a melanin Humanized Antibody
(8C3-HE-VK4-hKappa)
DIVMTQSPDSLAVSLGERATINCKASESVDSYGTSFMHWYQQKPGQPPKLLIYLASNRES
GVPDRFSGSGSRTDFTLTISPVQAEDVATYYCQQNNEYPYTFGQGTKLEIKRTVAAPSVFI
FPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

SEQ ID NO: 8: V_H CDR1
FTFSDAWMD

SEQ ID NO: 9: V_H CDR2
WVAEIRSKAHNHATYY

SEQ ID NO: 10: V_H CDR3
RGGYYGNYGFFAY

SEQ ID NO: 11: V_L CDR1
ESVDSYGTSFME

SEQ ID NO: 12: V_L CDR2
LLIYLASNLES

SEQ ID NO: 13: V_L CDR2
LLIYLASNLQS

SEQ ID NO: 14: V_L CDR2
LLIYLASNRES

SEQ ID NO: 15: V_L CDR3
QQNNEYPY
```

In some embodiments, the melanin antibody comprises a light chain comprising the amino acid sequence of SEQ ID NO: 1.

In some embodiments, the melanin antibody comprises a heavy chain comprising the amino acid sequence of SEQ ID NO: 2.

In some embodiments, the melanin antibody comprises a light chain comprising the amino acid sequence of SEQ ID NO: 1 and a heavy chain comprising the amino acid sequence of SEQ ID NO: 2.

In some embodiments, the melanin antibody comprises a heavy chain comprising the amino acid sequence of SEQ ID NO: 3 or SEQ ID NO: 4.

In some embodiments, the melanin antibody comprises a light chain comprising the amino acid sequence of SEQ ID NO: 5, SEQ ID NO: 6, or SEQ ID NO: 7.

In some embodiments, the melanin antibody comprises a heavy chain comprising the amino acid sequence of SEQ ID NO: 3 and a light chain comprising the amino acid sequence of SEQ ID NO: 5.

In some embodiments, the melanin antibody comprises a heavy chain comprising the amino acid sequence of SEQ ID NO: 3 and a light chain comprising the amino acid sequence of SEQ ID NO: 6.

In some embodiments, the melanin antibody comprises a heavy chain comprising the amino acid sequence of SEQ ID NO: 3 and a light chain comprising the amino acid sequence of SEQ ID NO: 7.

In some embodiments, the melanin antibody comprises a heavy chain comprising the amino acid sequence of SEQ ID NO: 4 and a light chain comprising the amino acid sequence of SEQ ID NO: 5.

In some embodiments, the melanin antibody comprises a heavy chain comprising the amino acid sequence of SEQ ID NO: 4 and a light chain comprising the amino acid sequence of SEQ ID NO: 6.

In some embodiments, the melanin antibody comprises a heavy chain comprising the amino acid sequence of SEQ ID NO: 4 and a light chain comprising the amino acid sequence of SEQ ID NO: 7.

In some embodiments, the melanin antibody comprises a light chain comprising the variable portion of any one of the light chain sequences provided for in Table 1. In some embodiments, the melanin antibody comprises a light chain comprising only the variable portion of any one of the light chain sequences provided for in Table 1.

In some embodiments, the melanin antibody comprises a light chain comprising the CDRs contained in any one of the light chain sequences provided for in Table 1. In some embodiments, the melanin antibody comprises a heavy chain comprising the CDRs contained in any one of the heavy chain sequences provided for in Table 1.

In some embodiments, the melanin antibody comprises a heavy chain comprising the variable portion of any one of the heavy chain sequences provided for in Table 1. In some embodiments, the melanin antibody comprises a heavy chain comprising only the variable portion of any one of the heavy chain sequences provided for in Table 1.

In some embodiments, the heavy chain of the melanin antibody comprises at least one of the complementarity-determining region (CDR) sequences of SEQ ID NO: 8, SEQ ID NO: 9, or SEQ ID NO: 10. In some embodiments, the heavy chain of the melanin antibody comprises the complementarity-determining region (CDR) sequences of SEQ ID NO: 8, SEQ ID NO: 9, and SEQ ID NO: 10.

In some embodiments, the light chain of the melanin antibody comprises at least one of the CDR sequences of SEQ ID NO: 11, SEQ ID NO: 12, SEQ ID NO: 13, SEQ ID NO: 14, or SEQ ID NO: 15. In some embodiments, the light chain of the melanin antibody comprises the complementarity-determining region (CDR) sequences of SEQ ID NO: 11, SEQ ID NO: 12, and SEQ ID NO: 15. In some embodiments, the light chain of the melanin antibody comprises the complementarity-determining region (CDR) sequences of SEQ ID NO: 11, SEQ ID NO: 13, and SEQ ID NO: 15. In some embodiments, the light chain of the melanin antibody comprises the complementarity-determining region (CDR) sequences of SEQ ID NO: 11, SEQ ID NO: 14, and SEQ ID NO: 15.

In some embodiments, the melanin antibody is a humanized antibody selected from the group consisting of HE-1, HE-2, HE-3, HE-4, HE-5, and HE-6.

In some embodiments, the melanin antibody is a bispecific antibody. For example, the bispecific antibody can comprise a first arm that targets melanin and a second arm that targets an antigen comprising an additional therapeutic target, for example an immune checkpoint inhibitor. In some embodiments, the bispecific antibody comprises a first arm that targets melanin and a second arm that targets an immune checkpoint inhibitor, for example, the second arm targets CTLA4, PD-1, or PD-L1.

In some embodiments, the melanin antibody is conjugated to an agent including, but not limited to, a radionuclide (also referred to as a radioactive nuclide, radioisotope or radioactive isotope), a cytotoxin, a chemotherapeutic agent, a drug, an enzyme, a detectable agent, a cytokine, a hormone, an oligonucleotide, or a second antibody.

In another exemplary embodiment, the melanin antibody is conjugated to a cytotoxin.

In another exemplary embodiment, the melanin antibody is conjugated to a microtubule inhibitor.

In another exemplary embodiment, the melanin antibody is conjugated to a nucleic acid damaging agent, such as a DNA alkylator, a DNA cleaving agent, a DNA cross-linker, a DNA intercalator, or other DNA damaging agent.

In another exemplary embodiment, the melanin antibody is conjugated to a radionuclide. The choice of the particular radionuclide with which the melanin antibody is conjugated may be determined by the size of the melanoma tumor to be treated and its localization in the body, taking into consideration the emission range in the tissue and half-life. Radionuclides include alpha emitters, beta emitters, and positron emitters.

Exemplary radionuclides include but are not limited to alpha emitters, beta emitters, and positron emitters.

Examples of alpha emitters include: 213-Bismuth (half-life 46 minutes), 223-Radium (half-life 11.3 days), 224-Radium (half-life 3.7 days), 225-Radium (half-life 14.8 days), 225-Actinium (half life 10 days), 212-Lead (half-life 10.6 hours), 212-Bismuth (half-life 60 minutes), 211-Astatin (half-life 7.2 hours), 255-Fermium (half-life 20 hours) and 227-Thorium (half-life 18.7 days).

Examples of beta emitters include: 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131 Iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199 Gold (half-life 3.1 days).

Examples of positron emitters include (half-life in parenthesis): 52Mn (21.1 min); 62Cu (9.74 min); 68Ga (68.1 min); 11C (20 min); 82Rb (1.27 min); 1 10In (1.15 h); 118Sb (3.5 min); 122I (3.63 min); 18F (1.83 h); 34$^{m}$Cl (32.2 min); 38K (7.64 min); 51Mn (46.2 min); 52Mn (5.59 days); 52Fe (8.28 h); 55Co (17.5 h); 61Cu (3.41 h); 64Cu (12.7 h); 72As (1.08 days); 75Br (1.62 h); 76Br (16.2 h); 82$^{m}$Rb (6.47 h); 83Sr (1.35 days); 86Y (14.7 h); 89Zr (3.27 days); 94$^{m}$Tc (52.0 min); 120I (1.35 h); 124 I (4.18 days). 64-Copper is a mixed positron, electron and Auger electron emitter.

Exemplary radionuclides also may include: $^{99m}$Tc, $^{201}$Tl, $^{133}$Xe, $^{11}$C, $^{62}$Cu, $^{18}$F, $^{68}$Ga, $^{13}$N, $^{15}$O, $^{38}$K, $^{82}$Rb, $^{99}$mTc (Technetium), $^{188}$Re, $^{213}$Bi (213-Bismuth), $^{125}$I, $^{131}$I, $^{89}$Zr, $^{111}$In, $^{123}$I, and $^{131}$I.

In some embodiments, the melanin antibody is a humanized antibody and is conjugated to $^{213}$B. In some embodiments, the melanin antibody is a humanized antibody selected from the group consisting of HE-1, HE-2, HE-3, HE-4, HE-5, and HE-6 (referring to Table 4) and is conjugated to $^{213}$B. In some embodiments, the humanized melanin antibody comprises a heavy chain comprising the amino acid sequence of SEQ ID NO: 3 or SEQ ID NO: 4 and is conjugated to $^{213}$B. In some embodiments, the humanized melanin antibody comprises a light chain comprising the amino acid sequence of SEQ ID NO: 5, SEQ ID NO: 6, or SEQ ID NO: 7 and is conjugated to $^{213}$B. In some embodiments, the humanized melanin antibody comprises a heavy chain comprising the amino acid sequence of SEQ ID NO: 3 and a light chain comprising the amino acid sequence of SEQ ID NO: 5 and is conjugated to $^{213}$B. In some embodiments, the humanized melanin antibody comprises a heavy chain comprising the amino acid sequence of SEQ ID NO: 3 and a light chain comprising the amino acid sequence of SEQ ID NO: 6 and is conjugated to $^{213}$B. In some embodiments, the humanized melanin antibody comprises a heavy chain comprising the amino acid sequence of SEQ ID NO: 3 and a light chain comprising the amino acid sequence of SEQ ID NO: 7 and is conjugated to $^{213}$B. In some embodiments, the humanized melanin antibody comprises a heavy chain comprising the amino acid sequence of SEQ ID NO: 4 and a light chain comprising the amino acid sequence of SEQ ID NO: 5 and is conjugated to $^{213}$B. In some embodiments, the humanized melanin antibody comprises a heavy chain comprising the amino acid sequence of SEQ ID NO: 4 and a light chain comprising the amino acid sequence of SEQ ID NO: 6 and is conjugated to $^{213}$B. In some embodiments, the humanized melanin antibody comprises a heavy chain comprising the amino acid sequence of SEQ ID NO: 3 and a light chain comprising the amino acid sequence of SEQ ID NO: 4 and is conjugated to $^{213}$B. In some embodiments, the heavy chain of the humanized melanin antibody comprises at least one of the CDR sequences of SEQ ID NO: 8, SEQ ID NO: 9, or SEQ ID NO: 10 and is conjugated to $^{213}$B. In some embodiments, the light chain of the humanized melanin antibody comprises at least one of the CDR sequences of SEQ ID NO: 11, SEQ ID NO: 12, SEQ ID NO: 13, SEQ ID NO: 14, or SEQ ID NO: 15 and is conjugated to $^{213}$B.

In some embodiments, the melanin antibody is a humanized antibody and is conjugated to $^{77}$Lu. In some embodiments, the melanin antibody is a humanized antibody selected from the group consisting of HE-1, HE-2, HE-3, HE-4, HE-5, and HE-6 (referring to Table 4) and is conjugated to $^{177}$Lu. In some embodiments, the humanized melanin antibody comprises a heavy chain comprising the amino acid sequence of SEQ ID NO: 3 or SEQ ID NO: 4 and is conjugated to $^{177}$Lu. In some embodiments, the humanized melanin antibody comprises a light chain comprising the amino acid sequence of SEQ ID NO: 5, SEQ ID NO: 6, or SEQ ID NO: 7 and is conjugated to $^{177}$Lu. In some embodiments, the humanized melanin antibody comprises a heavy chain comprising the amino acid sequence of SEQ ID NO: 3 and a light chain comprising the amino acid sequence of SEQ ID NO: 5 and is conjugated to $^{177}$Lu. In some embodiments, the humanized melanin antibody comprises a heavy chain comprising the amino acid sequence of SEQ ID NO: 3 and a light chain comprising the amino acid sequence of SEQ ID NO: 6 and is conjugated to $^{177}$Lu. In some embodiments, the humanized melanin antibody comprises a heavy chain comprising the amino acid sequence of SEQ ID NO: 3 and a light chain comprising the amino acid sequence of SEQ ID NO: 7 and is conjugated to $^{177}$Lu. In some embodiments, the humanized melanin antibody comprises a heavy chain comprising the amino acid sequence of SEQ ID NO: 4 and a light chain comprising the amino acid sequence of SEQ ID NO: 5 and is conjugated to $^{177}$Lu. In some embodiments, the humanized melanin antibody comprises a heavy chain comprising the amino acid sequence of SEQ ID NO: 4 and a light chain comprising the amino acid sequence of SEQ ID NO: 6 and is conjugated to $^{177}$Lu. In some embodiments, the humanized melanin antibody comprises a heavy chain comprising the amino acid sequence of SEQ ID NO: 3 and a light chain comprising the amino acid sequence of SEQ ID NO: 4 and is conjugated to $^{177}$Lu. In some embodiments, the heavy chain of the humanized melanin antibody comprises at least one of the CDR sequences of SEQ ID NO: 8, SEQ ID NO: 9, or SEQ ID NO: 10 and is conjugated to $^{177}$Lu. In some embodiments, the light chain of the humanized melanin antibody comprises at least one of the CDR sequences of SEQ ID NO: 11, SEQ ID NO: 12, SEQ ID NO: 13, SEQ ID NO: 14, or SEQ ID NO: 15 and is conjugated to $^{177}$Lu.

In different embodiments, the dose of the radionuclide in any one of the embodiments described herein for therapeutic purposes is between 1-1000 mCi.

In some embodiments, the antibody is conjugated to one or more equivalents of an agent. In some embodiments, the antibody is conjugated to one equivalent of the agent. In some embodiments, the antibody is conjugated to two, three, four, five, six, seven, eight, nine, ten, or greater than ten equivalents of the agent. In some embodiments, the mixture of antibodies is such that the average number of agents conjugated to each antibody is two, three, four, five, six, seven, eight, nine, ten, or greater than ten equivalents of the agent is one, two, three, four, five, six, seven, eight, nine, ten, or greater than ten.

In some embodiments, the antibody comprises one or more site-specific amino acid sequence modifications such that the number of agents that can be conjugated to the antibody can be modulated.

In another exemplary embodiment, the melanin antibody is conjugated to an anti-inflammatory agent.

In another exemplary embodiment, the melanin antibody is conjugated to a detectable agent (label). In some embodiments, the detectable agent is a diagnostic agent. In some embodiments, the melanin antibody is conjugated to a detectable label, a spin label, a colorimetric label, a radioactive label, an enzymatic label, a fluorescent label, or a magnetic label.

In some embodiments, the agent is conjugated to the melanin antibody via linker. In some embodiments, the agent is conjugated to the melanin antibody via a cleavable linker. In some embodiments, the agent is conjugated to the melanin antibody via a non-cleavable linker.

In some embodiments, the melanin antibody is conjugated or attached to a solid surface, for example a bead, resin or a microplate.

Provided herein are antibodies specific for melanin from any mammalian and non-mammalian species. In some embodiments, the melanin antibody is specific for human melanin. In some embodiments, the melanin antibody is cross reactive with melanin from other species.

The antibodies provided herein bind melanin with specificity. In some embodiments, these antibodies bind melanin with specificity and selectivity.

In certain embodiments, an antibody provided herein has a dissociation constant (Kd) of range of 0.0001 nM to 1 µM.

For example, Kd of the antibody may be about 1 M, about 100 nM, about 50 nM, about 10 nM, about 5 nM, about 1 nM, about 0.5 nM, about 0.1 nM, about 0.05 nM, about 0.01 nM, about 0.005 nM, about 0.001 nM, about 0.0005 nM, or even about 0.0001 nM.

Production of Melanin Antibodies

A variety of immunoassay formats may be used to select antibodies specifically immunoreactive with melanin. For example, solid-phase ELISA immunoassays may be used to select monoclonal antibodies specific to melanin (see, e.g., Harlow and Lane (1988) Antibodies, A Laboratory Manual, Cold Spring Harbor Publications, New York, for a description of immunoassay formats and conditions that may be used to determine specific immunoreactivity).

Production of the antibodies provided herein may be by any method known to those with skill in the art. For example, in some embodiments, the melanin antibodies are produced by recombinant cells engineered to express the desired light chains and heavy chains of the desired antibody. In some embodiments the antibodies are produced by hybridomas.

In some embodiments, any peptide comprising the melanin antigen, optionally linked to the immunogenic carrier, is used for immunization using standard protocols.

The quality and titer of generated antibodies may be assessed using techniques known to those in the art.

For the purposes of binding and expression, a signal peptide sequence may be expressed in frame with the antibody component of interest. Table 2 provides exemplary amino acid and nucleotide sequences that encode exemplary signal peptides. In some embodiments, the signal peptide assists a cell line in secretion of the antibody. In some embodiments, the signal peptide is designated "VK-I region Walker". In some embodiments the signal peptide is the native signal peptide found in many human Ig Kappa Chains. In some embodiments, the antibodies are synthesized in a cellular system and comprise a signal peptide sequence, for example the sequence of SEQ ID NO: 16. As provided herein, any one of the exemplary melanin antibody sequences provided in Table 1 may further include a signal peptide sequence. Thus in some embodiments, an antibody sequence of the invention comprises any one of SEQ ID NOs: 1-7 in combination with a N-terminal signal peptide sequence, for example the signal peptide sequence of SEQ ID NO: 16.

TABLE 2

Exemplary Signal Peptide Sequences

SEQ ID NO: 16: Signal peptide amino acid sequence
MDMRVPAQLLGLLLLWLRGAR

SEQ ID NO: 17: Signal peptide nucleotide sequence
ATGGACATGAGAGTGCCGGCGCAACTGCTCGGCCTGCTGTTGCTGTGGCT
GAGGGGAGCCAGATGC The inventive compositions described herein also include nucleic acids encoding the antibodies, vectors comprising any of the nucleic acids encoding the antibodies, and host cells comprising any such vectors. Exemplary nucleotide sequences are provided in Table 3A. In some embodiments, the nucleic acids encoding the antibodies further include a signal peptide nucleotide sequence, for example the sequence of SEQ ID NO: 17. Table 3B provides exemplary melanin antibody expressing plasmid nucleotide sequences.

TABLE 3A

Exemplary Melanin Antibody Nucleotide Sequences

SEQ ID NO: 18: DNA sequence of pAB11 625.69.1 heavy chain of a chimeric melanin antibody gene (8C3-hIgG1)
GAAGTGCAGCTCGAGGAATCCGGAGGAGGACTGGTGCAGCCTGGCGGAAGCATGAAGG
TGTCATGCGCGGCTTCCGGATTCACCTTCTCGGACGCCTGGATGGATTGGGTCAGACAAA
GCCCCGAAAAAGGCCTGGAATGGGTGGCCGAGATTCGGTCCAAGGCCCATAACCACGCC
ACCTACTACGCCGAGTCCGTGAAGGGGCGCTTTACTATCTCCCGGGATGACTCGAAGTCG
TCCGTGTACCTCCAGATGAACTCATTGAGGGCCGAGGACACTGGGACCTACTACTGTACC
CGCGGAGGCTACTACGGGAACTATGGTTTCTTCGCCTACTGGGGCCAGGGTACCCTCGTG
ACTGTCAGCGCGGCCAGCACCAAGGGCCCCAGCGTGTTCCCACTGGCCCCAAGCTCCAA
GTCAACCTCCGGCGGAACTGCTGCGCTGGGCTGCTTGGTGAAGGACTACTTCCCCGAACC
GGTCACCGTGTCCTGGAACAGCGGAGCCCTGACCTCGGGAGTCCACACTTTCCCCGCTGT
GCTGCAGTCGTCCGGCCTGTACTCGCTCTCGTCCGTGGTCACTGTCCCGTCCTCGTCCCTG
GGTACTCAGACCTACATTTGCAACGTCAACCACAAGCCTTCAAACACGAAAGTGGACAA
GAAGGTCGAGCCGAAGTCCTGCGACAAAACCCATACTTGCCCTCCTTGTCCGGCTCCCGA
ACTGCTGGGCGGACCTTCCGTGTTCCTCTTCCCGCCTAAGCCGAAAGACACCCTGATGAT
CAGCAGGACTCCGGAAGTGACATGCGTGGTGGTGGACGTGTCGCACGAGGACCCGGAGG
TCAAGTTTAATTGGTACGTGGACGGAGTGGAAGTCCACAACGCCAAGACCAAGCCACGG
GAAGAACAGTACAATTCCACCTATCGCGTGGTGTCCGTGCTTACCGTGCTTCACCAAGAC
TGGCTGAACGGAAAGGAGTACAAGTGCAAAGTGTCAAACAAAGCCCTGCCTGCCCCAAT
CGAAAAGACCATCAGCAAGGCCAAGGGGCAGCCTCGGGAACCCCAAGTGTACACTCTCC
CGCCGTCAAGAGATGAACTGACCAAGAACCAAGTGTCCCTCACTTGTCTCGTGAAGGGA
TTCTACCCCTCCGATATCGCCGTGGAGTGGGAATCCAACGGGCAACCCGAGAACAACTA
CAAGACCACCCCTCCGGTGCTTGATTCCGATGGCTCCTTCTTCCTCTACTCCAAGCTGACC
GTGGACAAGTCAAGATGGCAGCAGGGGAACGTGTTCTCCTGCTCCGTCATGCACGAGGC
CCTGCACAACCATTACACCCAGAAGTCTCTGTCGCTGAGCCCGGGAAAATAA SEQ ID NO: 19: DNA sequence of pAB2 625.48.2 light chain of a chimeric melanin antibody gene (8C3-hKappa)
GACATCCTGATGACTCAGTCACCCGCTAGCCTTGCGGTGTCCCTCGGACAACGCGCCACC
ATCCTCTGTCGGGCCTCCGAATCCGTGGACTCCTACGGCACCTCCTTCATGCACTGGTAC
CAGCAGAAGCCAGGACAGCCTCCCAAGCTGTTGATCTATCTGGCCTCGAATCTGGAATCA
GGAGTGCCGGCTCGGTTCAGCGGCTCCGGATCACGCACTGACTTCACGCTGACCATTGAC
CCCGTGGAGGCAGATGACGCCGCGACCTACTACTGCCAGCAGAACAACGAATACCCTTA
CACTTTCGGCGGGGGTACCAAGCTCGAAATCAAGCGGACAGTGGCAGCCCCATCGGTGT
TCATTTTCCCGCCGTCGGATGAGCAGCTCAAGTCCGGTACTGCCTCCGTGGTCTGCCTGCT
GAACAACTTTTACCCTCGCGAAGCGAAGGTCCAATGGAAAGTGGATAACGCCCTCCAGT
CCGGAAACTCCCAGGAGTCTGTCACCGAGCAGGACTCAAAGGACAGCACTTACTCCCTG
TCCTCGACTCTGACCCTGTCGAAGGCAGATTACGAGAAGCACAAAGTGTACGCCTGCGA
AGTGACCCATCAAGGCCTTTCCAGCCCGGTCACCAAGAGCTTCAATCGGGGGAGTGT
TAG SEQ ID NO: 20 DNA Sequence encoding the Light Chain of a melanin Humanized Antibody (8C3-HE-VK4-hKappa)
ATGGACATGAGAGTGCCGGCGCAACTGCTCGGCCTGCTGTTGCTGTGGCTGAGGGGA
GCCAGATGCGACATCGTGATGACTCAGTCACCCGATAGCCTTGCGGTGTCCCTCGGA
GAACGCGCCACCATCAACTGTAAAGCCTCCGAATCCGTGGACTCCTACGGCACCTCC
TTCATGCACTGGTACCAGCAGAAGCCAGGACAGCCTCCCAAGCTGTTGATCTATCTG
GCCTCGAATCGGAATCAGGAGTGCCGGACCGGTTCAGCGGCTCCGGATCACGCACT
GACTTCACGCTGACCATTAGCCCCGTGCAAGCAGAGGACGTGGCGACCTACTACTGC
CAGCAGAACAACGAATACCCTTACACTTTCGGCCAGGGTACCAAGCTCGAAATCAAG
CGGACAGTGGCAGCCCCATCGGTGTTCATTTTCCCGCCGTCGGATGAGCAGCTCAAG
TCCGGTACTGCCTCCGTGGTCTGCCTGCTGAACAACTTTTACCCTCGCGAAGCGAAGG
TCCAATGGAAAGTGGATAACGCCCTCCAGTCCGGAAACTCCCAGGAGTCTGTCACCG
AGCAGGACTCAAAGGACAGCACTTACTCCCTGTCCTCGACTCTGACCCTGTCGAAGG
CAGATTACGAGAAGCACAAAGTGTACGCCTGCGAAGTGACCCATCAAGGCCTTTCCA
GCCCGGTCACCAAGAGCTTCAATCGGGGGAGTGTTAGTAA SEQ ID NO: 21 DNA Sequence encoding the Light Chain of a melanin Humanized Antibody (8C3-HE-VK1A-hKappa)
ATGGACATGAGAGTGCCGGCGCAACTGCTCGGCCTGCTGTTGCTGTGGCTGAGGGGA
GCCAGATGCGACATCCAGATGACTCAGTCACCCTCGAGCCTTAGCGTGTCCCTCGGA
GATGCGCCACCATCACCTGTCGGGCCTCCGAATCCGTGGACTCCTACGGCACCTCCT
TCATGCACTGGTACCAGCAGAAGCCAGGAAAGCCTCCCAAGCTGTTGATCTATCTGG
CCTCGAATCTGGAATCAGGAGTGCCGTCGCGGTTCAGCGGCTCCGGATCACGCACTG
ACTTCACGCTGACCATTAGCCCCGTGCAAGCAGAGGACTTTGCGACCTACTACTGCC
AGCAGAACAACGAATACCCTTACACTTTCGGCCAGGGTACCAAGCTCGAAATCAAGC
GGACAGTGGCAGCCCCATCGGTGTTCATTTTCCCGCCGTCGGATGAGCAGCTCAAGT
CCGGTACTGCCTCCGTGGTCTGCCTGCTGAACAACTTTTACCCTCGCGAAGCGAAGGT
CCAATGGAAAGTGGATAACGCCCTCCAGTCCGGAAACTCCCAGGAGTCTGTCACCGA
GCAGGACTCAAAGGACAGCACTTACTCCCTGTCCTCGACTCTGACCCTGTCGAAGGC TABLE 3A-continued Exemplary Melanin Antibody Nucleotide Sequences AGATTACGAGAAGCACAAAGTGTACGCCTGCGAAGTGACCCATCAAGGCCTTTCCAG
CCCGGTCACCAAGAGCTTCAATCGGGGGAGTGTTAGTAA SEQ IN NO: 22 DNA Sequence encoding Light Chain of a melanin Humanized Antibody
(8C3-HE-VK1B-hKappa)
ATGGACATGAGAGTGCCGGCGCAACTGCTCGGCCTGCTGTTGCTGTGTGGCTGAGGGGA
GCCAGATGCGACATCCAGATGACTCAGTCACCCTCGAGCCTTAGCGTGTCCGTGGGA
GATCGCGCCACCATCACCTGTCGGGCCTCCGAATCCGTGGACTCCTACGGCACCTCCT
TCATGCACTGGTACCAGCAGAAGCCAGGAAAGCCTCCCAAGCTGTTGATCTATCTGG
CCTCGAATCTGCAGTCAGGAGTGCCGTCGCGGTTCAGCGGCTCCGGATCACGCACTG
ACTTCACGCTGACCATTAGCCCCGTGCAAGCAGAGGACTTTGCGACCTACTACTGCC
AGCAGAACAACGAATACCCTTACACTTTCGGCCAGGGTACCAAGCTCGAAATCAAGC
GGACAGTGGCAGCCCCATCGGTGTTCATTTTCCCGCCGTCGGATGAGCAGCTCAAGT
CCGGTACTGCCTCCGTGGTCTGCCTGCTGAACAACTTTTACCCTCGCGAAGCGAAGGT
CCAATGGAAAGTGGATAACGCCCTCCAGTCCGGAAACTCCCAGGAGTCTGTCACCGA
GCAGGACTCAAAGGACAGCACTTACTCCCTGTCCTCGACTCTGACCCTGTCGAAGGC
AGATTACGAGAAGCACAAAGTGTACGCCTGCGAAGTGACCCATCAAGGCCTTTCCAG
CCCGGTCACCAAGAGCTTCAATCGGGGGAGTGTTAGTAA SEQ ID NO: 23 DNA Sequence encoding the Heavy Chain of a melanin Humanized
Antibody (8C3-HE-VH3A-hIgG1)
ATGGACATGCGCGTGCCGGCACAACTGCTGGGCCTGCTGCTGCTTTGGCTGCGGGGA
GCTAGATGCGAAGTGCAGCTCGTCGAATCCGGAGGAGGACTGGTGCAGCCTGGCGG
AAGCATGCGCGTGTCATGCGCGGCTTCCGGATTCACCTTCTCGGACGCCTGGATGGA
TTGGGTCAGACAAGCGCCCGGCAAAGGCCTGGAATGGGTGGCCGAGATTCGGTCCA
AGGCCCATAACCACGCCACCTACTACGCCGAGTCCGTGAAGGGGCGCTTTACTATCT
CCCGGGATGACTCGAAGTCGACGGTGTACCTCCAGATGAACTCATTGAGGGCCGAGG
ACACTGGGACCTACTACTGTACCCGCGGAGGCTACTACGGGAACTATGGTTTCTTCG
CCTACTGGGGCCAGGGTACCCTCGTGACTGTCAGCAGCGCCAGCACCAAGGGCCCCA
GCGTGTTCCCACTGGCCCCAAGCTCCAAGTCAACCTCCGGCGGAACTGCTGCGCTGG
GCTGCTTGGTGAAGGACTACTTCCCCGAACCGGTCACCGTGTCCTGGAACAGCGGAG
CCCTGACCTCGGGAGTCCACACTTTCCCCGCTGTGCTGCAGTCGTCCGGCCTGTACTC
GCTCTCGTCCGTGGTCACTGTCCCGTCCTCGTCCCTGGGTACTCAGACCTACATTTGC
AACGTCAACCACAAGCCTTCAAACACGAAAGTGGACAAGAAGGTCGAGCCGAAGTC
CTGCGACAAAACCCATACTTGCCCTCCTTGTCCGGCTCCCGAACTGCTGGGCGGACCT
TCCGTGTTCCTCTTCCCGCCTAAGCCGAAAGACACCCTGATGATCAGCAGGACTCCG
GAAGTGACATGCGTGGTGGTGGACGTGTCGCACGAGGACCCGGAGGTCAAGTTTAAT
TGGTACGTGGACGGAGTGGAAGTCCACAACGCCAAGACCAAGCCACGGGAAGAACA
GTACAATTCCACCTATCGCGTGGTGTCCGTGCTTACCGTGCTTCACCAAGACTGGCTG
AACGGAAAGGAGTACAAGTGCAAAGTGTCAAACAAAGCCCTGCCTGCCCCAATCGA
AAAGACCATCAGCAAGGCCAAGGGGCAGCCTCGGGAACCCCAAGTGTACACTCTCC
CGCCGTCAAGAGATGAACTGACCAAGAACCAAGTGTCCCTCACTTGTCTCGTGAAGG
GATTCTACCCCTCCGATATCGCCGTGGAGTGGGAATCCAACGGGCAACCCGAGAACA
ACTACAAGACCACCCCTCCGGTGCTTGATTCCGATGGCTCCTTCTTCCTCTACTCCAA
GCTGACCGTGGACAAGTCAAGATGGCAGCAGGGGAACGTGTTCTCCTGCTCCGTCAT
GCACGAGGCCCTGCACAACCATTACACCCAGAAGTCTCTGTCGCTGAGCCCGGGAAA
ATAA SEQ ID NO: 24 DNA Sequence encoding the Heavy Chain of a melanin Humanized
Antibody (8C3-HE-VH3B-hIgG1)
ATGGACATGCGCGTGCCGGCACAACTGCTGGGCCTGCTGCTGCTTTGGCTGCGGGGA
GCTAGATGCGAAGTGCAGCTCGTCGAATCCGGAGGAGGACTGGTGCAGCCTGGCGG
AAGCATGCGCGTGTCATGCGCGGCTTCCGGATTCACCTTCTCGGACGCCTGGATGGA
TTGGGTCAGACAAGCGCCCGGCAAAGGCCTGGAATGGGTGGCCGAGATTCGGTCCA
AGGCCCATAACCACGCCACCTACTACGCCGACTCCGTGAAGGGGCGCTTTACTATCT
CCCGGGATAACTCGAAGAATACCGTGTACCTCCAGATGAACTCATTGAGGGCCGAGG
ACACTGGGGTCTACTACTGTACCCGCGGAGGCTACTACGGGAACTATGGTTTCTTCG
CCTACTGGGGCCAGGGTACCCTCGTGACTGTCAGCAGCGCCAGCACCAAGGGCCCCA
GCGTGTTCCCACTGGCCCCAAGCTCCAAGTCAACCTCCGGCGGAACTGCTGCGCTGG
GCTGCTTGGTGAAGGACTACTTCCCCGAACCGGTCACCGTGTCCTGGAACAGCGGAG
CCCTGACCTCGGGAGTCCACACTTTCCCCGCTGTGCTGCAGTCGTCCGGCCTGTACTC
GCTCTCGTCCGTGGTCACTGTCCCGTCCTCGTCCCTGGGTACTCAGACCTACATTTGC
AACGTCAACCACAAGCCTTCAAACACGAAAGTGGACAAGAAGGTCGAGCCGAAGTC
CTGCGACAAAACCCATACTTGCCCTCCTTGTCCGGCTCCCGAACTGCTGGGCGGACCT
TCCGTGTTCCTCTTCCCGCCTAAGCCGAAAGACACCCTGATGATCAGCAGGACTCCG
GAAGTGACATGCGTGGTGGTGGACGTGTCGCACGAGGACCCGGAGGTCAAGTTTAAT
TGGTACGTGGACGGAGTGGAAGTCCACAACGCCAAGACCAAGCCACGGGAAGAACA
GTACAATTCCACCTATCGCGTGGTGTCCGTGCTTACCGTGCTTCACCAAGACTGGCTG
AACGGAAAGGAGTACAAGTGCAAAGTGTCAAACAAAGCCCTGCCTGCCCCAATCGA
AAAGACCATCAGCAAGGCCAAGGGGCAGCCTCGGGAACCCCAAGTGTACACTCTCC
CGCCGTCAAGAGATGAACTGACCAAGAACCAAGTGTCCCTCACTTGTCTCGTGAAGG
GATTCTACCCCTCCGATATCGCCGTGGAGTGGGAATCCAACGGGCAACCCGAGAACA
ACTACAAGACCACCCCTCCGGTGCTTGATTCCGATGGCTCCTTCTTCCTCTACTCCAA
GCTGACCGTGGACAAGTCAAGATGGCAGCAGGGGAACGTGTTCTCCTGCTCCGTCAT
GCACGAGGCCCTGCACAACCATTACACCCAGAAGTCTCTGTCGCTGAGCCCGGGAAA
ATAA

TABLE 3B

Exemplary Melanin Antibody Expressing Plasmid Nucleotide Sequences

SEQ ID NO: 25 DNA Sequence of a plasmid encoding the Light Chain of a melanin Humanized Antibody (8C3-HE-VK4-hKappa)
TGCCGCAAAAAAGGGAATAAGGGCGACACGGAAATGTTGAATACTCATACTCTTCCT
TTTTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAAGTG
CCACCTGGGAAATTGTAAACGTTAATATTTTGTTAAAATTCGCGTTAAATTTTTGTTA
AATCAGCTCATTTTTTAACCAATAGGCCGAAATCGGCAAAATCCCTTATAAATCAAA
AGAATAGACCGAGATAGGGTTGAGTGTTGTTCCAGTTTGGAACAAGAGTCCACTATT
AAAGAACGTGGACTCCAACGTCAAAGGGCGAAAAACCGTCTATCAGGGCGATGGCC
CACTACGTGAACCATCACCCTAATCAAGTTTTTTGGGGTCGAGGTGCCGTAAAGCAC
TAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGG
CAAGTGTAGCGGTCACGCTGCGCGTAACCACCACACCCGCCGCGCTTAATGCGCCGC
TACAGGGCGCGTCCCATTCGCCATTCAGGCTGCGCAACTGTTGGGAAGGGCGATCGG
TGCGGGCCTCTTCGCTATTACGCCAGCTGGCGAAAGGGGGATGTGCTGCAAGGCGAT
TAAGTTGGGTAACGCCAGGGTTTTCCCAGTCACGACGTTGTAAAACGACGGCCAGTG
AGCGCGCGTAATACGACTCACTATAGGGCGAATTGGGTACCGGGCCCCCCCTCGAGG
TCGACGGTATCGATAAGCTTGATATCGAATTCGCTGGGCTGAGACCCGCAGAGGAAG
ACGCTCTAGGGATTTGTCCCGGACTAGCGAGATGGCAAGGCTGAGGACGGGAGGCT
GATTGAGAGGCGAAGGTACACCCTAATCTCAATACAACCCTTGGAGCTAAGCCAGCA
ATGGTAGAGGGAAGATTCTGCACGTCCCTTCCAGGCGGCCTCCCCGTCACCACCCAC
CCCAACCCGCCCCGACCGGAGCTGAGAGTAATTCATACAAAAGGACTCGCCCCTGCC
TTGGGGAATCCCAGGGACCGTCGTTAAACTCCCACTAACGTAGAACCCAGAGATCGC
TGCGTTCCCGCCCCCTCACCCGCCCGCTCTCGTCATCACTGAGGTGGAGAAGAGCAT
GCGTGAGGCTCCGGTGCCCGTCAGTGGGCAGAGCGCACATCGCCCACAGTCCCCGAG
AAGTTGGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGGGAGA
ACCGTATATAAGTGCAGTAGTCGCCGTGAACGTTCTTTTTCGCAACGGGTTTGCCGCC
AGAACACAGGTAAGTGCCGTGTGTGGTTCCCGCGGGCCTGGCCTCTTTACGGGTTAT
GGCCCTTGCGTGCCTTGAATTACTTCCACGCCCCTGGCTGCAGTACGTGATTCTTGAT
CCCGAGCTTCGGGTTGAAAGTGGGTGGGAGAGTTCGAGGCCTTGCGCTTAAGGAGCC
CCTTCGCCTCGTGCTTGAGTTGAGGCCTGGCTTGGGCGCTGGGGCCGCCGCGTGCGA
ATCTGGTGGCACCTTCGCGCCTATCTCGCTGCTTTCGATAAGTCTCTAGCCATTTAAA
ATTTTTGATGACCTGCTGCGACGCTTTTTTTCTGGCAAGATAGTCTTGTAAATGCGGG
CCAAGATCTGCACACTGGTATTTCGGTTTTTGGGGCGCGGGCGGCGACGGGGCCCG
TGCGTCCCAGCGCACATGTTCGGCGAGGCGGGGCCTGCGAGCGCGGCCACCGAGAA
TCGGACGGGGGTAGTCTCAAGCTGGCCGGCCTGCTCTGGTGCCTGGCCTCGCGCCGC
CGTGTATCGCCCCGCCCTGGGCGGCAAGGCTGGCCCGGTCGGCACCAGTTGCGTGAG
CGGAAAGATGGCCGCTTCCCGGCCCTGCTGCAGGGAGCTCAAAATGGAGGACGCGG
CGCTCGGGAGAGCGGGCGGGTGAGTCACCCACACAAAGGAAAAGGGCCTTTCCGTC
CTCAGCCGTCGCTTCATGTGACTCCACGGAGTACGGGCGCCGTCCAGGCACCTCGA
TTAGTTCTCGAGCTTTTGGAGTACGTCGTCTTTAGGTTGGGGGGAGGGGTTTTATGCG
ATGGAGTTTCCCCACACTGAGTGGGTGGAGACTGAAGTTAGGCCAGCTTGGCACTTG
ATGTAATTCTCCTTGGAATTTGCCCTTTTTGAGTTTGGATCTTGGTTCATTCTCAAGCC
TCAGACAGTGGTTCAAAGTTTTTTCCTTCCATTTCAGGTGTCGTGAAAACTACCCCTA
AAAGCCAAATCTAGAGCCACCATGGACATGAGAGTGCCGGCGCAACTGCTCGGCCT
GCTGTTGCTGTGGCTGAGGGGAGCCAGATGCGACATCGTGATGACTCAGTCACCCGA
TAGCCTTGCGGTGTCCCTCGGAGAACGCGCCACCATCAACTGTAAAGCCTCCGAATC
CGTGGACTCCTACGGCACCTCCTTCATGCACTGGTACCAGCAGAAGCCAGGACAGCC
TCCCAAGCTGTTGATCTATCTGGCCTCGAATCGGGAATCAGGAGTGCCGGACCGGTT
CAGCGGCTCCGGATCACGCACTGACTTCACGCTGACCATTAGCCCCGTGCAAGCAGA
GGACGTGGCGACCTACTACTGCCAGCAGAACAACGAATACCCTTACACTTTCGGCCA
GGGTACCAAGCTCGAAATCAAGCGGACAGTGGCAGCCCCATCGGTGTTCATTTTCCC
GCCGTCGGATGAGCAGCTCAAGTCCGGTACTGCCTCCGTGGTCTGCCTGCTGAACAA
CTTTTTACCCTCGCGAAGCGAAGGTCCAATGGAAAGTGGATAACGCCCTCCAGTCCGG
AAACTCCCAGGAGTCTGTCACCGAGCAGGACTCAAAGGACAGCACTTACTCCCTGTC
CTCGACTCTGACCCTGTCGAAGGCAGATTACGAGAAGCACAAAGTGTACGCCTGCGA
AGTGACCCATCAAGGCCTTTCCAGCCCGGTCACCAAGAGCTTCAATGGGGGGAGTG
TTAGTAATGAGGATCCCCCTATTCTATAGTGTCACCTAAATGCTAGAGCTCGCTGATC
AGCCTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAG
CAAGGGGGAGGATTGGGAAGACAATAGCAGGCATGCTGGGGATGCGGTGGGCTCTA
TGGCTTCTGAGGCGGAAAGAACCAGCTGGGGCTCGAGCGGCCGCCCCTTCTGAGGCG
GAAAGAACCAGCTGTGGAATGTGTGTCAGTTAGGGTGTGGAAAGTCCCCAGGCTCCC
CAGCAGGCAGAAGTATGCAAAGCATGCATCTCAATTAGTCAGCAACCAGGTGTGGA
AAGTCCCCAGGCTCCCCAGCAGGCAGAAGTATGCAAAGCATGCATCTCAATTAGTCA
GCAACCATAGTCCCGCCCCTAACTCCGCCCATCCCGCCCCTAACTCCGCCCAGTTCCG
CCCATTCTCCGCCCCATGGCTGACTAATTTTTTTTATTTATGCAGAGGCCGAGGCCGC
CTCGGCCTCTGAGCTATTCCAGAAGTAGTGAGGAGGCTTTTTTGGAGGCCTAGGCTTT
TGCAAAAAGCTAGCTTCCCGCTGCCATCATGGTTCGACCATTGAACTGCATCGTCG
CCGTGTCCCAAAATATGGGGATTGGCAAGAACGGAGACCTACCCTGGCCTCCGCTCA
GGAACGAGTTCAAGTACTTCCAAAGAATGACCACAACCTCTTCAGTGGAAGGTAAAC
AGAATCTGGTGATTATGGGTAGGAAAACCTGGTTCTCCATTCCTGAGAAGAATCGAC
CTTTAAAGGACAGAATTAATATAGTTCTCAGTAGAGAACTCAAAGAACCACCACGAG
GAGCTCATTTTCTTGCCAAAAGTTTGGATGATGCCTTAAGACTTATTGAACAACCGGA
ATTGGCAAGTAAAGTAGACATGGTTTGATAGTCGGAGGCAGTTCTGTTTACCAGGA
AGCCATGAATCAACCAGGCCACCTTAGACTCTTTGTGACAAGGATCATGCAGGAATT TABLE 3B-continued Exemplary Melanin Antibody Expressing Plasmid Nucleotide Sequences TGAAAGTGACACGTTTTTCCCAGAAATTGATTTGGGGAAATATAAACTTCTCCCAGA
ATACCCAGGCGTCCTCTCTGAGGTCCAGGAGGAAAAAGGCATCAAGTATAAGTTTGA
AGTCTACGAGAAGAAAGACTAACAGGAAGATGCTTTCAAGTTCTCTGCTCCCCTCCT
AAAGCTATGCATTTTTATAAGACCATGGGACTTTTGCTGGCTTTAGATCCCGCGGAGA
TCCAGACATGATAAGATACATTGATGAGTTTGGACAAACCACAACTAGAATGCAGTG
AAAAAAATGCTTTATTTGTGAAATTTGTGATGCTATTGCTTTATTTGTAACCATTATA
AGCTGCAATAAACAAGTTAACAACAACAATTGCATTCATTTTATGTTTCAGGTTCAG
GGGGAGGTGTGGGAGGTTTTTTAAAGCAAGTAAAACCTCTACAAATGTGGTATGGCT
GATTATGAGCTCCAGCTTTTGTTCCCTTTAGTGAGGGTTAATTGCGCGCTTGGCGTAA
TCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTG
CTGGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCTGG
AAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGGTCTGA
CGCTCAGTGGAACGAAAACTCACGTTAAGGGATTTTGGTCATGAGATTATCAAAAAG
GATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCA
GCGATCTGTCTATTTCGTTCATCCATAGTTGCCTGACTCCCCGTCGTGTAGATAACTA
CGATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAG
TTCGATGTAACCCACTCGTGCACCCAACTGATCTTCAGCATCTTTTACTTTCACCAGC
GTTTCTGGGTGAGCAAAAACAGGAAGGCAAAA SEQ ID NO: 26 DNA Sequence of a plasmid encoding the Light Chain of a melanin
Humanized Antibody (8C3-HE-VK1A-hKappa)
CGGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GTGAGCGCGCGTAATACGACTCACTATAGGGCGAATTGGGTACCGGGCCCCCCCTCG
AGGTCGACGGTATCGATAAGCTTGATATCGAATTCGCTGGGCTGAGACCCGCAGAGG
AAGACGCTCTAGGGATTTGTCCCGGACTAGCGAGATGGCAAGGCTGAGGACGGGAG
GCTGATTGAGAGGCGAAGGTACACCCTAATCTCAATACAACCCTTGGAGCTAAGCCA
GCAATGGTAGAGGGAAGATTCTGCACGTCCCTTCCAGGCGGCCTCCCCGTCACCACC
CACCCCAACCCGCCCCGACCGGAGCTGAGAGTAATTCATACAAAAGGACTCGCCCCT
GCCTTGGGGAATCCAGGGACCGTCGTTAAACTCCCACTAACGTAGAACCCAGAGAT
CGCTGCGTTCCCGCCCCCTCACCCGCCCGCTCTCGTCATCACTGAGGTGGAGAAGAG
CATGCGTGAGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGG
AGAACCGTATATAAGTGCAGTAGTCGCCGTGAACGTTCTTTTTCGCAACGGGTTTGCC
GCCAGAACACAGGTAAGTGCCGTGTGTGGTTCCCGCGGGCCTGGCCTCTTTACGGGT
TATGGCCCTTGCGTGCCTTGAATTACTTCCACGCCCCTGGCTGCAGTACGTGATTCTT
GATCCCGAGCTTCGGGTTGGAAGTGGGTGGGAGAGTTCGAGGCCTTGCGCTTAAGGA
GCCCCTTCGCCTCGTGCTTGAGTTGAGGCCTGGCTTGGGCGCTGGGGCCGCCGCGTG
CGAATCTGGTGGCACCTTCGCGCCTATCTCGCTGCTTTCGATAAGTCTCTAGCCATTT
AAAATTTTTGATGACCTGCTGCGACGCTTTTTTTCTGGCAAGATAGTCTTGTAAATGC
GGGCCAAGATCTGCACACTGGTATTTCGGTTTTTGGGGCCGCGGGCGGCGACGGGGC
CCGTGCGTCCCAGCGCACATGTTCGGCGAGGCGGGGCCTGCGAGCGCGGCCACCGA
GAATCGGACGGGGGTAGTCTCAAGCTGGCCGGCCTGCTCTGGTGCCTGGCCTCGCGC
CGCCGTGTATCGCCCCGCCCTGGGCGGCAAGGCTGGCCCGGTCGGCACCAGTTGCGT
GAGCGGAAAGATGGCCGCTTCCCGGCCCTGCTGCAGGGAGCTCAAAATGGAGGACG
CGGCGCTCGGGAGAGCGGGCGGGTGAGTCACCCACACAAAGGAAAAGGGCCTTTCC
GTCCTCAGCCGTCGCTTCATGTGACTCCACGGAGTACCGGGCGCCGTCCAGGCACCT
CGATTAGTTCTCGAGCTTTTGGAGTACGTCGTCTTTAGGTTGGGGGGAGGGGTTTTAT
GCGATGGAGTTTCCCCACACTGAGTGGGTGGAGACTGAAGTTAGGCCAGCTTGGCAC
TTGATGTAATTCTCCTTGGAATTTGCCCTTTTTGAGTTTGGATCTTGGTTCATTCTCAA
GCCTCAGACAGTGGTTCAAAGTTTTTTCCTTCCATTTCAGGTGTCGTGAAAACTACCC TABLE 3B-continued Exemplary Melanin Antibody Expressing Plasmid Nucleotide Sequences

```
CTAAAAGCCAAATCTAGAGCCACCATGGACATGAGAGTGCCGGCGCAACTGCTCGG
CCTGCTGTTGCTGTGGCTGAGGGGAGCCAGATGCGACATCCAGATGACTCAGTCACC
CTCGAGCCTTAGCGTGTCCCTCGGAGATCGCGCCACCATCACCTGTCGGGCCTCCGA
ATCCGTGGACTCCTACGGCACCTCCTTCATGCACTGGTACCAGCAGAAGCCAGGAAA
GCCTCCCAAGCTGTTGATCTATCTGGCCTCGAATCTGGAATCAGGAGTGCCGTCGCG
GTTCAGCGGCTCCGGATCACGCACTGACTTCACGCTGACCATTAGCCCCGTGCAAGC
AGAGGACTTTGCGACCTACTACTGCCAGCAGAACAACGAATACCCTTACACTTTCGG
CCAGGGTACCAAGCTCGAAATCAAGCGGACAGTGGCAGCCCCATCGGTGTTCATTTT
CCCGCCGTCGGATGAGCAGCTCAAGTCCGGTACTGCCTCCGTGGTCTGCCTGCTGAA
CAACTTTTACCCTCGCGAAGCGAAGGTCCAATGGAAAGTGGATAACGCCCTCCAGTC
CGGAAACTCCCAGGAGTCTGTCACCGAGCAGGACTCAAAGGACAGCACTTACTCCCT
GTCCTCGACTCTGACCCTGTCGAAGGCAGATTACGAGAAGCACAAAGTGTACGCCTG
CGAAGTGACCCATCAAGGCCTTTCCAGCCCGGTCACCAAGAGCTTCAATCGGGGGGA
GTGTTAGTAATGAGGATCCCCCTATTCTATAGTGTCACCTAAATGCTAGAGCTCGCTG
ATCAGCCTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAA
TTGCATCGCATTGTCTGAGTAGGTGTCATTCTATTCTGGGGGGTGGGGTGGGGCAGG
ACAGCAAGGGGGAGGATTGGGAAGACAATAGCAGGCATGCTGGGGATGCGGTGGGC
TCTATGGCTTCTGAGGCGGAAAGAACCAGCTGGGGCTCGAGCGGCCGCCCCTTCTGA
GGCGGAAAGAACCAGCTGTGGAATGTGTGTCAGTTAGGGTGTGGAAAGTCCCCAGG
CTCCCCAGCAGGCAGAAGTATGCAAAGCATGCATCTCAATTAGTCAGCAACCAGGTG
TGGAAAGTCCCCAGGCTCCCCAGCAGGCAGAAGTATGCAAAGCATGCATCTCAATTA
GTCAGCAACCATAGTCCCGCCCCTAACTCCGCCCATCCCGCCCCTAACTCCGCCCAGT
TCCGCCCATTCTCCGCCCCATGGCTGACTAATTTTTTTTATTTATGCAGAGGCCGAGG
CCGCCTCGGCCTCTGAGCTATTCCAGAAGTAGTGAGGAGGCTTTTTTGGAGGCCTAG
GCTTTTGCAAAAAAGCTAGCTTCCCGCTGCCATCATGGTTCGACCATTGAACTGCATC
GTCGCCGTGTCCCAAAATATGGGGATTGGCAAGAACGGAGACCTACCCTGGCCTCCG
CTCAGGAACGAGTTCAAGTACTTCCAAAGAATGACCACAACCTCTTCAGTGGAAGGT
AAACAGAATCTGGTGATTATGGGTAGGAAAACCTGGTTCTCCATTCCTGAGAAGAAT
CGACCTTTAAAGGACAGAATTAATATAGTTCTCAGTAGAGAACTCAAAGAACCACCA
CGAGGAGCTCATTTTCTTGCCAAAAGTTTGGATGATGCCTTAAGACTTATTGAACAAC
CGGAATTGGCAAGTAAAGTAGACATGGTTTGGATAGTCGGAGGCAGTTCTGTTTACC
AGGAAGCCATGAATCAACCAGGCCACCTTAGACTCTTTGTGACAAGGATCATGCAGG
AATTTGAAAGTGACACGTTTTTCCCAGAAATTGATTTGGGGAAATATAAACTTCTCCC
AGAATACCCAGGCGTCCTCTCTGAGGTCCAGGAGGAAAAAGGCATCAAGTATAAGTT
TGAAGTCTACGAGAAGAAAGACTAACAGGAAGATGCTTTCAAGTTCTCTGCTCCCCT
CCTAAAGCTATGCATTTTTATAAGACCATGGGACTTTTGCTGGCTTTAGATCCCGCGG
AGATCCAGACATGATAAGATACATTGATGAGTTTGGACAAACCACAACTAGAATGCA
GTGAAAAAAATGCTTTATTTGTGAAATTTGTGATGCTATTGCTTTATTTGTAACCATT
ATAAGCTGCAATAAACAAGTTAACAACAACAATTGCATTCATTTTTATGTTTCAGGTTC
AGGGGGAGGTGTGGGAGGTTTTTTAAAGCAAGTAAAACCTCTACAAATGTGGTATGG
CTGATTATGAGCTCCAGCTTTTGTTCCCTTTAGTGAGGGTTAATTGCGCGCTTGGCGT
AATCATGGTCATAGCTGTTTCCTGTGTGAAATTGTTATCCGCTCACAATTCCACACAA
CATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCA
GCTGCATTAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGATAACT
ACGATACGGGAGGGCTTACCATCTGGCCCCAGTGCTGCAATGATACCGCGAGACCCA
CGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAG
TTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGC
GACACGGAAATGTTGAATACTCATACTCTTCCTTTTTCAATATTATTGAAGCATTTAT
```

TABLE 3B-continued

Exemplary Melanin Antibody Expressing Plasmid Nucleotide Sequences

CAGGGTTATTGTCTCATGAGCGGATACATATTTGAATGTATTTAGAAAAATAAACAA
ATAGGGGTTCCGCGCACATTTCCCCGAAAAGTGCCACCTGGGAAATTGTAAACGTTA
ATATTTTGTTAAAATTCGCGTTAAATTTTTGTTAAATCAGCTCATTTTTTAACCAATAG
GCCGAAATCGGCAAATCCCTTATAAATCAAAAGAATAGACCGAGATAGGGTTGAG
TGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATC
AAGTTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGAAGA
AAGCGAAAGGAGCGGGCGCTAGGGCGCTGGCAAGTGTAGCGGTCACGCTGCGCGTA
ACCACCACACCCGCCGCGCTTAATGCGCCGCTACAGGGCGCGTCCCATTCGCCATTC
AGGCTGCGCAACTGTTGGGAAGGGCGAT

SEQ ID NO: 27 DNA Sequence of a plasmid encoding the Light Chain of a melanin
Humanized Antibody (8C3-HE-VK1B-hKappa)
CGGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GTGAGCGCGCGTAATACGACTCACTATAGGGCGAATTGGGTACCGGGCCCCCCCTCG
AGGTCGACGGTATCGATAAGCTTGATATCGAATTCGCTGGGCTGAGACCCGCAGAGG
AAGACGCTCTAGGGATTTGTCCCGGACTAGCGAGATGGCAAGGCTGAGGACGGGAG
GCTGATTGAGAGGCGAAGGTACACCCTAATCTCAATACAACCCTTGGAGCTAAGCCA
GCAATGGTAGAGGGAAGATTCTGCACGTCCCTTCCAGGCGGCCTCCCCGTCACCACC
CACCCCAACCCGCCCCGACCGGAGCTGAGAGTAATTCATACAAAAGGACTCGCCCCT
GCCTTGGGGAATCCCAGGGACGTCGTTAAACTCCCACTAACGTAGAACCCAGAGAT
CGCTGCGTTCCCGCCCCCTCACCCGCCCGCTCTCGTCATCACTGAGGTGGAGAAGAG
CATGCGTGAGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGG
AGAACCGTATATAAGTGCAGTAGTCGCCGTGAACGTTCTTTTTCGCAACGGGTTTGCC
GCCAGAACACAGGTAAGTGCCGTGTGTGGTTCCCGCGGGCCTGGCCTCTTTACGGGT
TATGGCCCTTGCGTGCCTTGAATTACTTCCACGCCCCTGGCTGCAGTACGTGATTCTT
GATCCCGAGCTTCGGGTTGAAAGTGGGTGGGAGAGTTCGAGGGCCTTGCGCTTAAGGA
GCCCCTTCGCCTCGTGCTTGAGTTGAGGCCTGGCTTGGGCGCTGGGGCGCCGCGTG
CGAATCTGGTGGCACCTTCGCGCCTATCTCGCTGCTTTCGATAAGTCTCTAGCCATTT
AAAATTTTTGATGACCTGCTGCGACGCTTTTTTTCTGGCAAGATAGTCTTGTAAATGC
GGGCCAAGATCTGCACACTGGTATTTCGGTTTTTGGGGCCGGGGCGGCGACGGGGC
CCGTGCGTCCCAGCGCACATGTTCGGCGAGGCGGGGCCTGCGAGCGCGGCCACCGA
GAATCGGACGGGGGTAGTCTCAAGCTGGCCGGCCTGCTCTGGTGCCTGGCCTCGCGC
CGCCGTGTATCGCCCCGCCCTGGGCGGCAAGGCTGGCCCGGTCGGCACCAGTTGCGT
GAGCGGAAAGATGGCCGCTTCCCGGCCCTGCTGCAGGGAGCTCAAAATGGAGGACG
CGGCGCTCGGGAGAGCGGGCGGGTGAGTCACCCACACAAAGGAAAAGGGCCTTTCC
GTCCTCAGCCGTCGCTTCATGTGACTCCACGGAGTACCGGGCGCCGTCCAGGCACCT
CGATTAGTTCTCGAGCTTTTGGAGTACGTCGTCTTTAGGTTGGGGGGAGGGGTTTTAT
GCGATGGAGTTTCCCCACACTGAGTGGGTGGAGACTGAAGTTAGGCCAGCTTGGCAC
TTGATGTAATTCTCCTTGGAATTTGCCCTTTTTGAGTTTGGATCTTGGTTCATTCTCAA
GCCTCAGACAGTGGTTCAAAGTTTTTTCCTTCCATTTCAGGTGTCGTGAAAACTACCC
CTAAAAGCCAAATCTAGAGCCACCATGGACATGAGAGTGCCGGCGCAACTGCTCGG
CCTGCTGTTGCTGTGGCTGAGGGGAGCCAGATGCGACATCCAGATGACTCAGTCACC
CTCGAGCCTTAGCGTGTCCGTGGGAGATCGCGCCACCATCACCTGTCGGGCCTCCGA
ATCCGTGGACTCCTACGGCACCTCCTTCATGCACTGGTACCAGCAGAAGCCAGGAAA
GCCTCCCAAGCTGTTGATCTATCTGGCCTCGAATCTGCAGTCAGGAGTGCCGTCGCG
GTTCAGCGGCTCCGGATCACGCACTGACTTCACGCTGACCATTAGCCCCGTGCAAGC
AGAGGACTTTGCGACCTACTACTGCCAGCAGAACAACGAATACCCTTACACTTTCGG
CCAGGGTACCAAGCTCGAAATCAAGCGGACAGTGGCAGCCCCATCGGTGTTCATTTT
CCCGCCGTCGGATGAGCAGCTCAAGTCCGGTACTGCCTCCGTGGTCTGCCTGCTGAA
CAACTTTTACCCTCGCGAAGCGAAGGTCCAATGGAAAGTGGATAACGCCCTCCAGTC
CGGAAACTCCCAGGAGTCTGTCACCGAGCAGGACTCAAAGGACAGCACTTACTCCCT
GTCCTCGACTCTGACCCTGTCGAAGGCAGATTACGAGAAGCACAAAGTGTACGCCTG
CGAAGTGACCCATCAAGGCCTTTCCAGCCCGGTCACCAAGAGCTTCAATCGGGGGGA
GTGTTAGTAATGAGGATCCCCCTATTCTATAGTGTCACCTAAATGCTAGAGCTCGCTG
ATCAGCCTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAA
TTGCATCGCATTGTCTGAGTAGGTGTCATTCTATTCTGGGGGGTGGGGTGGGGCAGG
ACAGCAAGGGGGAGGATTGGGAAGACAATAGCAGGCATGCTGGGGATGCGGTGGGC
TCTATGGCTTCTGAGGCGGAAAGAACCAGCTGGGGCTCGAGCGGCCGCCCCTTCTGA
GGCGGAAAGAACCAGCTGTGGAATGTGTGTCAGTTAGGGTGTGGAAAGTCCCCAGG
CTCCCCAGCAGGCAGAAGTATGCAAAGCATGCATCTCAATTAGTCAGCAACCAGGTG
TGGAAAGTCCCCAGGCTCCCCAGCAGGCAGAAGTATGCAAAGCATGCATCTCAATTA
GTCAGCAACCATAGTCCCGCCCCTAACTCCGCCCATCCCGCCCCTAACTCCGCCCAGT
TCCGCCCATTCTCCGCCCCATGGCTGACTAATTTTTTTTATTTATGCAGAGGCCGAGG
CCGCCTCGGCCTCTGAGCTATTCCAGAAGTAGTGAGGAGGCTTTTTTGGAGGCCTAG
GCTTTTGCAAAAAGCTAGCTTCCCGCTGCCATCATGGTTCGACCATTGAACTGCATC
GTCGCCGTGTCCCAAAATATGGGGATTGGCAAGAACGGAGACCTACCCTGGCCTCCG
CTCAGGAACGAGTTCAAGTACTTCCAAAGAATGACCACAACCTCTTCAGTGGAAGGT
AAACAGAATCTGGTGATTATGGGTAGGAAAACCTGGTTCTCCATTCCTGAGAAGAAT
CGACCTTTAAAGGACAGAATTAATATAGTTCTCAGTAGAAGAACTCAAAGAACCACCA
CGAGGAGCTCATTTTCTTGCCAAAAGTTTGGATGATGCCTTAAGACTTATTGAACAAC
CGGAATTGGCAAGTAAAGTAGACATGGTTTGGATAGTCGGAGGCAGTTCTGTTTACC
AGGAAGCCATGAATCAACCAGGCCACCTTAGACTCTTTGTGACAAGGATCATGCAGG TABLE 3B-continued Exemplary Melanin Antibody Expressing Plasmid Nucleotide Sequences AATTTGAAAGTGACACGTTTTTCCCAGAAATTGATTTGGGGAAATATAAACTTCTCCC
AGAATACCCAGGCGTCCTCTCTGAGGTCCAGGAGGAAAAAGGCATCAAGTATAAGTT
TGAAGTCTACGAGAAGAAAGACTAACAGGAAGATGCTTTCAAGTTCTCTGCTCCCCT
CCTAAAGCTATGCATTTTTATAAGACCATGGGACTTTTGCTGGCTTTAGATCCCGCGG
AGATCCAGACATGATAAGATACATTGATGAGTTTGGACAAACCACAACTAGAATGCA
GTGAAAAAAATGCTTTATTTGTGAAATTTGTGATGCTATTGCTTTATTTGTAACCATT
ATAAGCTGCAATAAACAAGTTAACAACAACAATTGCATTCATTTTATGTTTCAGGTTC
AGGGGGAGGTGTGGGAGGTTTTTTAAAGCAAGTAAAACCTCTACAAATGTGGTATGG
CTGATTATGAGCTCCAGCTTTTGTTCCCTTTAGTGAGGGTTAATTGCGCGCTTGGCGT
AATCATGGTCATAGCTGTTTCCTGTGTGAAATTGTTATCCGCTCACAATTCCACACAA
CATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCA
GCTGCATTAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGA
TTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGATAACT
ACGATACGGGAGGGCTTACCATCTGGCCCCAGTGCTGCAATGATACCGCGAGACCCA
CGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAG
TTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGC
GACACGGAAATGTTGAATACTCATACTCTTCCTTTTTCAATATTATTGAAGCATTTAT
CAGGGTTATTGTCTCATGAGCGGATACATATTTGAATGTATTTAGAAAAATAAACAA
ATAGGGGTTCCGCGCACATTTCCCCGAAAAGTGCCACCTGGGAAATTGTAAACGTTA
ATATTTTGTTAAAATTCGCGTTAAATTTTTGTTAAATCAGCTCATTTTTTAACCAATAG
GCCGAAATCGGCAAAATCCCTTATAAATCAAAAGAATAGACCGAGATAGGGTTGAG
TGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATC
AAGTTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGAAGA
AAGCGAAAGGAGCGGGCGCTAGGGCGCTGGCAAGTGTAGCGGTCACGCTGCGCGTA
ACCACCACACCCGCCGCGCTTAATGCGCCGCTACAGGGCGCGTCCCATTCGCCATTC
AGGCTGCGCAACTGTTGGGAAGGGCGAT SEQ ID NO: 28 DNA Sequence of a plasmid encoding the Heavy Chain of a melanin Humanized Antibody (8C3-HE-VH3A-hIgG1
CGGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GTGAGCGCGCGTAATACGACTCACTATAGGGCGAATTGGGTACCGGGCCCCCCCTCG
AGGTCGACGGTATCGATAAGCTTGATATCGAATTCGCTGGGCTGAGACCCGCAGAGG
AAGACGCTCTAGGGATTGTCCCGGACTAGCGAGATGGCAAGGCTGAGGACGGGAG
GCTGATTGAGAGGCGAAGGTACACCCTAATCTCAATACAACCCTTGGAGCTAAGCCA
GCAATGGTAGAGGGAAGATTCTGCACGTCCCTTCCAGGCGGCCTCCCCGTCACCACC
CACCCCAACCCGCCCCGACCGGAGCTGAGAGTAATTCATACAAAAGGACTCGCCCCT
GCCTTGGGGAATCCCAGGGACCGTCGTTAAACTCCCACTAACGTAGAACCCAGAGAT
CGCTGCGTTCCCGCCCCCTCACCCGCCCGCTCTCGTCATCACTGAGGTGGAGAAGAG
CATGCGTGAGGCTCCGGTGCCCGTCAGTGGGCAGAGCGCACATCGCCCACAGTCCCC
GAGAAGTTGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGG
AGAACCGTATATAAGTGCAGTAGTCGCCGTGAACGTTCTTTTTCGCAACGGGTTTGCC
GCCAGAACACAGGTAAGTGCCGTGTGTGGTTCCCGCGGGCCTGGCCTCTTTACGGGT
TATGGCCTTGCGTGCCTTGAATTACTTCCACGCCCCTGGCTGCAGTACGTGATTCTT
GATCCCGAGCTTCGGGTTGAAAGTGGGTGGGAGAAGTTCGAGGCCTTGCGCTTAAGGA
GCCCCTTCGCCTCGTGCTTGAGTTGAGGCCTGGCTTGGGCGCTGGGGCCGCCGCGTG
CGAATCTGGTGGCACCTTCGCGCCTATCTCGCTGCTTTCGATAAGTCTCTAGCCATTT TABLE 3B-continued Exemplary Melanin Antibody Expressing Plasmid Nucleotide Sequences

```
AAAATTTTTGATGACCTGCTGCGACGCTTTTTTTCTGGCAAGATAGTCTTGTAAATGC
GGGCCAAGATCTGCACACTGGTATTTCGGTTTTTGGGGCCGCGGGCGGCGACGGGGC
CCGTGCGTCCCAGCGCACATGTTCGGCGAGGCGGGGCCTGCGAGCGCGGCCACCGA
GAATCGGACGGGGGTAGTCTCAAGCTGGCCGGCCTGCTCTGGTGCCTGGCCTCGCGC
CGCCGTGTATCGCCCCGCCCTGGGCGGCAAGGCTGGCCCGGTCGGCACCAGTTGCGT
GAGCGGAAAGATGGCCGCTTCCCGGCCCTGCTGCAGGGAGCTCAAAATGGAGGACG
CGGCGCTCGGGAGAGCGGGCGGGTGAGTCACCCACACAAAGGAAAAGGGCCTTTCC
GTCCTCAGCCGTCGCTTCATGTGACTCCACGGAGTACCGGGCGCCGTCCAGGCACCT
CGATTAGTTCTCGAGCTTTTGGAGTACGTCGTCTTTAGGTTGGGGGGAGGGGTTTTAT
GCGATGGAGTTTCCCCACACTGAGTGGGTGGAGACTGAAGTTAGGCCAGCTTGGCAC
TTGATGTAATTCTCCTTGGAATTTGCCCTTTTTGAGTTTGGATCTTGGTTCATTCTCAA
GCCTCAGACAGTGGTTCAAAGTTTTTTCCTTCCATTTCAGGTGTCGTGAAAACTACCC
CTAAAAGCCAAATCTAGAGCCACCATGGACATGCGCGTGCCGGCACAACTGCTGGGC
CTGCTGCTGCTTTGGCTGCGGGGAGCTAGATGCGAAGTGCAGCTCGTCGAATCCGGA
GGAGGACTGGTGCAGCCTGGCGGAAGCATGCGCGTGTCATGCGCGGCTTCCGGATTC
ACCTTCTCGGACGCCTGGATGGATTGGGTCAGACAAGCGCCCGGCAAAGGCCTGGAA
TGGGTGGCCGAGATTCGGTCCAAGGCCCATAACCACGCCACCTACTACGCCGAGTCC
GTGAAGGGGCGCTTTACTATCTCCCGGGATGACTCGAAGTCGACGGTGTACCTCCAG
ATGAACTCATTGAGGGCCGAGGACACTGGGACCTACTACTGTACCCGCGGAGGCTAC
TACGGGAACTATGGTTCTTCGCCTACTGGGGCCAGGGTACCCTCGTGACTGTCAGC
AGCGCCAGCACCAAGGGCCCCAGCGTGTTCCCACTGGCCCCAAGCTCCAAGTCAACC
TCCGGCGGAACTGCTGCGCTGGGCTGCTTGGTGAAGGACTACTTCCCCGAACCGGTC
ACCGTGTCCTGGAACAGCGGAGCCCTGACCTCGGGAGTCCACACTTTCCCCGCTGTG
CTGCAGTCGTCCGCCTGTACTCGCTCTCGTCCGTGGTCACTGTCCCGTCCTCGTCCC
TGGGTACTCAGACCTACATTTGCAACGTCAACCACAAGCCTTCAAACACGAAAGTGG
ACAAGAAGGTCGAGCCGAAGTCCTGCGACAAAACCCATACTTGCCCTCCTTGTCCGG
CTCCCGAACTGCTGGGCGGACCTTCCGTGTTCCTCTTCCCGCCTAAGCCGAAAGACAC
CCTGATGATCAGCAGGACTCCGGAAGTGACATGCGTGGTGGTGGACGTGTCGCACGA
GGACCCGGAGGTCAAGTTTAATTGGTACGTGGACGGAGTGGAAGTCCACAACGCCA
AGACCAAGCCACGGGAAGAACAGTACAATTCCACCTATCGCGTGGTGTCCGTGCTTA
CCGTGCTTCACCAAGACTGGCTGAACGGAAAGGAGTACAAGTGCAAAGTGTCAAAC
AAAGCCCTGCCTGCCCCAATCGAAAAGACCATCAGCAAGGCCAAGGGGCAGCCTCG
GGAACCCCAAGTGTACACTCTCCCGCCGTCAAGAGATGAACTGACCAAGAACCAAGT
GTCCCTCACTTGTCTCGTGAAGGGATTCTACCCCTCCGATATCGCCGTGGAGTGGGAA
TCCAACGGGCAACCCGAGAACAACTACAAGACCACCCCTCCGGTGCTTGATTCCGAT
GGCTCCTTCTTCCTCTACTCCAAGCTGACCGTGGACAAGTCAAGATGGCAGCAGGGG
AACGTGTTCTCCTGCTCCGTCATGCACGAGGCCCTGCACAACCATTACACCCAGAAG
TCTCTGTCGCTGAGCCCGGGAAAATAATGAGGATCCCCCTATTCTATAGTGTCACCTA
AATGCTAGAGCTCGCTGATCAGCCTCGACTGTGCCTTCTAGTTGCCAGCCATCTGTTG
TTTGCCCCTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGG
GGTGGGGTGGGGCAGGACAGCAAGGGGGAGGATTGGGAAGACAATAGCAGGCATG
CTGGGGATGCGGTGGGCTCTATGGCTTCTGAGGCGGAAAGAACCAGCTGGGGCTCGA
GCGGCCGCAGATTGTACCTTCTGAGGCGGAAAGAACCAGCTGTGGAATGTGTGTCAG
TTAGGGTGTGGAAAGTCCCCAGGCTCCCCAGCAGGCAGAAGTATGCAAAGCATGCAT
CTCAATTAGTCAGCAACCAGGTGTGGAAAGTCCCCAGGCTCCCCAGCAGGCAGAAGT
ATGCAAAGCATGCATCTCAATTAGTCAGCAACCATAGTCCCGCCCCTAACTCCGCCC
ATCCCGCCCCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAGAAGTAGTG
AGGAGGCTTTTTTGGAGGCCTAGGCTTTTGCAAAAAGCTTACCATGATTGAACAAGA
TGGATTGCACGCAGGTTCTCCGGCCGCTTGGGTGGAGAGGCTATTCGGCTATGACTG
GGCACAACAGACAATCGGCTGCTCTGATGCCGCCGTGTTCCGGCTGTCAGCGCAGGG
GCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCGGGGC
AGGATCTCCTGTCATCTCACCTTGCTCCTGCCGAGAAAGTATCCATCATGGCTGATGC
AATGCGGCGGCTGCATACGCTTGATCCGGCTACCTGCCCATTCGACCACCAAGCGAA
ACATCGCATCGAGCGAGCACGTACTCGGATGGAAGCCGGTCTTGTCGATCAGGATGA
TCTGGACGAAGAGCATCAGGGGCTCGCGCCAGCCGAACTGTTCGCCAGGCTCAAGGC
GCGCATGCCCGACGGCGAGGATCTCGTCGTGACCCATGGCGATGCCTGCTTGCCGAA
TATCATGGTGGAAAATGGCCGCTTTTCTGGATTCATCGACTGTGGCCGGCTGGGTGTG
GCGGACCGCTATCAGGACATAGCGTTGGCTACCCGTGATATTGCTGAAGAGCTTGGC
GGCGAATGGGCTGACCGCTTCCTCGTGCTTTACGGTATCGCCGCTCCCGATTCGCAGC
GCATCGCCTTCTATCGCCTTCTTGACGAGTTCTTCTGAGGGATCGCGGAGATCCAGAC
ATGATAAGATACATTGATGAGTTTGGACAAACCACAACTAGAATGCAGTGAAAAAA
ATGCTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGAGG
TGTGGGAGGTTTTTTAAAGCAAGTAAAACCTCTACAAATGTGGTATGGCTGATTATG
AGCTCCAGCTTTTGTTCCCTTTAGTGAGGGTTAATTGCGCGCTTGGCGTAATCATGGT
CATAGCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAA
TGAATCGGCCAACGCGCGGGGAGAGGCGGTTTGCGTATTGGGCGCTCTTCCGCTTCC
TCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACAPS
TGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCT
```

TABLE 3B-continued

Exemplary Melanin Antibody Expressing Plasmid Nucleotide Sequences

CGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTG
CGCTCTGCTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAA
ACTTGGTCTGACAGTTACCAATGCTTAATCAGTGAGGCACCTATCTCAGCGATCTGTC
TATTTCGTTCATCCATAGTTGCCTGACTCCCCGTCGTGTAGATAACTACGATACGGGA
GGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAG
TTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAA
TTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATA
CGGGATAATACCGCGCCACATAGCAGAACTTTAAAAGTGCTCATCATTGGAAAACGT
TCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTC
CGCGCACATTTCCCCGAAAAGTGCCACCTGGGAAATTGTAAACGTTAATATTTTGTTA
AAATTCGCGTTAAATTTTTGTTAAATCAGCTCATTTTTTAACCAATAGGCCGAAATCG
GCAAAATCCCTTATAAATCAAAAGAATAGACCGAGATAGGGTTGAGTGTTGTTCCAG
TTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGG
GGTCGAGGTGCCGTAAAGCACTAAATCGGAACCCTAAAGGGAGCCCCCGATTTAGA
GCTTGACGGGGAAAGCCGGCGAACGTGGCGAGAAAGGAAGGGAAGAAAGCGAAAG
GAGCGGGCGCTAGGGCGCTGGCAAGTGTAGCGGTCACGCTGCGCGTAACCACCACA
CCCGCCGCGCTTAATGCGCCGCTACAGGGCGCGTCCCATTCGCCATTCAGGCTGCGC
AACTGTTGGGAAGGGCGAT

SEQ ID NO: 29 DNA Sequence of a plasmid encoding the Heavy Chain of a melanin
Humanized Antibody (8C3-HE-VH3B-hIgG1)
CGGTGCGGGCCTCTTCGCTATTACGCCAGCTGGCGAAAGGGGGATGTGCTGCAAGGC
GATTAAGTTGGGTAACGCCAGGGTTTTCCCAGTCACGACGTTGTAAAACGACGGCCA
GTGAGCGCGCGTAATACGACTCACTATAGGGCGAATTGGGTACCGGGCCCCCCCTCG
AGGTCGACGGTATCGATAAGCTTGATATCGAATTCGCTGGGCTGAGACCCGCAGAGG
AAGACGCTCTAGGGATTTGTCCCGGACTAGCGAGATGGCAAGGCTGAGGACGGGAG
GCTGATTGAGAGGCGAAGGTACACCCTAATCTCAATACAACCCTTGGAGCTAAGCCA
GCAATGGTAGAGGGAAGATTCTGCACGTCCCTTCCAGGCGGCCTCCCCGTCACCACC
CACCCCAACCCGCCCCGACCGGAGCTGAGAGTAATTCATACAAAAGGACTCGCCCCT
GCCTTGGGGAATCCCAGGGACCGTCGTTAAACTCCCACTAACGTAGAACCCAGAGAT
CGCTGCGTTCCCGCCCCCTCACCCGCCCGCTCTCGTCATCACTGAGGTGGAGAAGAG
CATGCGTGAGGCTCCGGTGCCCGTCAGTGGGCAGAGCGCACATCGCCCACAGTCCCC
GAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGG
AGAACCGTATATAAGTGCAGTAGTCGCCGTGAACGTTCTTTTTCGCAACGGGTTTGCC
GCCAGAACACAGGTAAGTGCCGTGTGTGGTTCCCGCGGGCCTGGCCTCTTTACGGGT
TATGGCCCTTGCGTGCCTTGAATTACTTCCACGCCCCTGGCTGCAGTACGTGATTCTT
GATCCCGAGCTTCGGGTTGAAAGTGGGTGGGAGAGTTCGAGGCCTTGCGCTTAAGGA
GCCCCTTCGCCTCGTGCTTGAGTTGAGGCCTGGCTTGGGCGCTGGGGCCGCCGCGTG
CGAATCTGGTGGCACCTTCGCGCCTATCTCGCTGCTTTCGATAAGTCTCTAGCCATTT
AAAATTTTTGATGACCTGCTGCGACGCTTTTTTTCTGGCAAGATAGTCTTGTAAATGC
GGGCCAAGATCTGCACACTGGTATTTCGGTTTTTGGGGCCGCGGGCGGCGACGGGGC
CCGTGCGTCCCAGCGCACATGTTCGGCGAGGCGGGGCCTGCGAGCGCGGCCACCGA
GAATCGGACGGGGGTAGTCTCAAGCTGGCCGGCCTGCTCTGGTGCCTGGCCTCGCGC
CGCCGTGTATCGCCCCGCCCTGGGCGGCAAGGCTGGCCCGGTCGGCACCAGTTGCGT
GAGCGGAAAGATGGCCGCTTCCCGGCCCTGCTGCAGGGAGCTCAAAATGGAGGACG
CGGCGCTCGGGAGAGCGGGCGGGTGAGTCACCCACACAAAGGAAAAGGGCCTTTCC
GTCCTCAGCCGTCGCTTCATGTGACTCCACGGAGTACCGGGCGCCGTCCAGGCACCT
CGATTAGTTCTCGAGCTTTTGGAGTACGTCGTCTTTAGGTTGGGGGGAGGGGTTTTAT
GCGATGGAGTTTCCCCACACTGAGTGGGTGGAGACTGAAGTTAGGCCAGCTTGGCAC
TTGATGTAATTCTCCTTGGAATTTGCCCTTTTTGAGTTTGGATCTTGGTTCATTCTCAA
GCCTCAGACAGTGGTTCAAAGTTTTTTCCTTCCATTTCAGGTGTCGTGAAAACTACCC
CTAAAAGCCAAATCTAGAGCCACCATGGACATGCGCGTGCCGGCCACAACTGCTGGC
CTGCTGCTGCTTTGGCTGCGGGGAGCTAGATGCGAAGTGCAGCTCGTGGAATCCGGA
GGAGGACTGGTGCAGCCTGGCGGAAGCATGCGCGTGTCATGCGCGGCTTCCGGATTC
ACCTTCTCGGACGCCTGGATGGATTGGGTCAGACAAGCGCCCGGCAAAGGCCTGGAA
TGGGTGGCCGAGATTCGGTCCAAGGCCCATAACCACGCCACCTACTACGCCGACTCC
GTGAAGGGGCGCTTTACTATCTCCCGGGATAACTCGAAGAATACCGTGTACCTCCAG TABLE 3B-continued Exemplary Melanin Antibody Expressing Plasmid Nucleotide Sequences

```
ATGAACTCATTGAGGGCCGAGGACACTGGGGTCTACTACTGTACCCGCGGAGGCTAC
TACGGGAACTATGGTTTCTTCGCCTACTGGGGCCAGGGTACCCTCGTGACTGTCAGC
AGCGCCAGCACCAAGGGCCCCAGCGTGTTCCCACTGGCCCCAAGCTCCAAGTCAACC
TCCGGCGGAACTGCTGCGCTGGGCTGCTTGGTGAAGGACTACTTCCCCGAACCGGTC
ACCGTGTCCTGGAACAGCGGAGCCCTGACCTCGGGAGTCCACACTTTCCCCGCTGTG
CTGCAGTCGTCCGGCCTGTACTCGCTCTCGTCCGTGGTCACTGTCCCGTCCTCGTCCC
TGGGTACTCAGACCTACATTTGCAACGTCAACCACAAGCCTTCAAACACGAAAGTGG
ACAAGAAGGTCGAGCCGAAGTCCTGCGACAAAACCCATACTTGCCCTCCTTGTCCGG
CTCCCGAACTGCTGGGCGGACCTTCCGTGTTCCTCTTCCCGCCTAAGCCGAAAGACAC
CCTGATGATCAGCAGGACTCCGGAAGTGACATGCGTGGTGGTGGACGTGTCGCACGA
GGACCCGGAGGTCAAGTTTAATTGGTACGTGGACGGAGTGGAAGTCCACAACGCCA
AGACCAAGCCACGGGAAGAACAGTACAATTCCACCTATCGCGTGGTGTCCGTGCTTA
CCGTGCTTCACCAAGACTGGCTGAACGGAAAGGAGTACAAGTGCAAAGTGTCAAAC
AAAGCCCTGCCTGCCCCAATCGAAAAGACCATCAGCAAGGCCAAGGGGCAGCCTCG
GGAACCCCAAGTGTACACTCTCCCGCCGTCAAGAGATGAACTGACCAAGAACCAAGT
GTCCCTCACTTGTCTCGTGAAGGGATTCTACCCCTCCGATATCGCCGTGGAGTGGGAA
TCCAACGGGCAACCCGAGAACAACTACAAGACCACCCCTCCGGTGCTTGATTCCGAT
GGCTCCTTCTTCCTCTACTCCAAGCTGACCGTGGACAAGTCAAGATGGCAGCAGGGG
AACGTGTTCTCCTGCTCCGTCATGCACGAGGCCCTGCACAACCATTACACCCAGAAG
TCTCTGTCGCTGAGCCCGGGAAAATAATGAGGATCCCCCTATTCTATAGTGTCACCTA
AATGCTAGAGCTCGCTGATCAGCCTCGACTGTGCCTTCTAGTTGCCAGCCATCTGTTG
TTTGCCCCTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGG
GGTGGGGTGGGGCAGGACAGCAAGGGGGAGGATTGGGAAGACAATAGCAGGCATG
CTGGGGATGCGGTGGGCTCTATGGCTTCTGAGGCGGAAAGAACCAGCTGGGGCTCGA
GCGGCCGCAGATTGTACCTTCTGAGGCGGAAAGAACCAGCTGTGGAATGTGTGTCAG
TTAGGGTGTGGAAAGTCCCCAGGCTCCCAGCAGGCAGAAGTATGCAAAGCATGCAT
CTCAATTAGTCAGCAACCAGGTGTGGAAAGTCCCCAGGCTCCCAGCAGGCAGAAGT
ATGCAAAGCATGCATCTCAATTAGTCAGCAACCATAGTCCCGCCCCTAACTCCGCCC
ATCCCGCCCCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAGAAGTAGTG
AGGAGGCTTTTTTGGAGGCCTAGGCTTTTGCAAAAAGCTTACCATGATTGAACAAGA
TGGATTGCACGCAGGTTCTCCGGCCGCTTGGGTGGAGAGGCTATTCGGCTATGACTG
GGCACAACAGACAATCGGCTGCTCTGATGCCGCCGTGTTCCGGCTGTCAGCGCAGGG
GCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCT
CGACGTTGTCACTGAAGCGGGAAGGGACTGGCTGCTATTGGGCGAAGTGCCGGGGC
AGGATCTCCTGTCATCTCACCTTGCTCCTGCCGAGAAAGTATCCATCATGGCTGATGC
AATGCGGCGGCTGCATACGCTTGATCCGGCTACCTGCCCATTCGACCACCAAGCGAA
ACATCGCATCGAGCGAGCACGTACTCGGATGGAAGCCGGTCTTGTCGATCAGGATGA
TCTGGACGAAGAGCATCAGGGGCTCGCGCCAGCCGAACTGTTCGCCAGGCTCAAGGC
GCGCATGCCCGACGGCGAGGATCTCGTCGTGACCCATGGCGATGCCTGCTTGCCGAA
TATCATGGTGGAAAATGGCCGCTTTTCTGGATTCATCGACTGTGGCCGGCTGGGTGTG
GCGGACCGCTATCAGGACATAGCGTTGGCTACCCGTGATATTGCTGAAGAGCTTGGC
GGCGAATGGGCTGACCGCTTCCTCGTGCTTTACGGTATCGCCGCTCCCGATTCGCAGC
GCATCGCCTTCTATCGCCTTCTTGACGAGTTCTTCTGAGGGATCGCGGAGATCCAGAC
ATGATAAGATACATTGATGAGTTTGGACAAACCACAACTAGAATGCAGTGAAAAAA
ATGCTTTATTTGTGAAATTTGTGATGCTATTGCTTTATTTGTAACCATTATAAGCTGCA
ATAAACAAGTTAACAACAACAATTGCATTCATTTTATGTTTCAGGTTCAGGGGGAGG
TGTGGGAGGTTTTTTAAAGCAAGTAAAACCTCTACAAATGTGGTATGGCTGATTATG
AGCTCCAGCTTTTGTTCCCTTTAGTGAGGGTTAATTGCGCGCTTGGCGTAATCATGGT
CATAGCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAA
TGAATCGGCCAACGCGCGGGGAGAGGCGGTTTGCGTATTGGGCGCTCTTCCGCTTCC
TCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTG
CGCTCTGCTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTACGCGCAG
AAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAA
ACTTGGTCTGACAGTTACCAATGCTTAATCAGTGAGGCACCTATCTCAGCGATCTGTC
TATTTCGTTCATCCATAGTTGCCTGACTCCCCGTCGTGTAGATAACTACGATACGGGA
GGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAG
```

TABLE 3B-continued

Exemplary Melanin Antibody Expressing Plasmid Nucleotide Sequences

```
TTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAA
TTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATA
CGGGATAATACCGCGCCACATAGCAGAACTTTAAAAGTGCTCATCATTGGAAAACGT
TCTTCGGGGCGAAAACTCTCAAGGATCTTACCGCTGTTGAGATCCAGTTCGATGTAA
CCCACTCGTGCACCCAACTGATCTTCAGCATCTTTTTACTTTCACCAGCGTTTCTGGGT
GAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTC
CGCGCACATTTCCCCGAAAAGTGCCACCTGGGAAATTGTAAACGTTAATATTTTGTTA
AAATTCGCGTTAAATTTTTGTTAAATCAGCTCATTTTTTAACCAATAGGCCGAAATCG
GCAAAATCCCTTATAAATCAAAAGAATAGACCGAGATAGGGTTGAGTGTTGTTCCAG
TTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGG
GGTCGAGGTGCCGTAAAGCACTAAATCGGAACCCTAAAGGGAGCCCCCGATTTAGA
GCTTGACGGGGAAAGCCGGCGAACGTGGCGAGAAAGGAAGGGAAGAAAGCGAAAG
GAGCGGGCGCTAGGGCGCTGGCAAGTGTAGCGGTCACGCTGCGCGTAACCACCACA
CCCGCCGCGCTTAATGCGCCGCTACAGGGCGCGTCCCATTCGCCATTCAGGCTGCGC
AACTGTTGGGAAGGGCGAT
```

In some embodiments, the nucleotide sequence set forth in SEQ ID NO: 18 is utilized to produce a heavy chain of a melanin antibody.

In some embodiments, the nucleotide sequence set forth in SEQ ID NO: 19 is utilized to produce a light chain of a melanin antibody.

In some embodiments, the nucleotide sequence set forth in SEQ ID NO: 20 is utilized to produce a light chain of a melanin humanized antibody.

In some embodiments, the nucleotide sequence set forth in SEQ ID NO: 21 is utilized to produce a light chain of a melanin humanized antibody.

In some embodiments, the nucleotide sequence set forth in SEQ ID NO: 22 is utilized to produce a light chain of a melanin humanized antibody.

In some embodiments, the nucleotide sequence set forth in SEQ ID NO: 23 is utilized to produce a heavy chain of a melanin humanized antibody.

In some embodiments, the nucleotide sequence set forth in SEQ ID NO: 24 is utilized to produce a heavy chain of a melanin humanized antibody In some embodiments, the plasmid nucleotide sequence set forth in SEQ ID NO: 25 is utilized to produce a light chain of a melanin humanized antibody.

In some embodiments, the plasmid nucleotide sequence set forth in SEQ ID NO: 26 is utilized to produce a light chain of a melanin humanized antibody.

In some embodiments, the plasmid nucleotide sequence set forth in SEQ ID NO: 27 is utilized to produce a light chain of a melanin humanized antibody.

In some embodiments, the plasmid nucleotide sequence set forth in SEQ ID NO: 28 is utilized to produce a heavy chain of a melanin humanized antibody.

In some embodiments, the plasmid nucleotide sequence set forth in SEQ ID NO: 29 is utilized to produce a heavy chain of a melanin humanized antibody.

Therapeutic Uses

Provided herein are melanin antibodies for therapeutic use, for the treatment of melanoma.

Also provided herein are methods of treating melanoma comprising administering to a subject in need thereof a therapeutically effective amount of a therapeutic melanin antibody. In some embodiments, the melanoma is a primary melanoma. In some embodiments, the melanoma is a metastatic melanoma.

As used herein, a subject refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Subjects may be male or female.

Without being bound to any particular theory, in melanoma tumors and metastases, the cellular turnover is rapid, resulting in an increase in leaky melanoma cells where melanin is accessible to the melanin antibodies.

The administration of any of the therapeutic melanin antibodies provided herein may be administered in combination with other known drugs/treatments (e.g. small molecule drugs, or biologics). In some embodiments, the melanin antibodies may be administered with immune checkpoint inhibitors; in some embodiments, the immune checkpoint inhibitors are antibody-based immune checkpoint inhibitors. In some embodiments, the melanin antibodies may be administered with MEK inhibitors. In some embodiments, the melanin antibodies may be administered with Braf inhibitors. In some embodiments, the melanin antibodies may be administered with chemotherapeutic agents. In some embodiments, the melanin antibodies may be administered with biologics-based therapies targeting cancer cell signaling pathways. In some embodiments, the melanin antibodies may be administered with microbiome modulation therapies, metabolic or nutritional therapies. The administration may be sequential or concurrent.

In some embodiments, for treatment for metastatic melanoma, the melanin antibodies may be administered in combination with immunotherapy (e.g. immune checkpoint inhibitors such as CTLA4, PD1, PDL-1 inhibitors). In some embodiments, the melanin antibody is conjugated to an agent. In some embodiments, the melanin antibody is conjugated to a radionuclide.

In vivo administration of the therapeutic melanin antibodies described herein may be carried out intravenously, intratumorally, intracranially, intralesionally (e.g. intralesional injection, direct contact diffusion), intracavitary (intraperitoneal, intrapleural, intrauterine, intrarectal), intraperitoneally, intramuscularly, subcutaneously, topically, orally, transdermally, by implantation, by inhalation, intrathecally, intraventricularly, or intranasally. In an exemplary embodiment, the route of administration is by intravenous injection.

A therapeutically effective amount of the therapeutic antibody will be administered. The appropriate dosage of the therapeutic antibody may be determined based on the severity of the melanoma, the clinical condition of the subject, the subject's clinical history and response to the treatment, and the discretion of the attending physician The dosage amounts of the melanin antibodies provided herein may vary from about 1 ng/kg up to about 1000 mg/kg of a subject's body weight or more per day, depending upon the route of administration. For repeated administrations over several days or longer, depending on the severity melanoma, the treatment may be sustained until a desired suppression of symptoms is achieved. Dosage regimens may be useful, depending on the pattern of pharmacokinetic decay that the physician wishes to achieve. For example, dosing an individual from one to twenty-one times a week is provided herein. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is may be monitored by conventional techniques and assays. The dosing regimen may vary over time independently of the dose used.

Pharmaceutical Compositions

The present disclosure provides compositions comprising therapeutic melanin antibodies, In some embodiments the composition is sterile. The pharmaceutical compositions generally comprise an effective amount of the therapeutic antibody in a pharmaceutically acceptable excipient.

Diagnostic Uses

The melanin antibodies provided herein may be used for diagnostic and imaging purposes. Depending on the application, the melanin antibody may be detected and quantified in vivo or in vitro.

The melanin antibodies may be used for diagnostic purposes, either by detecting, localizing, or quantitating melanoma tumor cells, or melanin deposits in normal tissue.

The melanin antibodies provided herein are amendable for use in a variety of immunoassays. These immunoassays include, but are not limited to enzyme-linked immunosorbent assay (ELISA), Western blot, radioimmunoassay (RIA), flow cytometry, a radioimmunoassay, an immunofluorescence assay, spectrophotometry, radiography, electrophoresis, high performance liquid chromatography (HPLC), or thin layer chromatography (TLC).

The melanin antibodies provided herein may be comprise a detectable label, for example detectable by spectroscopic, photochemical, biochemical, immunochemical, fluorescent, electrical, optical or chemical methods. Useful labels in the present invention include, but are not limited to fluorescent dyes, radiolabels, enzymes, colorimetric labels, avidin or biotin.

In some embodiments, the melanin antibody is radiolabeled with an isotope, useful for imaging by nuclear medicine equipment (SPECT, PET, or scintigraphy).

The diagnostic melanin antibodies may be used for the diagnosis of the primary melanoma, to monitor metastases, or to determine response to a treatment.

Kits and Articles of Manufacture

The present application provides kits comprising a melanin antibody, e.g. for either therapeutic or diagnostic use. In some embodiments, the kits further contain a component selected from any of secondary antibodies, reagents for immunohistochemistry analysis, pharmaceutically acceptable excipient and instruction manual and any combination thereof. In some embodiments, the kit comprises any one or more of the therapeutic compositions described herein, with one or more pharmaceutically acceptable excipient.

The present application also provides articles of manufacture comprising any one of the therapeutic or diagnostic compositions or kits described herein. Examples of an article of manufacture include vials (e.g. sealed vials).

ILLUSTRATIVE EMBODIMENTS

The invention may be defined by reference to the following illustrative enumerated embodiments.

Embodiment 1

A monoclonal antibody that specifically binds to melanin, wherein the antibody is chimeric or humanized.

Embodiment 2

The antibody of embodiment 1, wherein the antibody is chimeric.

Embodiment 3

The antibody of claim 2, wherein the antibody is a chimeric mouse-human antibody.

Embodiment 4

The antibody of embodiment 3, wherein the chimeric antibody comprises mouse variable regions and human constant regions.

Embodiment 5

The antibody of any one of embodiments 1 to 4, wherein the melanin antibody comprises a light chain comprising the amino acid sequence of SEQ ID NO: 1.

Embodiment The antibody of any one of embodiments 1 to 5, wherein the melanin antibody comprises a heavy chain comprising the amino acid sequence of SEQ ID NO: 2.

Embodiment 7

The antibody of any one of embodiments 1 to 4, wherein the melanin antibody comprises a light chain comprising the amino acid sequence of SEQ ID NO: 1 and a heavy chain comprising the amino acid sequence of SEQ ID NO: 2.

Embodiment 8

The antibody of embodiment 1, wherein the antibody is humanized.

Embodiment 9

The antibody of embodiment 8, wherein the antibody is a humanized form of the sequence of a mouse monoclonal antibody.

Embodiment 10

The antibody of embodiment 9, wherein the antibody is a humanized form of a mouse 8C3 antibody.

Embodiment 11

The antibody of any one of embodiments 1, and 8 to 10, wherein the melanin antibody comprises a heavy chain comprising the amino acid sequence of SEQ ID NO: 3 or SEQ ID NO: 4.

Embodiment 12

The antibody of any one of embodiments 1, and 8 to 10, wherein the antibody comprises a light chain comprising the amino acid sequence of SEQ ID NO: 5, SEQ ID NO: 6, or SEQ ID NO: 7.

Embodiment 13

The antibody of any one of embodiments 11 and 12, wherein the antibody comprises a heavy chain comprising the amino acid sequence of SEQ ID NO: 3 and a light chain comprising the amino acid sequence of SEQ ID NO: 5.

Embodiment 14

The antibody of any one of embodiments 11 and 12, wherein the antibody comprises a heavy chain comprising the amino acid sequence of SEQ ID NO: 3 and a light chain comprising the amino acid sequence of SEQ ID NO: 6.

Embodiment 15

The antibody of any one of embodiments 11 and 12, wherein the antibody comprises a heavy chain comprising the amino acid sequence of SEQ ID NO: 3 and a light chain comprising the amino acid sequence of SEQ ID NO: 7.

Embodiment 16

The antibody of any one of embodiments 11 and 12, wherein the antibody comprises a heavy chain comprising the amino acid sequence of SEQ ID NO: 4 and a light chain comprising the amino acid sequence of SEQ ID NO: 5.

Embodiment 17

The antibody of any one of embodiments 11 and 12, wherein the antibody comprises a heavy chain comprising the amino acid sequence of SEQ ID NO: 4 and a light chain comprising the amino acid sequence of SEQ ID NO: 6.

Embodiment 18

The antibody of any one of embodiments 11 and 12, wherein the antibody comprises a heavy chain comprising the amino acid sequence of SEQ ID NO: 4 and a light chain comprising the amino acid sequence of SEQ ID NO: 7.

Embodiment 19

The antibody of any one of embodiments 1 to 10, wherein the heavy chain of the melanin antibody comprises at least one of the CDR sequences of SEQ ID NO: 8, SEQ ID NO: 9, or SEQ ID NO: 10.

Embodiment 20

The antibody of any one of embodiments 1 to 10, wherein the light chain of the melanin antibody comprises at least one of the CDR sequences of SEQ ID NO: 11, SEQ ID NO: 12, SEQ ID NO: 13, SEQ ID NO: 14, or SEQ ID NO: 15.

Embodiment 21

The antibody of any one of embodiments 1 to 10, wherein the heavy chain of the melanin antibody comprises at least one of the CDR sequences of SEQ ID NO: 8, SEQ ID NO: 9, or SEQ ID NO: 10, and wherein the light chain of the melanin antibody comprises at least one of the CDR sequences of SEQ ID NO: 11, SEQ ID NO: 12, SEQ ID NO: 13, SEQ ID NO: 14, or SEQ ID NO: 15.

Embodiment 22

The antibody of any one of embodiments 1 to 10, wherein the heavy chain of the melanin antibody comprises the CDR sequences from SEQ ID NO: 8, SEQ ID NO: 9, or SEQ ID NO: 10, and/or wherein the light chain comprises the CDR sequences from SEQ ID NO: 3 or SEQ ID NO: 4.

Embodiment 23

The antibody of embodiments 1 or 8 to 10, wherein the antibody is an antigen binding fragment.

Embodiment 24

The antibody of any one of embodiments 1 to 23, wherein the antibody is a bispecific antibody.

Embodiment 25

The antibody of embodiment 24, wherein the bispecific antibody comprises a first arm that targets melanin and a second arm that targets an antigen comprising an immune checkpoint inhibitor.

Embodiment 26

The antibody of embodiment 25, wherein the immune checkpoint inhibitor is CTLA4, PD-1, or PD-L1.

Embodiment 27

The antibody of any one of embodiments 1 to 26, wherein the antibody is conjugated to an agent.

Embodiment 28

The antibody of embodiment 27, wherein the agent is a radionuclide.

Embodiment 29

The antibody of embodiment 28, wherein the radionuclide is 213-Bi.

Embodiment The antibody of embodiment 28, wherein the radionuclide is 177-Lu.

Embodiment 31

The antibody of any one of embodiments 27 to 30, wherein the agent is conjugated to the antibody through a linker.

Embodiment 32

A pharmaceutical composition comprising the antibody of any one of embodiments 1 to 31 and a pharmacologically acceptable carrier.

Embodiment 33

A method for treating melanoma in a subject, comprising administering a therapeutically effective amount of the antibody or composition of any one of embodiments 1 to 32 to a subject in need thereof; or stated in an alternative: a therapeutically effective amount of the antibody of any one of embodiments 1 to 31 or composition of embodiment 32 for use in treating melanoma.

Embodiment 34

The method of embodiment 33, or antibody or composition for use according to embodiment 33 wherein the melanoma is metastasized.

Embodiment 35

The method of embodiment 33, or antibody or composition for use according to embodiment 33 or 34 wherein the administration selectively induces the cell death of melanoma cells.

Embodiment 36

The method of embodiment of any one of embodiments 33, 34 or 35, or antibody or composition for use according to any one of embodiments 33 to 35 comprising administering to the subject an effective amount of at least one additional agent.

Embodiment 37

The method of, or antibody or composition for use according to embodiment 36, wherein the agent is an immune checkpoint inhibitor.

Embodiment 38

The method of, or antibody or composition for use according to embodiment 37, wherein the immune checkpoint inhibitor is selected from CTLA-4, PD-1, and PDL-1.

Embodiment 39

The method of, or antibody or composition for use according to any one of embodiments 33 to 38, wherein the antibody or composition is administered intravenously.

Embodiment 40

A method of making a conjugated antibody comprising conjugating the antibody any one of embodiments 1 to 31 to an agent.

Embodiment 41

The method of embodiment 40, wherein the agent is a radionuclide.

Embodiment 42

The method of embodiment 41, wherein the radionuclide is 213-Bi.

Embodiment 43

The method of embodiment 41, wherein the radionuclide is 177-Lu.
Embodiment A polynucleotide encoding the amino acid sequence of an antibody of any one of embodiments 1 to 31.

Embodiment 45

The polynucleotide of embodiment 44, wherein the polynucleotide comprises the nucleotide sequence of SEQ ID NO: 17.

Embodiment 46

The polynucleotide of embodiment 44, wherein the polynucleotide comprises the nucleotide sequence of SEQ ID NO: 18.

Embodiment 47

The polynucleotide of embodiments 44 to 46, wherein the sequence has been codon optimized for expression in a human.

Embodiment 48

A vector comprising the polynucleotide of embodiment 44.

Embodiment 49

A cell line comprising the vector of embodiment 48.

Embodiment 50

A clonal cell expressing any one of the antibodies of embodiments 1 to 31.

Embodiment 51

A kit comprising any one of the antibodies or compositions of embodiments 1 to 32.

The following examples are included for illustrative purposes and are not intend to limit the scope of the invention.

EXAMPLES

Example 1: Construction and In Vitro Testing of Chimeric and Humanized Melanin Antibodies A mouse-human chimeric antibody was generated from the 8C3 murine monoclonal IgG melanin antibody (NCBI GenBank accession number KX346264; Urán M E, Nosanchuk J D, Restrepo A, Hamilton A J, Gómez B L, Cano L E. Detection of antibodies against *Paracoccidioides brasiliensis* melanin in in vitro and in vivo studies during infection. Clin Vaccine Immunol. 2011 October; 18(10): 1680-8). The chimeric antibody has human constant regions, and mouse variable regions. The chimeric 8C3 antibody is interchangeably referred to herein as "8C3 Chimera" or "Chimeric 8C3" or "Chimeric 8C3 hIgG1").

Two recombinant expression vectors encoding heavy and light chains of the 8C3-hIgG1 chimeric antibody were produced (pAB11-8C3-hIgG1 and pAB2-8C3-hKappa, FIG. 4). These vectors were then transfected into mammalian host cells using standard techniques.

Recombinant expression vectors encoding two gamma heavy chains and three kappa light chains of the humanized 8C3 antibody were produced. (FIG. 4)

Upon expressing the heavy and light chain portions of the antibody, the mammalian host cells secreted the resulting proteins into the host medium. The antibodies were then recovered from the host cell medium in which the host cells were cultured using standard techniques.

A collection of humanized 8C3 heavy and light chains were generated.

In vitro activity of the chimeric and humanized antibodies were assessed by an ELISA assay. *Sepia officinalis*-derived melanin (Sigma St. Louis, Mo., Sigma Cat # M2649-100 MG, Lot #103H1023V, 5 mg/mL in PBS). Eight, five-fold, serial dilutions were performed on each test sample, beginning at 80 ug/mL. (10 ug melanin/well A single assay plate was used to test all six humanized antibodies, the mouse 8C3 parent antibody, the chimeric 8C3 antibody, and the mouse and human IgG1 negative control antibodies. Biotinylated Goat Anti-human IgG Fc and Goat Anti-mouse-Fc antibodies were used. Streptavidin-HRP was used to detect both mouse and humanized biotinylated antibodies, and was also used to detect biotinylated chimeric 8C3. The Streptavidin-HRP (Thermo Fisher Scientific, Waltham, Mass.) was diluted 1:1000 from 1 mg/mL to detect the binding of biotinylated chimeric 8C3 to melanin. Biotinylated goat anti-mouse IgG-Fc (ABCAM, Cambridge, UK) or biotinylated goat anti-human IgG-Fc (ABCAM, Cambridge, UK) were diluted 1:1000 from 1 mg/mL to bind the mouse control or the human 8C3 and human controls, respectively, and the streptavidin-HRP was used for detection. The optical density (OD) of the well contents was read on a fluorescent plate reader using 450 nm emission filters. A curve-fit program was used to generate a standard curve, from which sample and control concentrations were interpolated.

Table 4 shows the test samples. (HE refers to humanized antibodies).

TABLE 4

| Protein | HE ID | Concentration (mg/mL) | Buffer |
|---|---|---|---|
| Mouse 8C3-mIgG1 | | 5.28 | Elution Pool (100 mM Glycine, 100 mM Tris, pH 7.2) |
| 8C3-hIgG1 Chimera | | 6.31 | Elution Pool (100 mM Glycine, 100 mM Tris, pH 7.2) |
| 8C3-HE-(VH3A-VK4)-hIgG1 | HE-1 | 4.26 | Elution Pool (100 mM Glycine, 100 mM Tris, pH 7.2) |
| 8C3-HE-(VH3A-VK1A)-hIgG1 | HE-2 | 3.53 | Elution Pool (100 mM Glycine, 100 mM Tris, pH 7.2) |
| 8C3-HE-(VH3A-VK1B)-hIgG1 | HE-3 | 3.61 | Elution Pool (100 mM Glycine, 100 mM Tris, pH 7.2) |
| 8C3-HE-(VH3B-VK4)-hIgG1 | HE-4 | 4.3 | Elution Pool (100 mM Glycine, 100 mM Tris, pH 7.2) |
| 8C3-HE-(VH3B-VK1A)-hIgG1 | HE-5 | 3.67 | Elution Pool (100 mM Glycine, 100 mM Tris, pH 7.2) |
| 8C3-HE-(VH3B-VK1B)-hIgG1 | HE-6 | 3.74 | Elution Pool (100 mM Glycine, 100 mM Tris, pH 7.2) |
| Human IgG1 Negative Control | | 6.54 | Elution Pool (100 mM Glycine, 100 mM Tris, pH 7.2) |
| Mouse IgG1 Negative Control | | 0.37 | Elution Pool (100 mM Glycine, 100 mM Tris, pH 7.2) |

Figure 1:
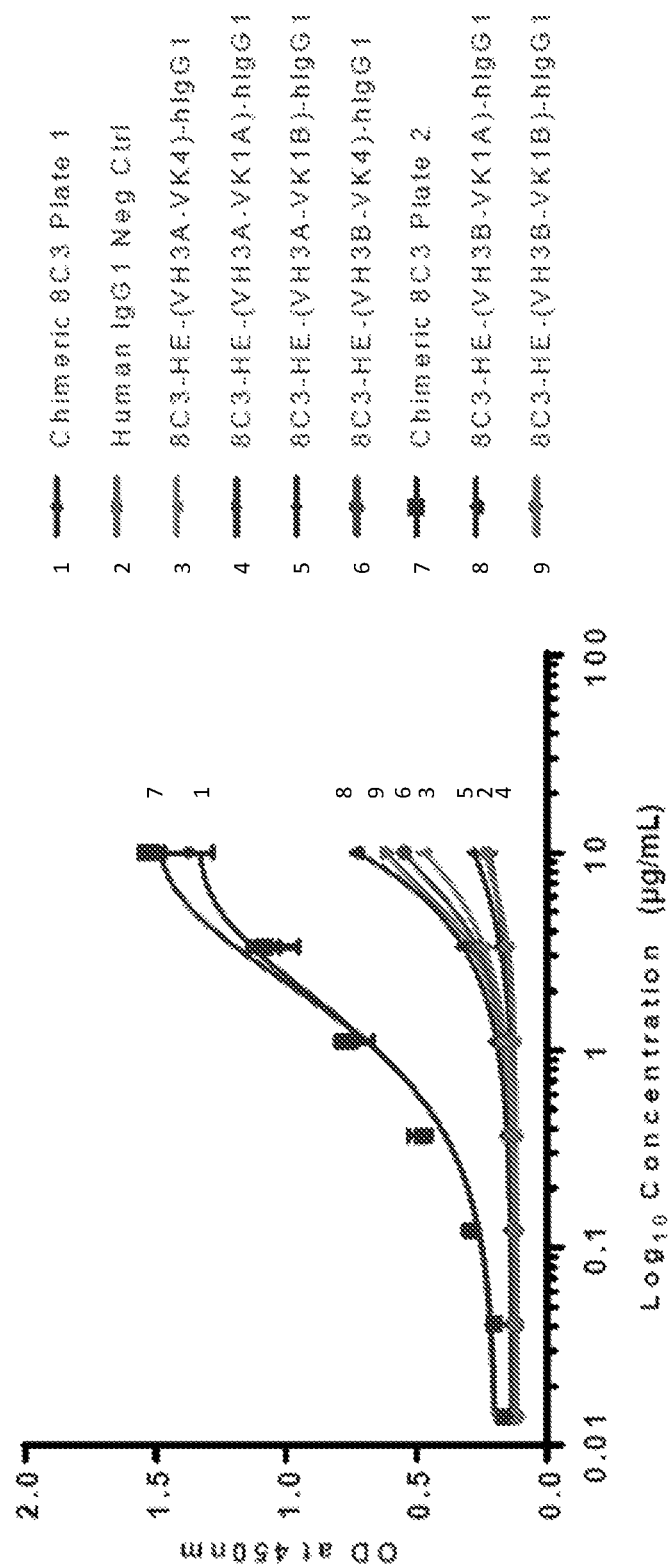
FIGS. 1 and 2 show the results of the binding of the chimeric 8C3 and humanized 8C3 antibodies to melanin, as assayed in vitro, in separate experiments.
Figure 2:
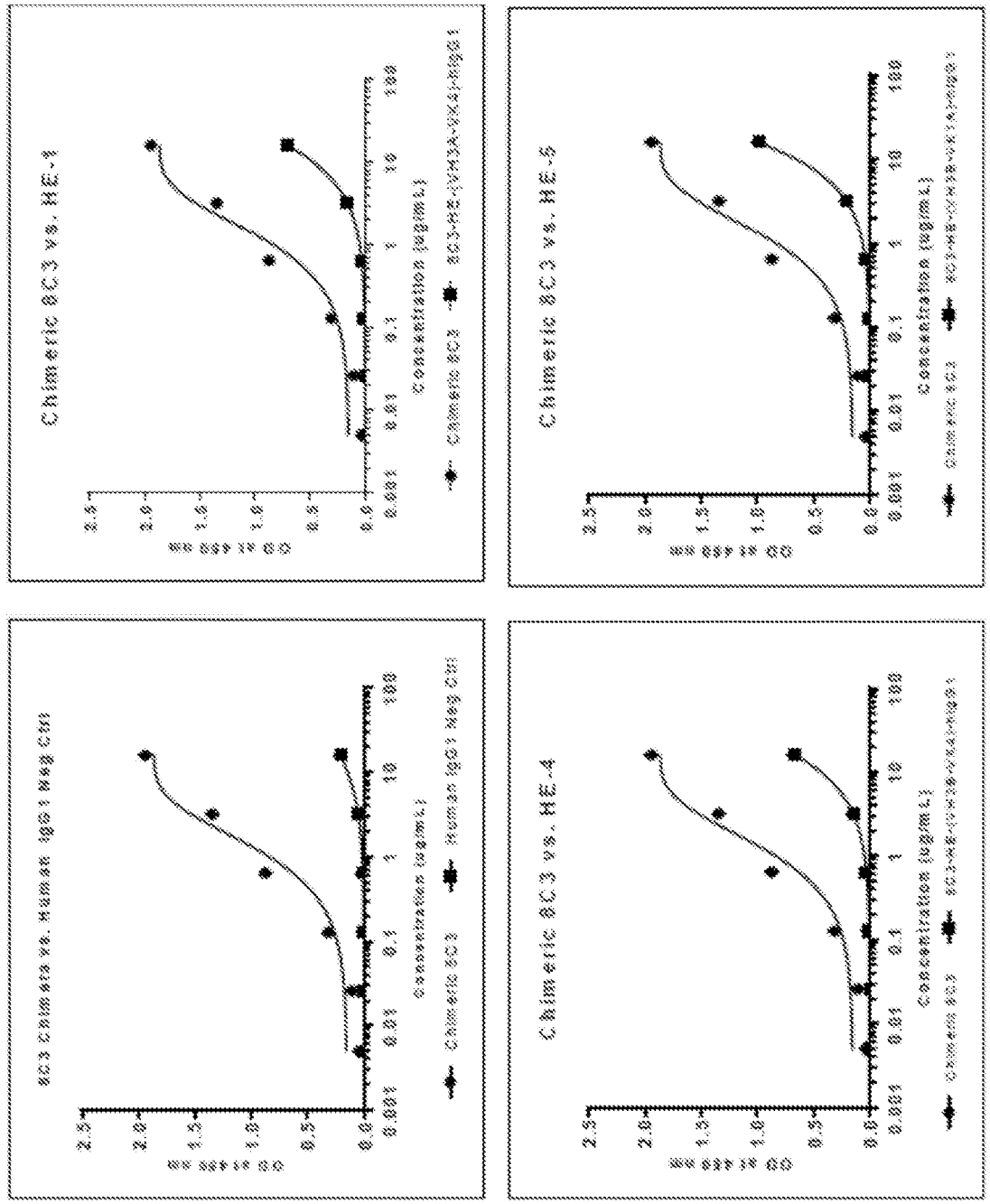

FIGS. 1 and 2 show the results of the binding of the chimeric 8C3 and humanized 8C3 antibodies to melanin, as assayed in separate experiments. In these assays, chimeric 8C3 demonstrates stronger binding to melanin from *Sepia officinalis* than the humanized 8C variants (8C3 HE-1 through 8C3 HE-6).

Table 5 shows the tabulated results of the average absorbance values at antibody concentrations of 10 μg/mL. These results correspond to the assay presented in FIG. 1.

TABLE 5

| Chimeric 8C3 Plate-1 | Human IgG1 Neg Ctrl | 8C3 HE-1 | 8C3 HE-2 | 8C3 HE-3 | 8C3 HE-4 | Chimeric 8C3 Plate-2 | 8C3 HE-5 | 8C3 HE-6 |
|---|---|---|---|---|---|---|---|---|
| 1.376 | 0.233 | 0.471 | 0.22 | 0.279 | 0.548 | 1.527 | 0.73 | 0.612 |

Table 6 shows the tabulated results of the average absorbance values at antibody concentrations of 16 μg/mL. These results correspond to the assay presented in FIG. 2.

TABLE 6

| Chimeric 8C3 | Human IgG1 Neg Ctrl | 8C3 HE-1 | 8C3 HE-2 | 8C3 HE-3 | 8C3 HE-4 | 8C3 HE-5 | 8C3 HE-6 | Mouse 8C3 | Mouse IgG1 Neg Ctrl |
|---|---|---|---|---|---|---|---|---|---|
| 1.945 | 0.209 | 0.707 | 0.162 | 0.356 | 0.676 | 0.989 | 0.734 | 0.441 | 0.039 |

Figure 3:
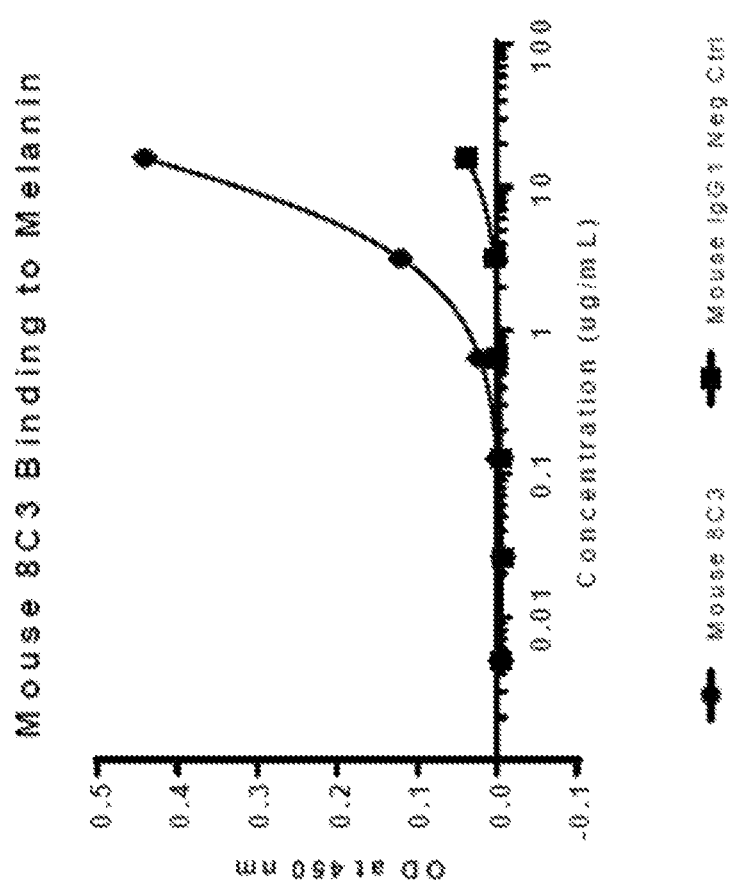
FIG. 3 compares the binding of mouse 8C3 and mouse IgG1 negative control antibodies to melanin from *Sepia officinalis*.
Figure 4C:
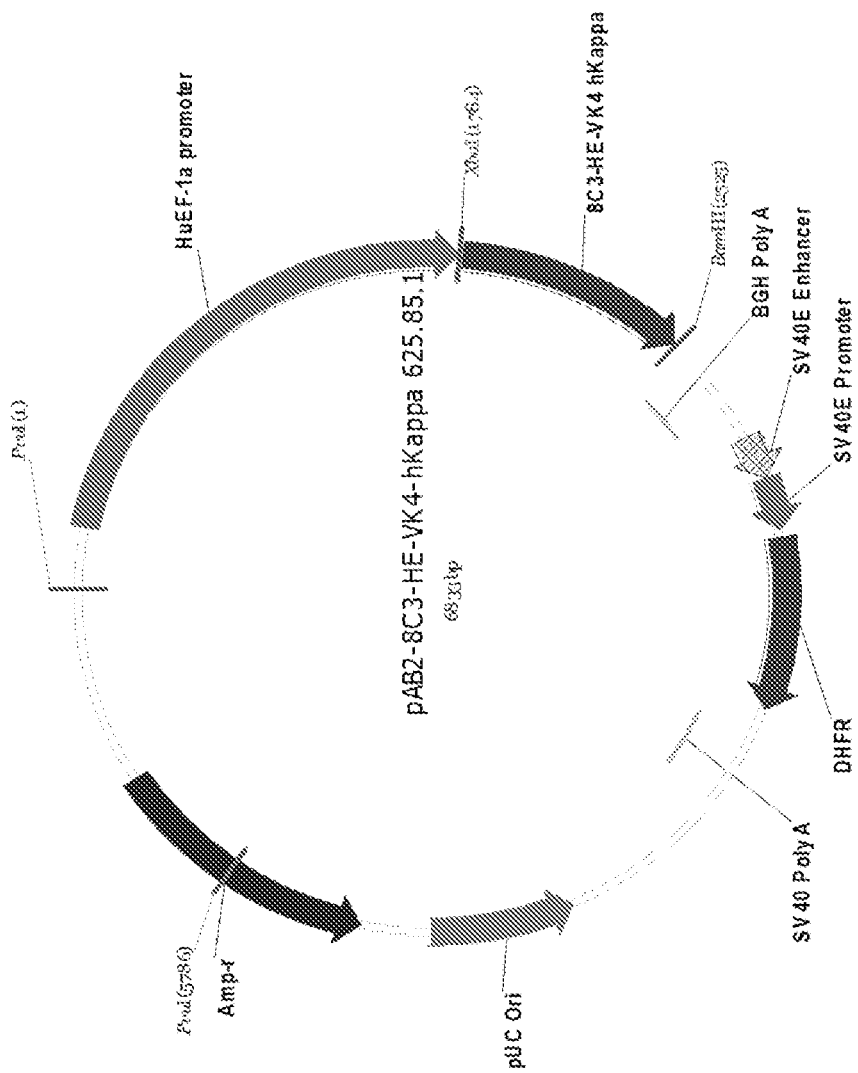
FIG. 4 provides schematic diagrams of the plasmids used for expression of the chimeric and humanized antibodies.
FIG. 4A) pAB11 8C3hIgG1 625.69.1, FIG. 4B) pAB2-8C3 hKappa-625.48.2, FIG. 4C) AB2-8C3-HE-VK4-hKappa 625.85.1, FIG. 4D) pAB2-8C3-HE-VK1A-hKappa-625.85.2, FIG. 4E) pAB2-8C3-HE-VK1B-hKappa-625.85.3, FIG. 4F) pAB11-8C3-HE-VH3A-hIgG1 625.85.4, and FIG. 4G) pAB11-8C3-HE-VH3B-hIgG1 625.85.5.
Figure 4D:
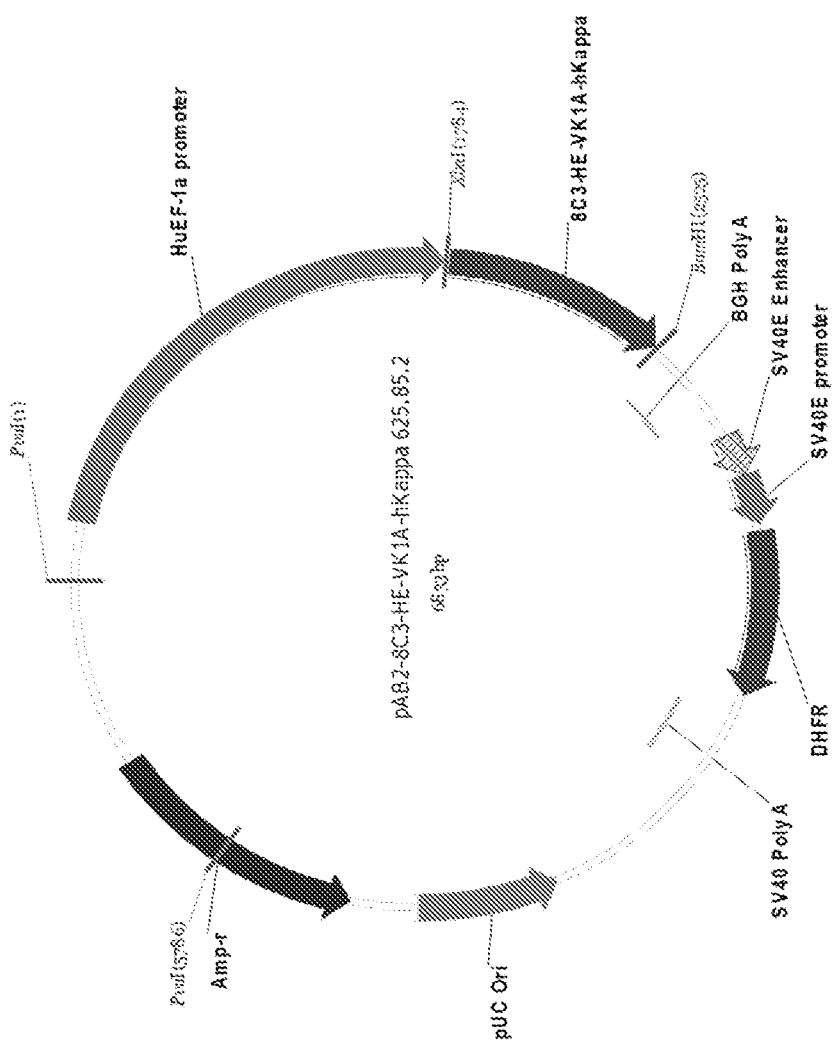
Figure 4E:
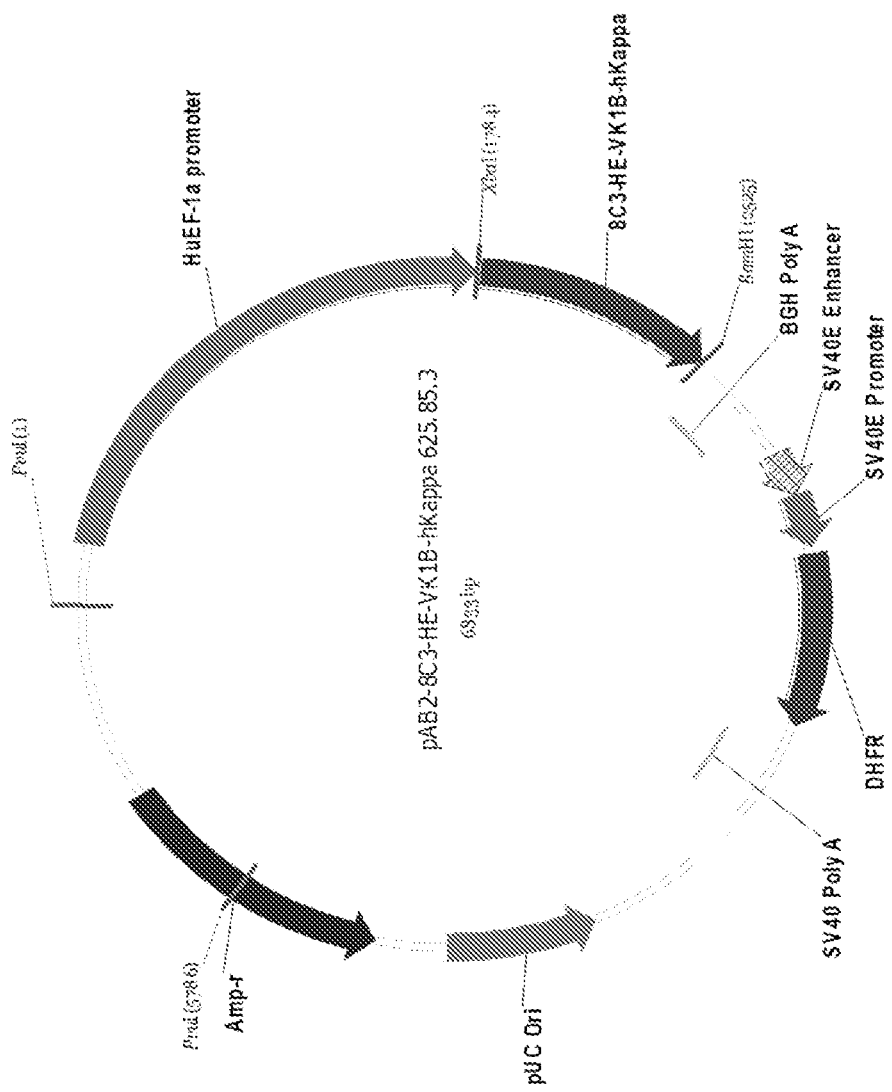
Figure 4F:
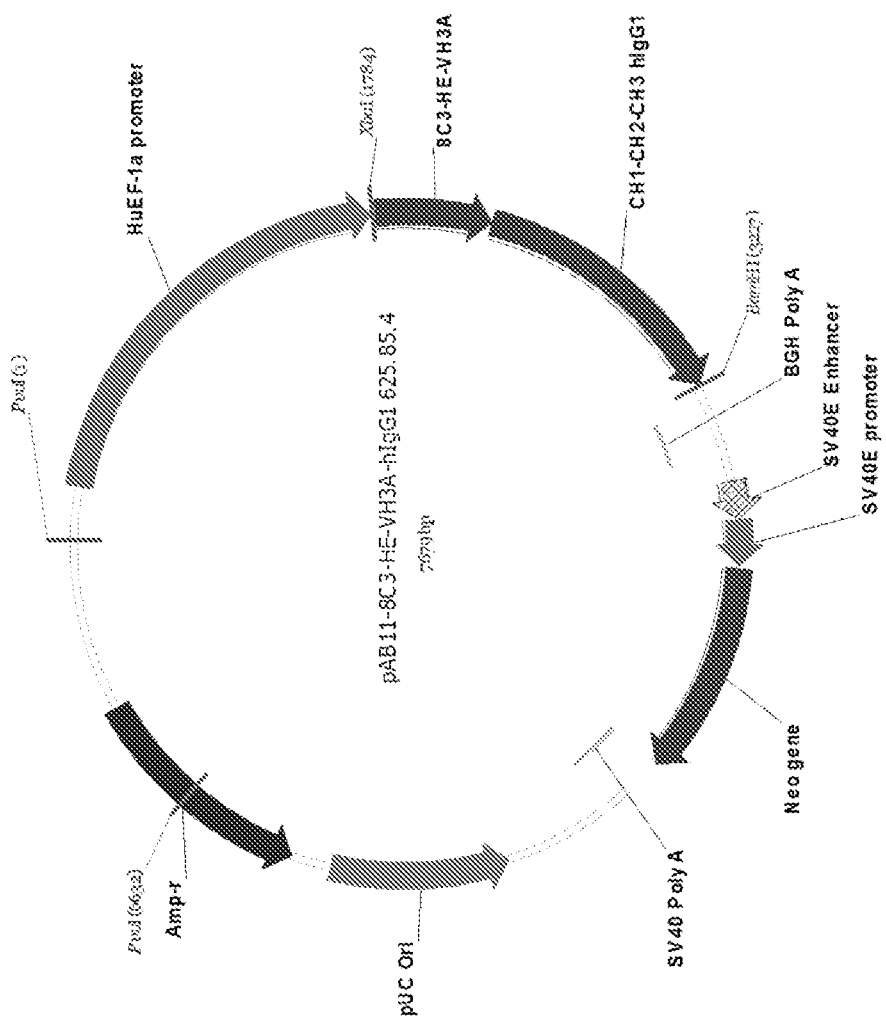
Figure 4G:
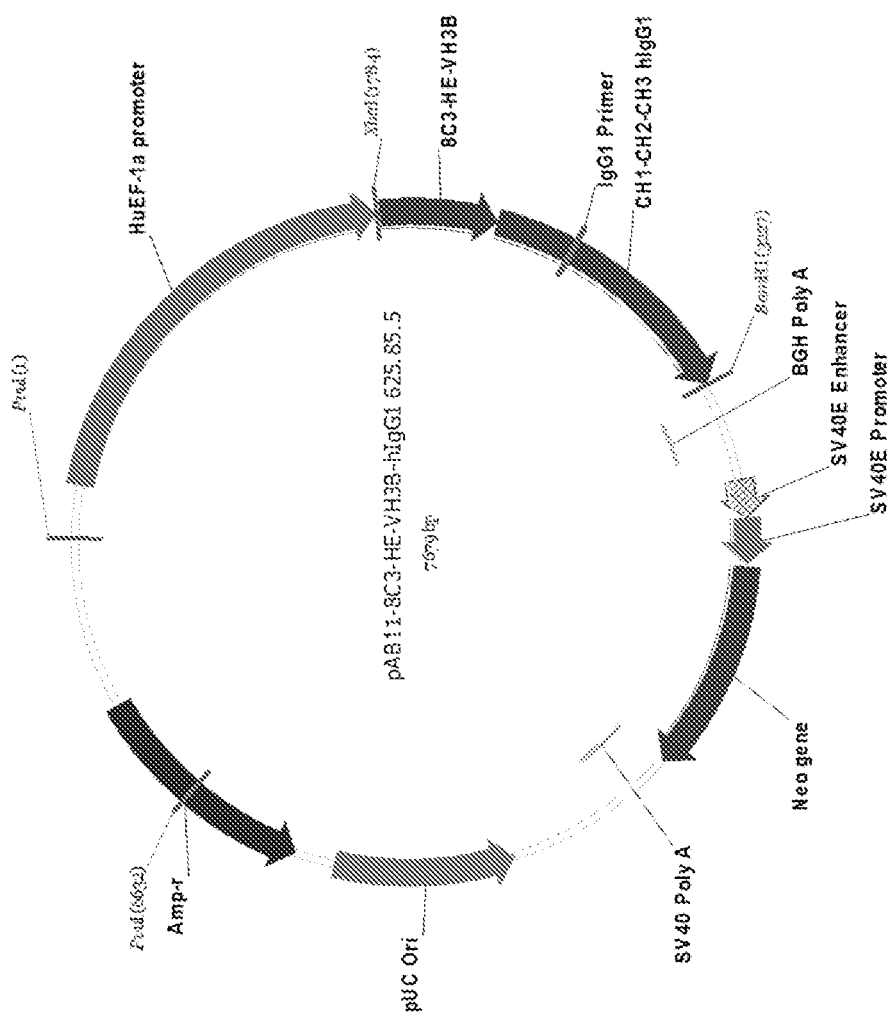

FIGS. 2 and 3 show the binding of chimeric 8C3 and parent mouse 8C3 antibodies to melanin from *Sepia officinalis*. FIG. 3 demonstrates stronger binding to melanin than mouse 8C3, and the average absorbance values for the test samples is provided in Table 7.

TABLE 7

Chimeric 8C3-hIgG1 (ng/ml)*

| Conc. | Average OD | SD | % CV |
|---|---|---|---|
| 2000 | 0.617 | 0.012 | 2.0 |
| 1000 | 0.418 | 0.015 | 3.6 |
| 500 | 0.282 | 0.008 | 2.9 |
| 250 | 0.205 | 0.008 | 4.0 |
| 125 | 0.159 | 0.002 | 1.6 |
| 62.5 | 0.145 | 0.011 | 7.4 |
| 31.2 | 0.123 | 0.006 | 4.9 |
| 15.6 | 0.118 | 0.005 | 4.2 |
| 7.8 | 0.104 | 0.004 | 4.2 |
| 3.9 | 0.102 | 0.005 | 4.9 |
| 1.9 | 0.093 | 0.002 | 2.2 |
| 0 | 0.094 | 0.014 | 14.9 |

*Assay performed in triplicate

FIG. 3 is a graph showing dose-dependent binding of mouse 8C3 to melanin.

FIG. 4 provides schematic diagrams of the plasmids used for expression of the heavy and light chains of the chimeric and humanized antibodies.

Figure 5:
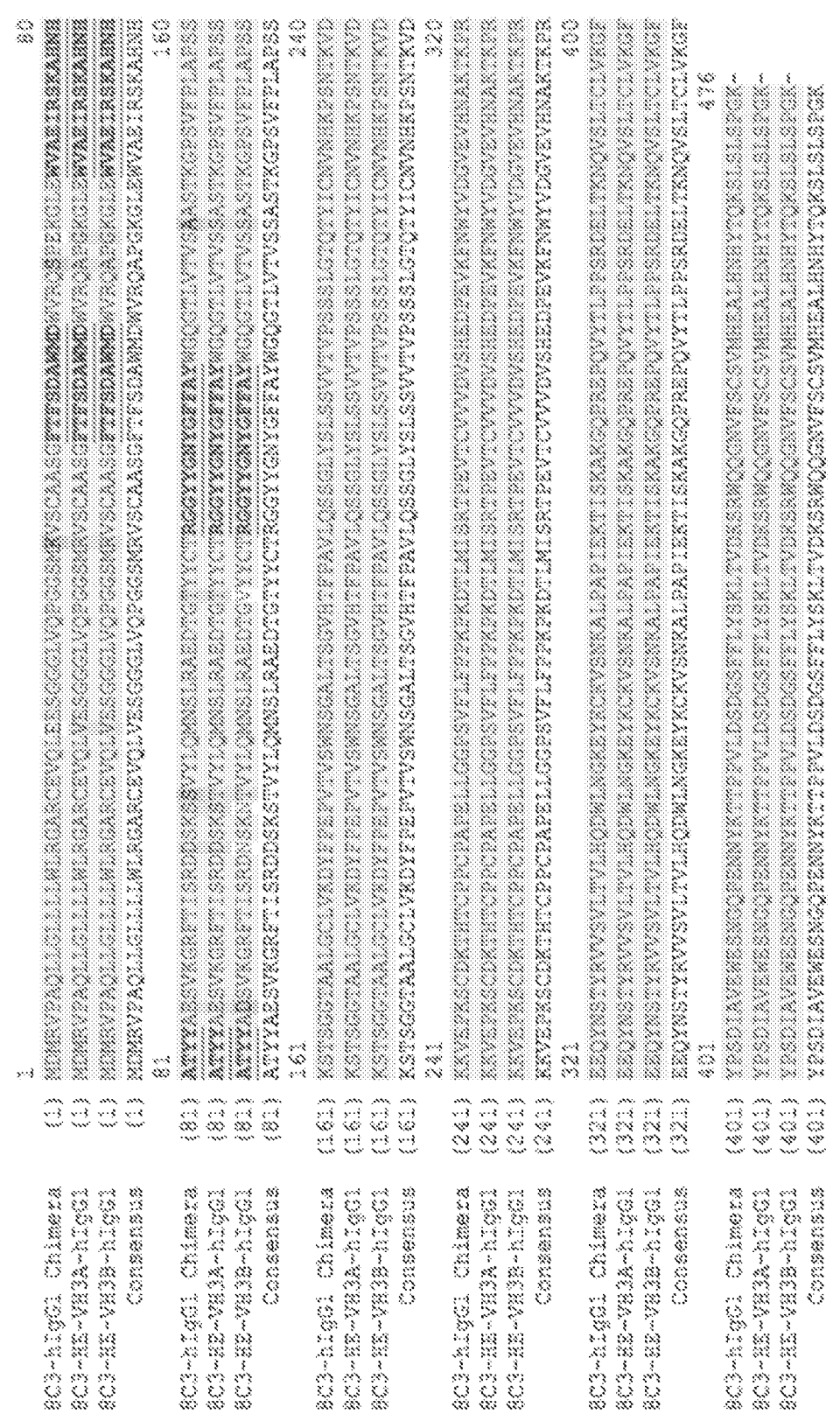
Figure 6:
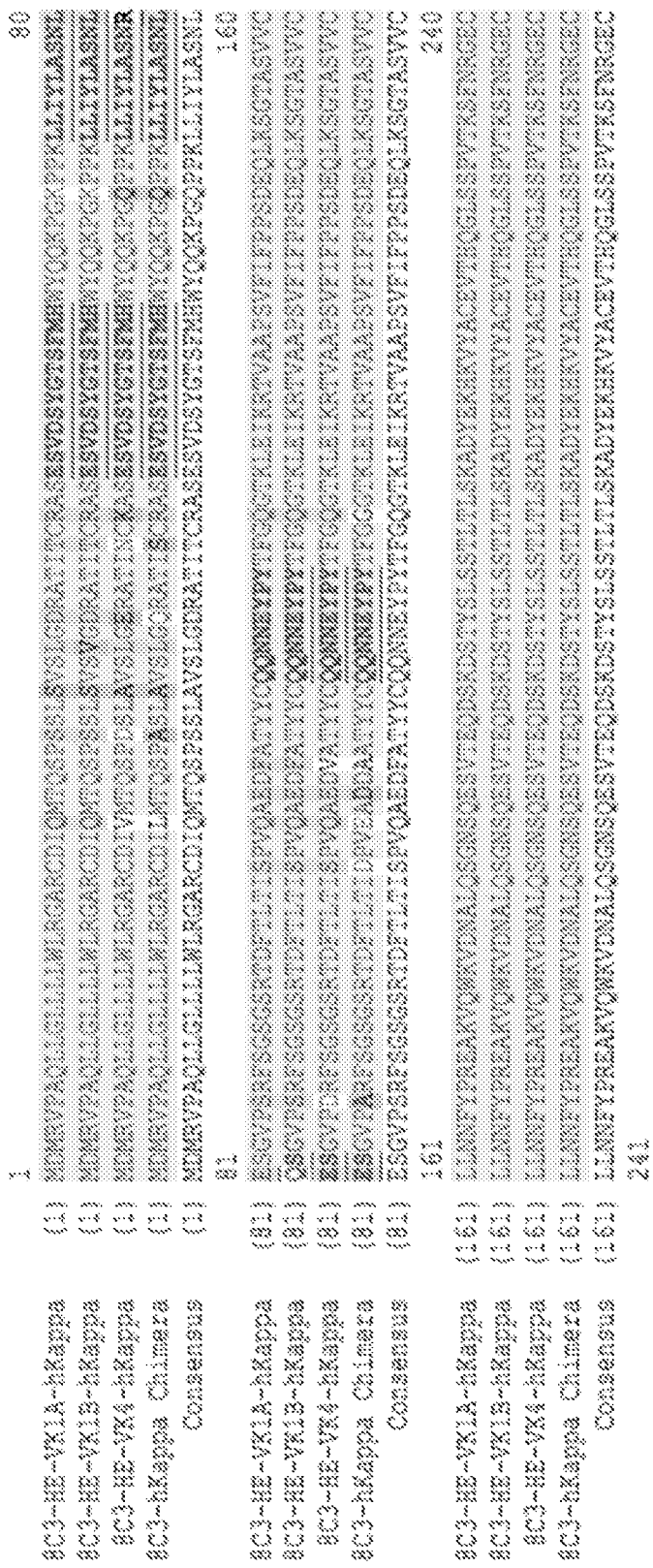
FIG. 6 show alignments of the light chains (SEQ ID NOs: 34-38) of the antibodies described herein.

FIG. 5 shows the alignment of the chimeric 8C3 heavy chain's amino acid sequence (8C3-hIgG1 chimera) and predicted complementarity-determining regions (CDR; shown in bold) with those of the two humanized 8C3 heavy chains (VH3A and VH3B). FIG. 6 shows the alignment of the chimeric 8C3 light chain's (8C3-hKappa Chimera) amino acid sequence and predicted complementarity-determining regions (CDR; shown in bold) with those of the three humanized 8C3 light chains (VK1A, VK1B, VK4). The consensus sequences for the heavy and light chains, respectively, are listed below the sequence alignments.

Table 8 provides chemical and physical properties of the humanized antibodies, using the ExPasy ProtParam tool.

TABLE 8

Chemical and Physical Properties of the Humanized Antibodies

8C3-HE-(VH3A-VK4)-hIgG1

Number of amino acids: 1342
Molecular weight: 147311.11
Theoretical pI: 7.3
Extinction coefficient:
Extinction coefficients are in units of $M^{-1}$ $cm^{-1}$,
at 280 nm measured in water.
Ext. coefficient 218360 Abs 0.1% (=1 g/l) 1.482,
assuming all pairs of Cys residues form cystines
8C3-HE-(VH3A-VK1A)-hIgG1

Number of amino acids: 1342
Molecular weight: 147301.16
Theoretical pI: 7.91
Extinction coefficient:
Extinction coefficients are in units of $M^{-1}$ $cm^{-1}$,
at 280 nm measured in water.
Ext. coefficient 218360 Abs 0.1% (=1 g/l) 1.482,
assuming all pairs of Cys residues form cystines
8C3-HE-(VH3A-VK1B)-hIgG1

Number of amino acids: 1342
Molecular weight: 147271.13

TABLE 8-continued

Chemical and Physical Properties of the Humanized Antibodies

Theoretical pI: 8.09
Extinction coefficient:
Extinction coefficients are in units of $M^{-1}$ $cm^{-1}$,
at 280 nm measured in water.
Ext. coefficient 218360 Abs 0.1% (=1 g/l) 1.483,
assuming all pairs of Cys residues form cystines
8C3-HE-(VH3B-VK4)-hIgG1

Number of amino acids: 1342
Molecular weight: 147311.11
Theoretical pI: 7.32
Extinction coefficient:
Extinction coefficients are in units of $M^{-1}$ $cm^{-1}$,
at 280 nm measured in water.
Ext. coefficient 218360 Abs 0.1% (=1 g/l) 1.482,
assuming all pairs of Cys residues form cystines
8C3-HE-(VH3B-VK1A)-hIgG1

Number of amino acids: 1342
Molecular weight: 147321.24
Theoretical pI: 8.09
Extinction coefficient:
Extinction coefficients are in units of $M^{-1}$ $cm^{-1}$,
at 280 nm measured in water.
Ext. coefficient 218360 Abs 0.1% (=1 g/l) 1.482,
assuming all pairs of Cys residues form cystines
8C3-HE-(VH3B-VK1B)-hIgG1

Number of amino acids: 1342
Molecular weight: 147291.22
Theoretical pI: 8.24
Extinction coefficient:
Extinction coefficients are in units of $M^{-1}$ $cm^{-1}$,
at 280 nm measured in water.
Ext. coefficient 218360 Abs 0.1% (=1 g/l) 1.483,
assuming all pairs of Cys residues form cystines Example 2: In Vivo Testing: Determination of Antibody Tissue Biodistribution For radiolabeling with $^{111}$Indium, the anti-melanin antibodies (humanized 8C3 (HE-5, see Table 6, mouse 8C3, and chimeric 8C3) and control IgG1 antibody were first conjugated to the bifunctional chelating agent CHXA" {N-[2-amino-3-(p-isothiocyanatophenyl)propyl]-trans-cyclo-hexane-1,2-diamine-N,N',N",N"',N""-pentaacetic acid} using standard methods. The CHXA" ligand was used in a 2-fold molar excess with respect to the antibodies. The antibodies were next radiolabeled with $^{111}$Indium according to standard methods. The $^{111}$Indium had a specific activity of 2 µCi/µg.

One million B16-F10 murine melanoma cells were suspended in tissue culture medium containing Matrigel according to standard protocol. The cells were injected into the right flank of C57BL/6 mice per standard procedure. On day four (post-injection), palpable tumors were observed.

Tissue biodistribution of radiolabeled humanized 8C3 HE-5, mouse 8C3, and chimeric 8C3 antibodies was measured in various organs eight days post-tumor cell engraftment. The uptake was calculated in terms of injected dose per gram tissue (ID/g, %) according to standard procedure. The uptake of the radiolabeled antibodies was measured at two different time points following intravenous injection of the aforementioned antibodies: four hours and twenty-four hours.

The amount of radiolabeled humanized 8C3 HE-5, mouse 8C3, and chimeric 8C3 antibodies and control human IgG1 antibody that bound the tumor was calculated in terms of a tumor-to-blood ratio per standard methods. Each tumor-bearing mouse received 30 µCi of $^{111}$Indium-mAb, and the amount of circulating (i.e. non-tumor bound) radiolabeled antibody post-injection was determined at two different time intervals: four hours and twenty-four hours.

Figure 7:
FIG. 7 shows a representative C57BL/6 mouse bearing a B16-F10 melanoma tumor (indicated by the black circle) prior to undergoing any mAB-based anti-melanin or control treatment.
Figures 8A, 8B:
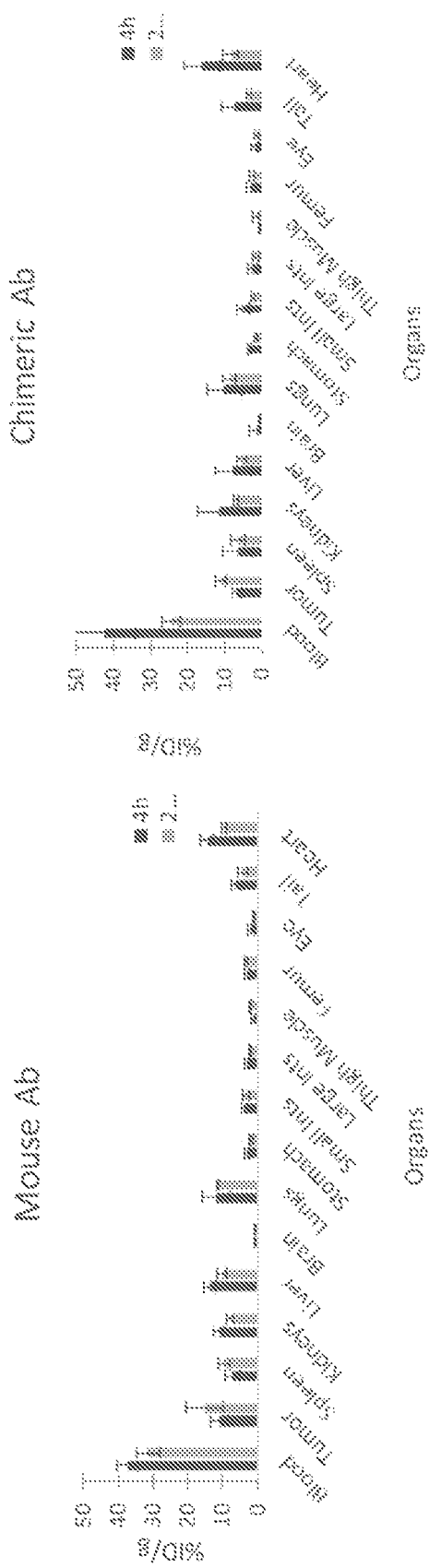
FIGS. 8A-8D depict the results of a biodistribution experiment that compared the uptake of radiolabeled melanin-binding antibodies in various organs to that of a non-specific human IgG antibody control at two different time points post-antibody injection (4 hours and 24 hours).
Figure 8C:
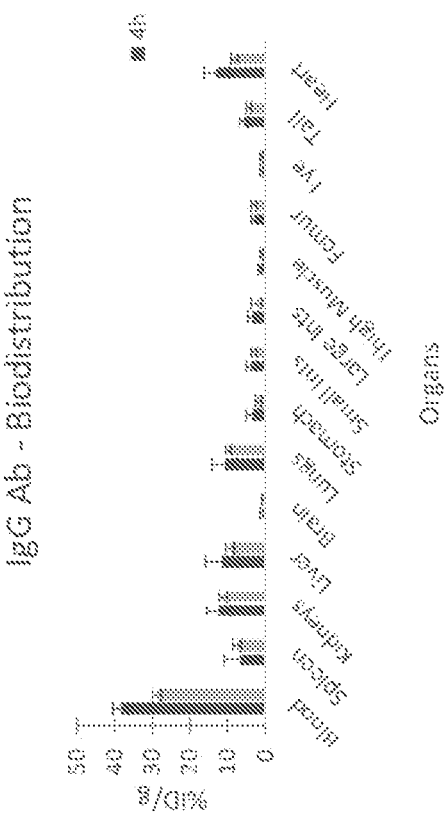
Figure 8D:
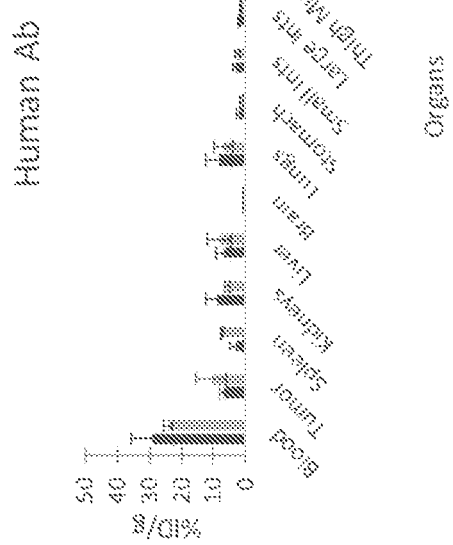

FIG. 7 shows a representative C57BL/6 mouse bearing a B16-F10 melanoma tumor (indicated by the black circle) prior to undergoing any mAB-based anti-melanin or control treatment. FIGS. 8A-8D depict the results of a biodistribution experiment that compared the uptake of radiolabeled melanin-binding antibodies in various organs to that of a non-specific human IgG antibody control at two different time points post-antibody injection (4 hours and 24 hours). The uptake was calculated in terms of injected dose per gram tissue (ID/g, %). Compared to the tumor uptake of the chimeric 8C3 and the humanized 8C3 anti-melanin antibodies (which were both similar), the tumor uptake of the mouse 8C3 antibody was higher. In melanin-containing organs (such as the eyes and tail), the uptake of the mouse, humanized and chimeric 8C3 melanin antibodies was similar to that of the human IgG antibody control.

Figure 9:
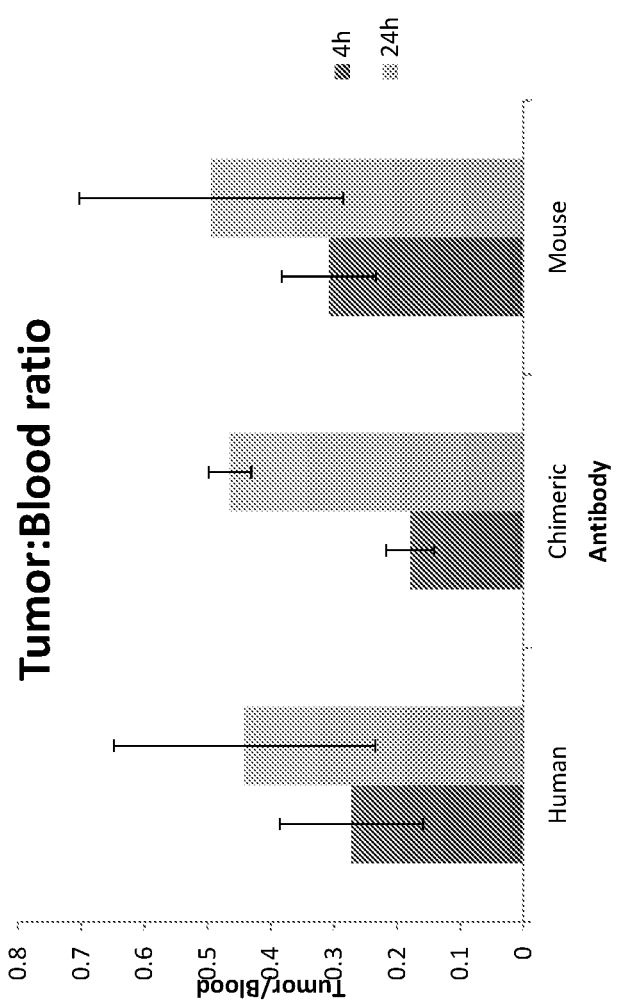
FIG. 9 shows the results of a tumor-to-blood ratio calculation, which provides a proxy measurement of the amount of radiolabeled melanin-binding antibodies that have bound the tumor.

FIG. 9 shows the results of a tumor-to-blood ratio calculation, which provides a proxy measurement of the amount of radiolabeled melanin-binding antibodies that have bound the tumor. Although the tumor-to-blood ratio of the murine 8C3 antibody was higher than that of the humanized and chimeric 8C3 antibodies at the four-hour time point, the murine, humanized and chimeric 8C3 antibodies demonstrated similar tumor-to-blood ratios at the twenty-four-hour time point.

Example 3: Detailed Biodistribution of Humanized 8C3 HE-5 for Subsequent Mouse and Human Dosimetry Calculations All animal studies were approved by the Animal Research Ethics Board of the University of Saskatchewan. For the imaging study 6 weeks old C57BL6 female mice obtained from Charles River Laboratories (USA) were injected subcutaneously with 5×10$^5$ B16-F10 murine melanoma cells in Matrigel (Corning, USA) into the right flank.

Conjugation of BCA CHXA" to 8C3 HE-5.

10× conjugation buffer (0.05 M Carbonate/Bicarbonate, 0.15 M NaCl, 5 mM EDTA, pH 8.6-8.7), 5 mL is combined with 0.5 M EDTA, pH=8.0 (0.5 mL) and was diluted to 50 mL in a 50 mL Falcon tube with deionized water to give the 1× buffer. An Amicon Ultra 0.5 mL centrifugal filter (30K MW cut off, Fisher) was loaded with 2 mg of the humanized 8C3 HE-5 (h8C3 HE-5) antibody. The antibody was exchanged into the above conjugation buffer by performing 6×1.5 mL washes using an Amicon concentrator in a refrigerated centrifuge at 4° C. The final volume should be around 250 µL containing 2 mg of the antibody. As the buffer exchange was getting close to completion, a solution of bifunctional CHXA" ligand with 2 mg/mL concentration is prepared by dissolving CHXA" in conjugation buffer. The antibody was recovered from the Amicon and 23.6 µL of 2 mg/mL CHXA" solution in conjugation buffer is added to provide 5 fold molar excess of CHXA" over the antibody. The reaction mixture was incubated at 37° C. for 1.5 hrs. The reaction mixtures is then purified into 0.15 M ammonium acetate buffer, pH=6.5-7.0, with 6×1.5 mL washes on Amicon concentrators in a refrigerated centrifuge at 4° C. The sample are stored at 4° C. A Bradford assay was performed to determine protein recovery and concentration.

Radiolabeling of Antibody-CHXA" Conjugate with $^{111}$Indium ($^{111}$In).

The radiolabeling of an antibody-CHXA" conjugate $^{111}$In was performed to achieve the specific activity of approximately 5 µCi/µg of the antibody. 600 µCi of $^{111}$In chloride was added to 10 µL 0.15 M ammonium acetate buffer and added to a microcentrifuge tube containing 120 µg of the h8C3 HE-5-CHXA" conjugate in 0.15 M ammonium acetate buffer. The reaction mixture was incubated for 60 min at 37° C., and then the reaction was quenched by the addition of 3 µL of 0.05 M EDTA solution. The percentage of radiolabeling was measured by SG-iTLC using 0.15 M ammonium acetate buffer as the eluent (top containing unlabeled $^{111}$In, bottom containing protein conjugated $^{111}$In). SG-iTLCs were read on a Perkin Elmer 2470 Automatic Gamma Counter.

The Biodistribution.

Figure 10:
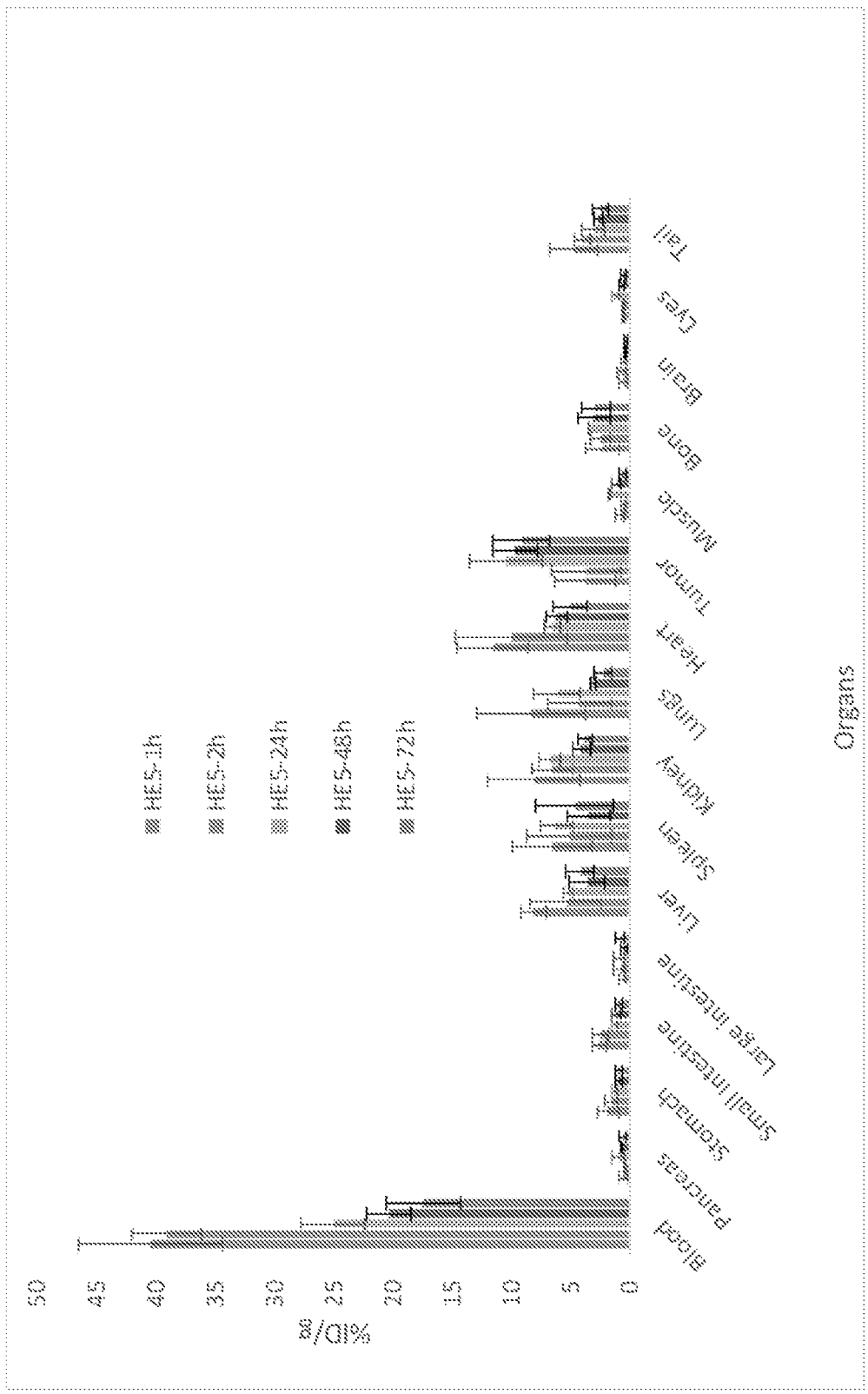
FIG. 10 is a graph depicting the biodistribution of 111In-h8C3 HE-5 antibody in mice at pre-determined time points of 1, 2, 24, 48 and 72 hrs post-injection of the radiolabeled antibody.

When the tumors in mice reached approximately 200 mm$^3$, the mice were randomized into the groups of 5 animals and injected IV via the tail vein with 50 µCi of 111In-h8C3 HE-5. At the pre-determined time points of 1, 2, 24, 48 and 72 hrs post-injection of the radiolabeled antibody the mice were humanely sacrificed, their major organs, blood, and tumors removed, weighted, and counted in Perkin Elmer 2470 Automatic Gamma Counter (see FIG. 10). The results of the biodistribution were used for mouse and human dosimetry calculations for the proposed therapeutic radionuclides 213Bi and 177Lu.

Example 4: Human Dosimetry Calculations for 213Bi- and 177Lu-Labeled h8C3 HE-5

This follow-up example presents dosimetry results for Bi-213 and Lu-177 in the human, extrapolated hypothetically from mouse data. The method described below is a method for extrapolating radiation dose results from mouse to human.

Methods

The extrapolation was performed by recalculating the residence times for the human model from the mouse model, and calculating the human doses using a MIRD schema implementing software such as OLINDA1.1. The method assumes proportionality based on weight differences between species (Kirschner A S, Ice R D, Beierwaltes W H, "Radiation-dosimetry of I-131-19-iodocholesterol: J Nucl Med. 16:248-249; 1975), $$R_h = R_m(O_h/B_h)/(O_m/B_m) \quad (1)$$

where $R_h$ is the recalculated human residence time for an organ or tissue, $R_m$ is the originally calculated mouse residence time, $O_h$ is the human organ weight, $O_m$ is the mouse organ weight, $B_h$ the human body weight, and $B_m$ is the mouse body weight.

Using OLINDA ver. 1.1, the organ or tissue absorbed doses for Bi-213 were calculated and for Lu-177 using the recalculated human residence times obtained from the method stated above. For bismuth-213, which has a branching decay chain, contributions from daughter products Po-213 (97.9%) and Tl-209 (2.1%) with doses from Bi-213 were summed. In this calculation, the absorbed dose to normal organs and tissues in centigray per millicurie administered (cGy/mCi) does not include any multiplier for quality factor or relative biological effectiveness for the alpha emissions from Bi-213 and Po-213.

The tumor is not a target organ in the output results from OLINDA1.1, but it may be calculated separately using the same method as for the normal organs and tissues. For calculating tumor dose in units of centigray-equivalent per unit mCi administered, all of the absorbed doses attributed to alpha emissions were multiplied by an arbitrary factor of 5 (see for example, Sgouros et al., 1999 [Reference: Sgouros G, Ballangrud A M, Jurcic J G, McDevitt M R, Humm J L, Erdi Y E, Mehta B M, Finn R D, Larson S M, Scheinberg D A, "Pharmacokinetics and dosimetry of an alpha-particle emitter labeled antibody: 213Bi-HuM195 (anti-CD33) in patients with leukemia," J Nucl Med. 40(11):1935-46; 1999] and Jurcic et al., 2002 [Reference: Jurcic J G, Larson S M, Sgouros G, McDevitt M R, Finn R D, Divgi C R, Ballangrud Å M, Hamacher K A, Ma D, Humm J L, Brechbiel M W, Molinet R, and Scheinberg D A, "Targeted α-particle immunotherapy for myeloid leukemia," Blood 100:1233-1239; 2002]). No such multiplier is needed for calculating the absorbed dose to tumor tissue from lutetium-177, which lacks alpha particles. To obtain the absorbed dose to tumor tissue for Bi-213 in conventional units, one may divide the centigray-equivalent dose by a factor of five to yield cGy/mCi administered to obtain the absorbed dose in cGy/mCi.

An additional caveat concerns the dose to human stomach, small intestines, and large intestines. In the MIRD schema, these organ doses are calculated using only the residence times (that is, the time-integrated activity coefficient values) obtained from radioactivity in the cavity contents, not from the cavity tissues. The mouse data represented activity in stomach and intestinal tissues (not temporary contents), and therefore it was assumed that the stomach, small intestines, and large intestines were part of the "remainder" tissues. The remainder includes all tissues in the mouse for which there was not a specific measurement for dosimetry. For example, activity in the mouse tail would be considered part of the remainder of whole body as applied by the method above to calculate the human dosimetry. The eyes are also part of the remainder, as are the other organs listed in the OLINDA1.1 output that were not specifically analyzed in the mouse study with In-111.

Blood is a transfer compartment and not a specified organ or tissue in the MIRD schema, so one does not calculate a specific dose to blood in OLINDA1.1. Dose to blood may be calculated directly in the mouse, however, but one does not extrapolate that dose to the human in OLINDA1.1.

In the following results (Table 9) the dose contributions from Bi-213 (plus daughters) and from Lu-177 are given for alpha particles, beta particles, photons, and total. All results are given to three significant figures in E-notation. The anthropomorphic model selected was the human adult. The numeric column is the equivalent of the Total column.

TABLE 9

| Bi-213 plus daughters Target Organ | Absorbed Dose (cGy/mCi) | | | | |
|---|---|---|---|---|---|
| | Alpha | Beta | Photon | Total | (Numeric) |
| Adrenals | 7.19E−02 | 1.34E−02 | 1.77E−03 | 8.70E−02 | 0.087 |
| Brain | 2.08E−03 | 3.87E−04 | 6.90E−04 | 3.15E−03 | 0.00315 |
| Breasts | 7.19E−02 | 1.34E−02 | 1.27E−03 | 8.65E−02 | 0.0865 |
| Gallbladder Wall | 7.19E−02 | 1.34E−02 | 1.97E−03 | 8.72E−02 | 0.0872 |
| Lower Large Intestine Wall | 7.19E−02 | 1.34E−02 | 2.16E−03 | 8.74E−02 | 0.0874 |
| Small Intestine | 7.19E−02 | 1.34E−02 | 2.40E−03 | 8.76E−02 | 0.0876 |
| Stomach Wall | 7.19E−02 | 1.34E−02 | 1.93E−03 | 8.72E−02 | 0.0872 |
| Upper Large Intestine Wall | 7.19E−02 | 1.34E−02 | 2.29E−03 | 8.75E−02 | 0.0875 |
| Heart Wall | 4.35E−03 | 8.09E−04 | 1.57E−03 | 6.74E−03 | 0.00674 |
| Kidneys | 1.88E−02 | 3.46E−03 | 1.41E−03 | 2.36E−02 | 0.0236 |
| Liver | 4.67E−02 | 8.68E−03 | 1.40E−03 | 5.68E−02 | 0.0568 |
| Lungs | 5.09E−03 | 9.47E−04 | 1.22E−03 | 7.26E−03 | 0.00726 |
| Muscle | 2.16E−03 | 4.02E−04 | 1.38E−03 | 3.94E−03 | 0.00394 |
| Ovaries | 7.19E−02 | 1.34E−02 | 2.22E−03 | 8.75E−02 | 0.0875 |
| Pancreas | 1.08E−04 | 1.99E−05 | 1.63E−03 | 1.76E−03 | 0.00176 |
| Red Marrow | 1.04E−01 | 9.44E−03 | 1.72E−03 | 1.15E−01 | 0.115 |
| Osteogenic Cells | 8.05E−01 | 2.31E−02 | 2.10E−03 | 8.30E−01 | 0.830 |
| Skin | 7.19E−02 | 1.34E−02 | 9.55E−04 | 8.62E−02 | 0.0862 |
| Spleen | 1.39E−03 | 2.57E−04 | 1.27E−03 | 2.91E−03 | 0.00291 |
| Testes | 7.19E−02 | 1.34E−02 | 1.53E−03 | 8.68E−02 | 0.0868 |
| Thymus | 7.19E−02 | 1.34E−02 | 1.55E−03 | 8.68E−02 | 0.0868 |
| Thyroid | 7.19E−02 | 1.34E−02 | 1.55E−03 | 8.68E−02 | 0.0868 |
| Urinary Bladder Wall | 7.19E−02 | 1.34E−02 | 2.05E−03 | 8.73E−02 | 0.0873 |
| Uterus | 7.19E−02 | 1.34E−02 | 2.30E−03 | 8.75E−02 | 0.0875 |
| Total Body | 7.41E−02 | 1.38E−02 | 1.42E−03 | 8.93E−02 | 0.0893 |
| Centigray-equivalent dose per mCi administered, alpha multiplier = 5 | | | | | |
| Tumor | 2.93E−01 | 3.02E−03 | 1.32E−03 | 2.98E−01 | 0.298 |

| Lu-177 Target Organ | Beta | Photon | Total | (Numeric) |
|---|---|---|---|---|
| Adrenals | 2.21E−01 | 2.69E−02 | 2.48E−01 | 0.248 |
| Brain | 1.17E−02 | 1.13E−02 | 2.29E−02 | 0.023 |
| Breasts | 2.21E−01 | 1.65E−02 | 2.38E−01 | 0.238 |
| Gallbladder Wall | 2.21E−01 | 2.86E−02 | 2.50E−01 | 0.250 |
| Lower Large Intestine Wall | 2.21E−01 | 3.17E−02 | 2.53E−01 | 0.253 |
| Small Intestine | 2.21E−01 | 3.51E−02 | 2.56E−01 | 0.256 |
| Stomach Wall | 2.21E−01 | 2.71E−02 | 2.48E−01 | 0.248 |
| Upper Large Intestine Wall | 2.21E−01 | 3.32E−02 | 2.54E−01 | 0.254 |
| Heart Wall | 1.33E−02 | 2.32E−02 | 3.65E−02 | 0.037 |
| Kidneys | 6.90E−02 | 2.10E−02 | 9.00E−02 | 0.090 |
| Liver | 1.49E−01 | 2.05E−02 | 1.69E−01 | 0.169 |
| Lungs | 1.18E−02 | 1.84E−02 | 3.02E−02 | 0.0302 |

TABLE 9-continued

| | | | | |
|---|---|---|---|---|
| Muscle | 1.58E-02 | 1.93E-02 | 3.51E-02 | 0.0351 |
| Ovaries | 2.21E-01 | 3.32E-02 | 2.54E-01 | 0.254 |
| Pancreas | 1.09E-03 | 2.48E-02 | 2.59E-02 | 0.0259 |
| Red Marrow | 1.64E-01 | 2.38E-02 | 1.88E-01 | 0.188 |
| Osteogenic Cells | 7.12E-01 | 4.43E-02 | 7.56E-01 | 0.756 |
| Skin | 2.21E-01 | 1.25E-02 | 2.34E-01 | 0.234 |
| Spleen | 7.90E-03 | 1.89E-02 | 2.68E-02 | 0.0268 |
| Testes | 2.21E-01 | 2.11E-02 | 2.42E-01 | 0.242 |
| Thymus | 2.21E-01 | 2.26E-02 | 2.44E-01 | 0.244 |
| Thyroid | 2.21E-01 | 2.30E-02 | 2.44E-01 | 0.244 |
| Urinary Bladder Wall | 2.21E-01 | 2.92E-02 | 2.50E-01 | 0.250 |
| Uterus | 2.21E-01 | 3.39E-02 | 2.55E-01 | 0.255 |
| Total Body | 2.32E-01 | 2.16E-02 | 2.53E-01 | 0.253 |
| Tumor | 3.14E-01 | 2.23E-02 | 3.36E-01 | 0.336 |

Example 5: Mouse Dosimetry Calculations for 213Bi- and 177Lu-Labeled h8C3 HE-5

Using the In-111 tracer biokinetic data (decay corrected), the radiation doses from Bi-213 and Lu-177 in mice were calculated by assuming either Bi-213 or Lu-177 in place of In-111. I plotted the recalculated effective data for Bi-213 and Lu-177, obtained a best-fit mathematical function for the plotted data points, integrated the best-fit function for each source organ or tissue, and multiplied by the equilibrium dose constant and specific absorbed fraction.

The mouse data was back-decay-corrected (percent administered activity per gram tissue) to obtain the effective data (related to actual counts) for Bi-213 (half-life is 45.6 minutes) and for Lu-177 (half-life is 160 hours). For each organ or tissue, the effective data points were plotted against sampling time, and linear least-squares regression analysis was performed to obtain a best-fit single (or double) exponential function to the data, with best-fit equation parameters.

Next, the exponential function was integrated to obtain an estimate of the microcurie-hours per microcurie administered, represented by the area under the time-activity function, integrated to infinity (complete decay) for both the Bi-213 and the Lu-177 cases. It was assumed that the Bi-213 absorbed fraction was 1.0 for all emissions in the mouse organs and tissues. Model values for Lu-177 emissions were calculated for fraction of energy emitted from the measured organ or tissue that deposits in the same organ or tissue using the mouse model developed earlier by Miller et al. (Miller W H, Hartmann-Siantar C, Fisher D R, Descalle M-A, Daly T, Lehmann J, Lewis M R, Hoffman T, Smith J, Situ P D, and Volkert W A, "Evaluation of Beta Absorbed Fractions in a Mouse Model for $^{90}$Y, $^{188}$Re, $^{166}$Ho, $^{149}$Pm, $^{64}$Cu, and $^{177}$Lu Radionuclides." *Cancer Biother. & Radiopharm.* 20(4):436-449; 2005).

Equilibrium dose constants for Bi-213 and Lu-177 were obtained from Eckerman K F and Endo A, *MIRD Radionuclide Data and Decay Schemes,* 2$^{nd}$ ed., Reston, Va.: Society of Nuclear Medicine; 2008. For Bi-213, the equilibrium dose constant is 19.44 g cGy uCi$^{-1}$ hr$^{-1}$, and for Lu-177, the equilibrium dose constant is 0.315 g cGy uCi$^{-1}$ hr$^{-1}$. With the equilibrium dose constant, the absorbed fraction of emitted beta energy, and the integral activity residing in the organ or tissue through complete decay all known or calculated, the absorbed dose in units of cGy (centigray) per microcurie (cGy/uCi) administered Bi-213 and Lu-177 was then calculated to obtain the following results (average dose and correlation coefficient):

Results for mouse organs are shown in Table 10:

TABLE 10

| | Bismuth-213 | | Lutetium-177 | |
|---|---|---|---|---|
| | Absorbed Dose (cGy/μCi admin.) | Correlation Coefficient (r) | Absorbed Dose (cGy/μCi admin.) | Correlation Coefficient (r) |
| Blood | 8.590 | 1.0 | 6.440 | 0.95 |
| Pancreas | 0.099 | 1.0 | 0.177 | 0.85 |
| Stomach | 0.389 | 1.0 | 0.346 | 0.96 |
| Small Intestine | 0.548 | 1.0 | 0.301 | 0.90 |
| Large intestine | 0.116 | 1.0 | 0.386 | 0.90 |
| Liver | 1.800 | 1.0 | 1.330 | 0.88 |
| Spleen | 1.409 | 1.0 | 1.707 | 0.87 |
| Kidney | 1.732 | 1.0 | 1.550 | 0.93 |
| Lungs | 2.010 | 1.0 | 1.079 | 0.89 |
| Heart | 2.453 | 1.0 | 1.822 | 0.93 |
| Tumor | 0.805 | 1.0 | 3.429 | 0.89 |
| Muscle | 0.158 | 1.0 | 0.298 | 0.99 |
| Bone | 0.502 | 1.0 | 0.679 | 0.50 |
| Brain | 0.113 | 1.0 | 0.159 | 0.95 |
| Eyes | 0.108 | 1.0 | 0.146 | 0.60 |
| Tail | 1.014 | 1.0 | 0.917 | 0.97 |

The Pearson product-moment correlation coefficient (r) is a measure of the strength and direction of the linear relationship between two variables defined as the covariance of the variables divided by the product of their standard deviations, and indicates the correlation between the data and the mathematical function that was used to integrate the area-under-curve to determine the number of radioactive transitions taking place in the organ or tissue (integrated to infinity). The r values for Bi-213 are high because of its very short half-life, and which gave three time points for curve-fitting.

Example 6: Comparative Therapy of B16-F10 Melanoma Tumors with 213Bi- Versus 177Lu-Labeled h8C3 HE-5 Antibody 213Bi/225Ac generator was purchased from Oak Ridge National Laboratory (TN, USA), 177Lu chloride—from Radiomedix (TX, USA). The h8C3 HE-5 antibody was conjugated to CHXA" bifunctional ligand as described in Detailed Biodistribution. The antibody was radiolabeled with 213Bi which was eluted from 213Bi/225Ac generator immediately prior to the radiolabeling in form of 213Bi iodide or with 177Lu. The radiolabeling of an antibody-CHXA" conjugate with 213Bi or Lu was performed to achieve the specific activity of approximately 5 µCi/µg of the antibody. To prepare a "high" (400 µCi) dose of 213Bi- or 177Lu-labeled antibody, 400 µCi of a radionuclide solution in 0.15 M ammonium acetate buffer was added to 80 µg of the antibody-CHXA" conjugate; to prepare a "low" (200 µCi) dose of 213Bi- or 177Lu-labeled antibody, 200 µCi of a radionuclide solution in 0.15 M ammonium acetate buffer was added to 40 µg of the antibody-CHXA" conjugate. For labeling with 213Bi the reaction mixture was incubated for 5 min at 37° C., for labeling with 177Lu—for 60 min. The incubation was followed by quenching the reaction by the addition of 3 µL of 0.05 M EDTA solution. The percentage of radiolabeling was measured by SG-iTLC using 0.15 M ammonium acetate buffer as the eluent (top containing free radionuclide, bottom containing radiolabeled antibody). SG-iTLCs were read on a Perkin Elmer 2470 Automatic Gamma Counter.

Figure 11A:
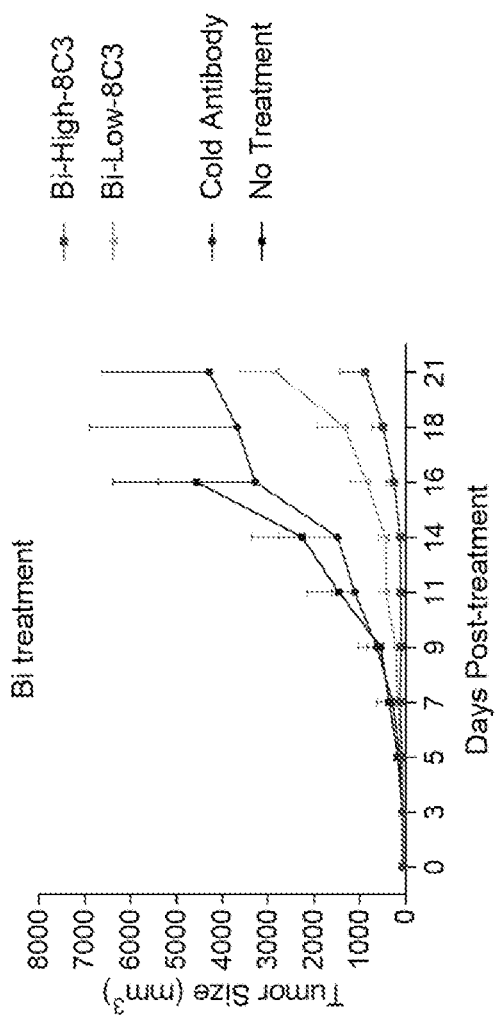
FIGS. 11A and 11B are graphs depicting tumor volume in mice treated with either: high dose of 213Bi-h8C3 HE-5, or low dose of 213Bi-h8C3 HE-5, or high dose of 177Lu-h8C3 HE-5, or low dose of 177Lu-h8C3 HE-5, or 80 µg unlabeled ("cold") h8C3 HE-5, or left untreated. Their tumors were measured every three days with electronic calipers to calculate the tumor volume.
Figure 11B:
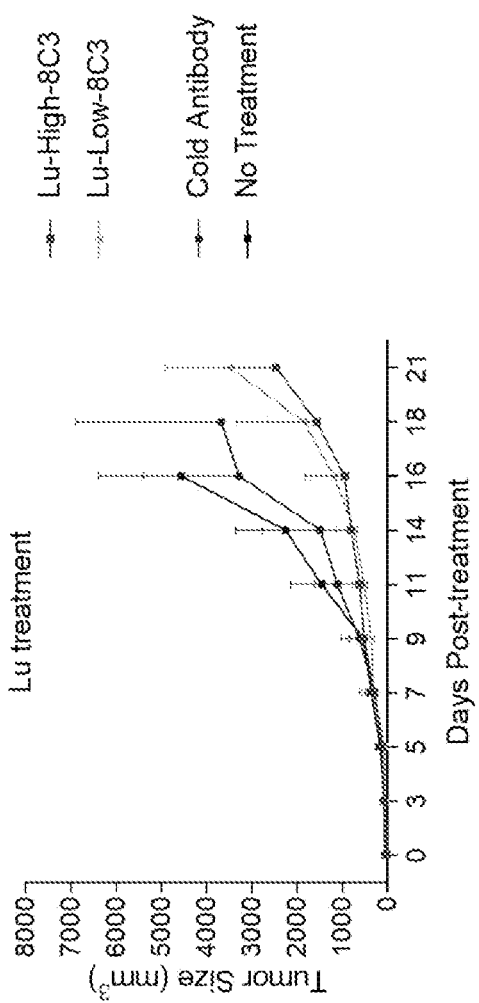
Figure 12A:
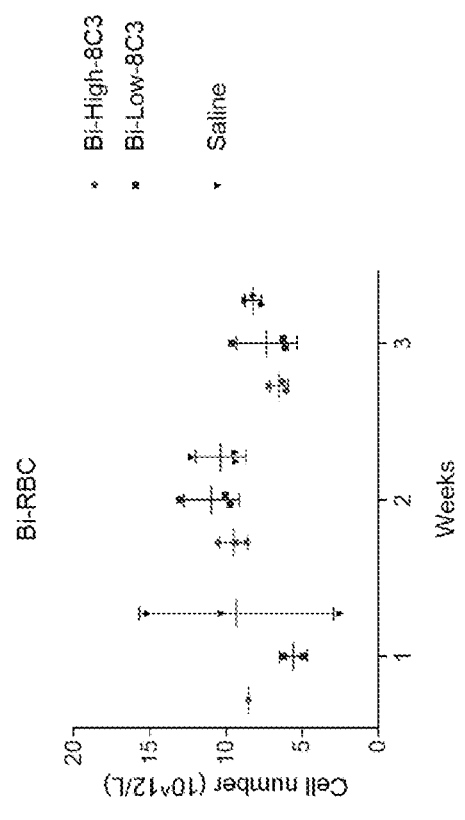
FIG. 12 and FIG. 13 are a series of graphs depicting blood counts of 12A and 13A) white blood cells, 12B and 13B) red blood cells, 12C and 13C) and platelets in mice treated with either: high dose of 213Bi-h8C3 HE-5, or low dose of 213Bi-h8C3 HE-5, or high dose of 177Lu-h8C3 HE-5, or low dose of 177Lu-h8C3 HE-5, or 80 µg unlabeled ("cold") h8C3 HE-5, or left untreated.
Figure 12B:
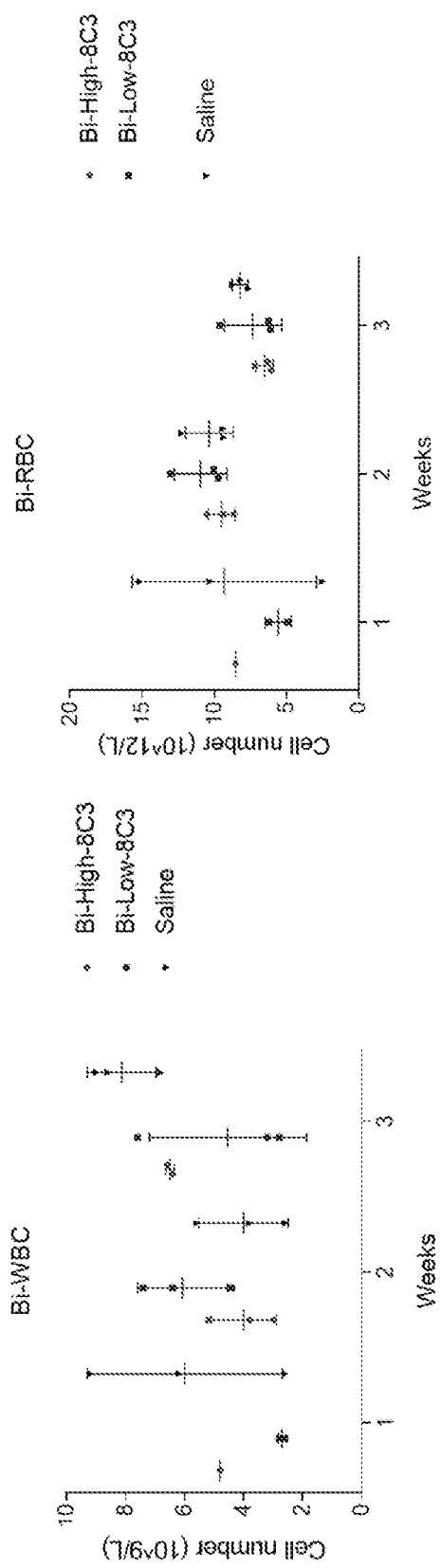
Figure 12C:
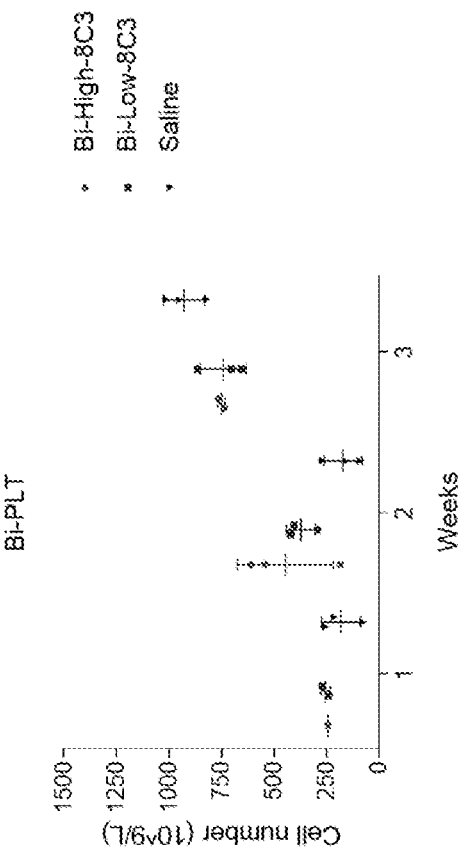
Figure 13B:
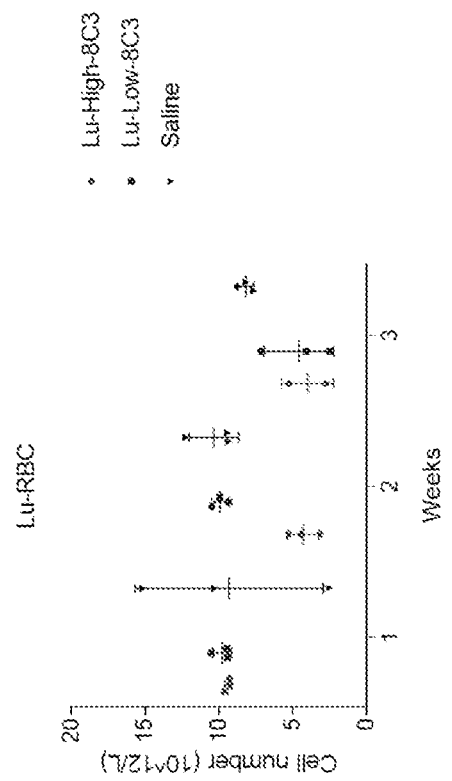
Figure 13A:
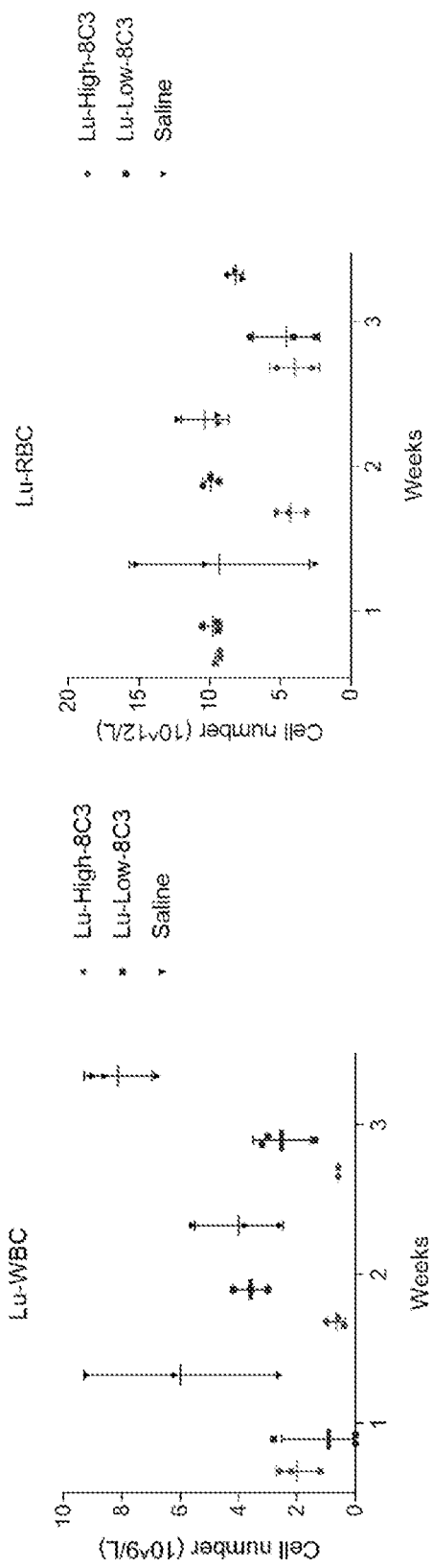
Figure 13C:
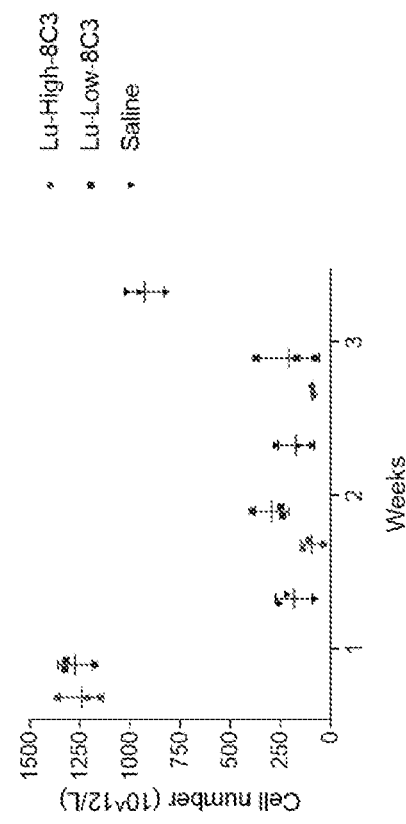
Figure 15A:
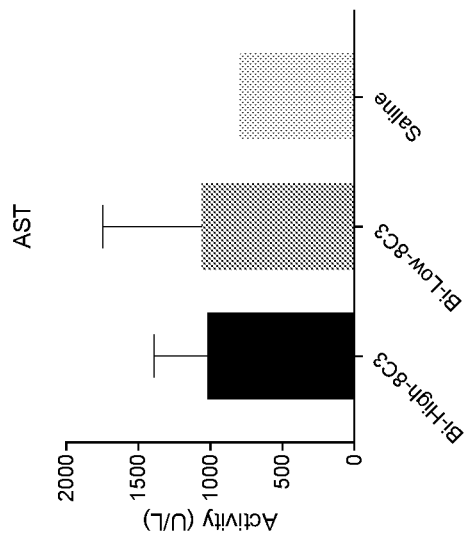
FIG. 15 is a series of graphs depicting concentrations of blood analytes: 15A) alanine transaminase (ALT), 15B)
Figure 15B:
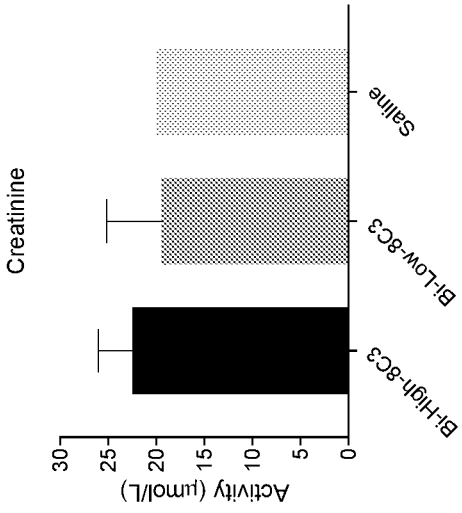
Figure 15C:
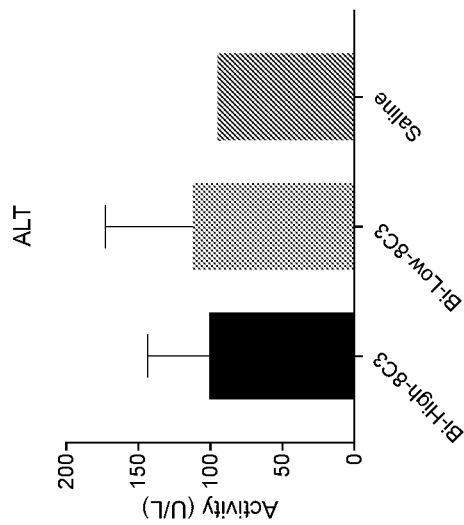
Figure 15D:
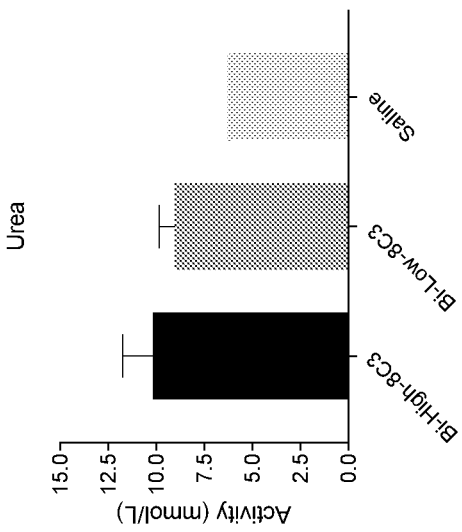

Female C57B16 mice were injected with 5×105 B16-10 melanoma cells into the right flank as described in example 3. The mice were used for therapy when their tumors reached approximately 50 mm³. The mice were randomized into the group of five animals and treated with either: high dose of 213Bi-h8C3 HE-5, or low dose of 213-h8C3 HE-5, or high dose of 177Lu-h8C3 HE-5, or low dose of 177Lu-h8C3 HE-5, or 80 µg unlabeled ("cold") h8C3 HE-5, or left untreated. Their tumors were measured every three days with electronic calipers to calculate the tumor volume for 21 day (FIGS. 11A and 11B). The mice were weighed every 3 days (FIGS. 14A and 14B). Their blood was analyzed on a weekly basis for white blood cells (FIGS. 12A and 13A), red blood cells (FIGS. 12B and 13B) and platelet count (FIGS. 12C and 13C). At the completion of the experiment mice were sacrificed and their blood was analyzed for ALT (FIG. 15A), AST (FIG. 15B), urea (FIG. 15C) and creatinine (FIG. 15D).

The 213Bi- and 177Lu-labeled h8C3 HE-5 antibody efficacy in radioimmunotherapy of B16-F10 melanoma were compared. The results of the experiments demonstrated that short-lived (46 min physical half-life) alpha-emitter 213Bi was much more efficient in killing melanoma cells than long-lived (6.7 days physical half-life) beta-emitter 177Lu. Without being bound to any theory, the superior efficiency of 213Bi delivered by h8C3 HE-5 to the melanoma tumors may be explained by a better match between fast dose rate of 213Bi decay and aggressive growth of B16-F10 cells (doubling time 7 hrs) while slower decaying 177Lu needs a longer time to deliver its radiation dose and cannot match this cell growth. The relative biological effectiveness (RBE) of alpha-particles emitted by 213Bi is several times higher than that of beta-particles, thus resulting in more efficient tumor control.

Example 7: Fractionation Therapy with 213Bi-h8C3 HE-5

Figure 18A:
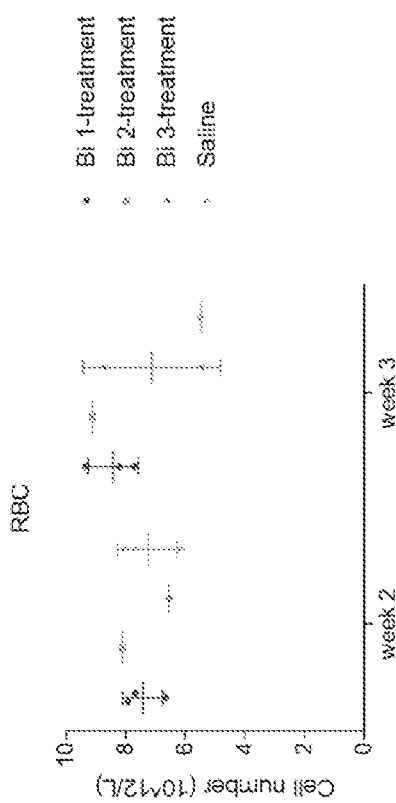
Figure 18B:
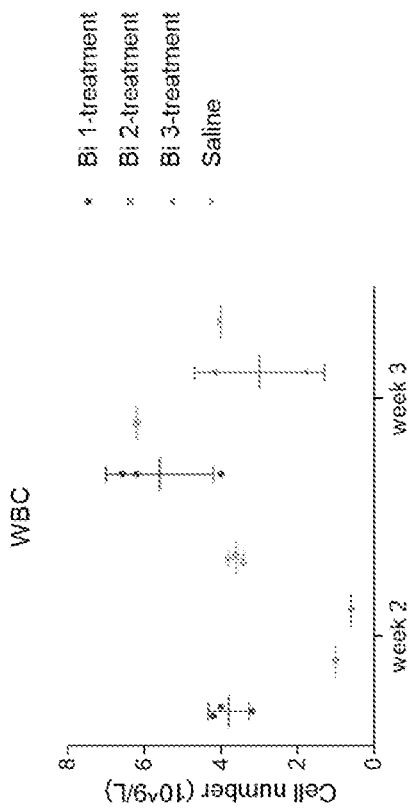
Figure 18C:
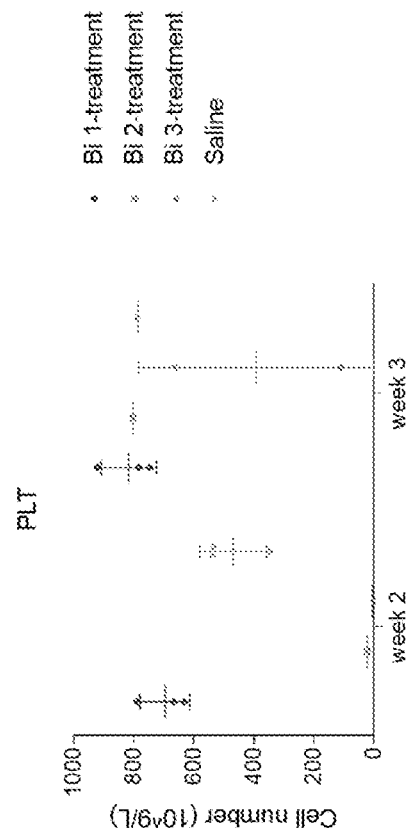
Figure 19A:
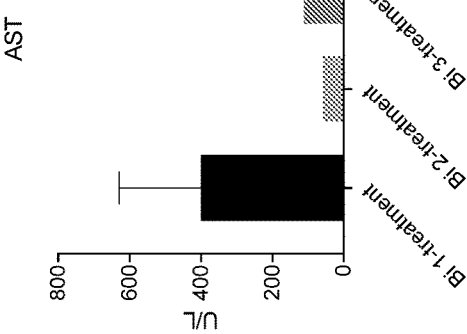
Figure 19B:
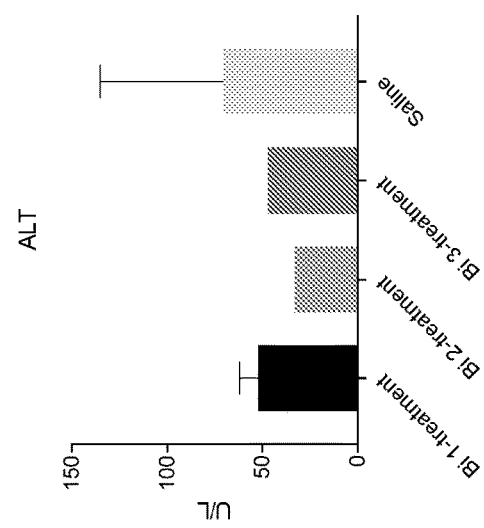
Figure 19C:
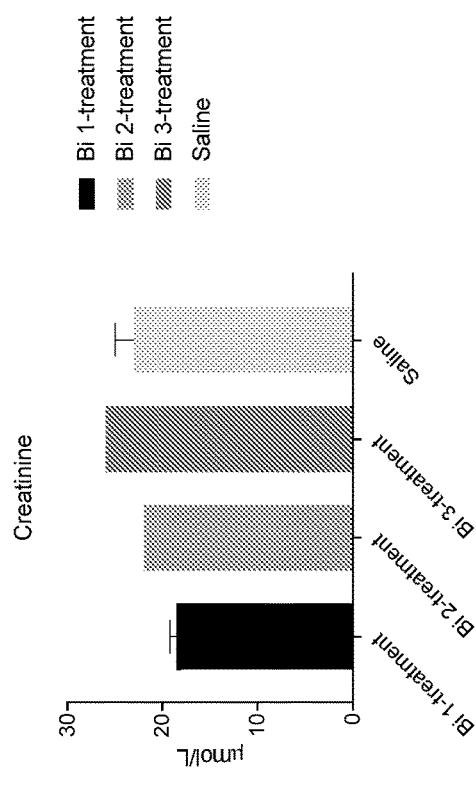
Figure 19D:
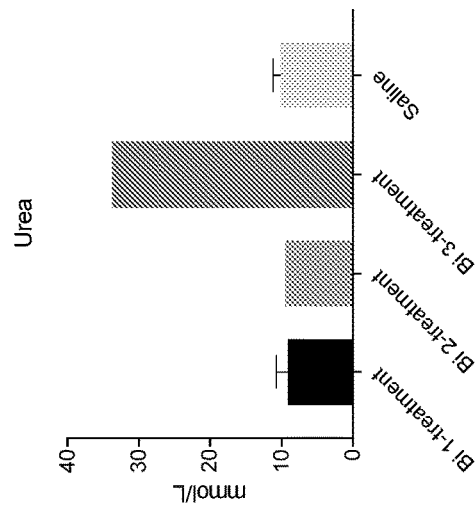

The same murine melanoma model as in Comparative Treatment was used. h8C3 HE-5 antibody was radiolabeled with 213Bi as in Comparative treatment. Tumor-bearing mice were randomized into the groups of 8 and treated with either: single dose 400 µCi 213-h8C3 HE-5 on Day 0, or 400 µCi 213-h8C3 HE-5 on Day 0 and on Day 3, or 400 µCi 213-h8C3 HE-5 on Day 0, Day 3 and Day 7. On Day 16 mice in the single dose group were treated with another 400 µCi 213-h8C3 HE-5 dose. Changes in tumor volume are depicted in FIGS. 16A, 16B, and 16C. Changes in mouse body weight are depicted in FIG. 17. Comparative blood counts for white blood cells, red blood cells, and platelets are depicted in FIGS. 18A, 18B, and 18C, respectively. Systemic toxicity to the kidney and liver are depicted in FIG. 19.

Example 8: microSPECT/CT Imaging of B16-F10 Melanoma Tumor Bearing Mice with 111In-h8C3 HE-5

The mouse model and radiolabeling with 111In of h8C3 HE-5 antibody were performed as described. microSPECT/CT (micro single photon emission computer tomography/computer tomography) images were collected on a MILabs VECTor4 (Netherlands) microSPECT/CT scanner and processed using the comprehensive image analysis software package PMOD (version 3.9, PMOD Technologies, Inc, Switzerland). Imaging studies were conducted using 200 µCi 111In at a 5:1 mCi/mg specific activity with a CHXA" conjugated h8C3 HE-5. Two tumor-bearing mice were injected IV via tail vein and imaged in the prone position at 1, 24, 48, 72, and 216 hours post injection (FIG. 20). SPECT data was collected for 20 minutes using an Extra Ultra High Sensitivity Mouse (XUHS-M) collimator for 20-350 keV range using spiral trajectories. All SPECT images were reconstructed using both 245 keV and 171 keV 111In gamma emissions on a 0.4 mm voxel grid with MILabs reconstruction software.

Example 9: Generation of Recombinant Cell Lines Expressing 8C3 HE-5 Antibody

CHO DG44 host cells were transfected with vectors encoding h8C3 HE-5 antibody. Transfectants were selected and subjected to one round of subcloning by limited dilution. Three subclones were selected for the generation of Research Cell Banks ("RCBs") designated as follows: SUBCLONE-2-3H2, SUBCLONE-2-20C3, and SUBCLONE-2-3H11.

Transfection and Generation of Bulk Pools and Mini-Pools
Transfection of DHFR-Deficient CHO DG44

The dihydrofolate reductase (DHFR)-deficient CHO DG44 cell line used as a host for the recombinant cell lines described here is an auxotroph for hypoxanthine and thymidine (HT) that was developed by Dr. Larry Chasin of Columbia University. The DHFR-CHO line was derived from EMS and γ-radiation-induced mutations of the CHO K1 cell line ATCC CCL-61. The ATCC CCL-61 cell line is a proline auxotroph of a cell line established from *Cricetulus griseus* ovarian tissue by Dr. Ted Puck in 1958. Dr. Chasin used two rounds of γ-radiation to produce a cell line completely lacking both alleles of the DHFR gene.

The DHFR-cell lines DUXB11 and DG44 have been used since 1981 for the production of recombinant proteins. More recently, the DG44 cell line has been adapted to grow in chemically defined, serum-free medium as a suspension cell line. Aragen obtained the suspension-adapted DG44 cells as a frozen culture from Invitrogen in 2008 (Gibco-Invitrogen, Cat 12609-012, lot number 288885). The cells were expanded in CHO DG44 medium (Invitrogen), a chemically defined medium, and frozen down in a mixture of that medium and 7.5% cell culture grade DMSO (Sigma). The cells were passaged in antibiotic-free medium three times and tested by NAMSA for Bacteriostasis/Fungistasis and sterility, by Research Animal Diagnostic Laboratory (RADIL) for IMPACT VII PCR profile, and by Bionique Testing Laboratories, Inc. for *mycoplasma*. The cells met the specified test requirements.

The plasmids, pAB2-8C3-HE-LRLC (VK1) (625.82.2 [PvuI]) and pAB11-8C3-HE-LRMRHC (VH3) (625.85.5 [PvuI]) encoding (respectively) the antibody heavy and light chain are described herein. The plasmids also encode DHFR and neomycin selectable markers, respectively. The plasmids were linearized by overnight digestion with the restriction enzyme PvuI followed by phenol-chloroform and ethanol precipitation. Plasmid DNA was re-suspended in 0.1×TE buffer and the concentration measured at 260 nm. The DNA was adjusted to 1 μg/μL by the addition of sterile 0.1×TE buffer.

Nine sets of Neon electroporations using 1/1 vector ratios were performed in DG44 host cells. For each transfection, a total amount of 10 μg of DNA was added to 100 μL of CHO DG44 cells suspended in Resuspension Buffer R at a concentration of 4.0×106 cells/mL. The DNA/cell mixture was drawn into a Neon tip 100 and electroporated using the Neon electroporation device from Invitrogen with a 1700 V×20 ms×1 pulse program. In parallel with these nine transfections, one set of transfection was performed using Aragen A B2 vector carrying the GFP sequence. Promptly following electroporation, the transfected cells were diluted into 2 mL of CD-DG44 medium supplemented with 8 mM Glutamax in a 6-well plate and cultured in static condition at 37° C. and 5% $CO_2$. Transfection efficiency was measured by FACS analysis of the GFP transfected cells, 72 hours after transfection. Seventy-two hours after transfection, forty six percent of the cells transfected with the GFP carrying DNA were positive for GFP by FACS analysis, which corresponded to the average transient transfection efficiency expected at that stage.

Three days after electroporation, the cells from the nine wells for each transfection were pooled and media exchanged into CD-OptiCHO (HT deficient)+8 mM Glutamax. Next, the pools were used to generate two types of stable selected pools (bulk pools and mini-pools).

Generation of Bulk Pools

Bulk pools were generated as a way to obtain CHO derived materials within a relatively short period of time (~3-4 weeks). One bulk pool was generated with gradual increase of G418 (0.25 mg/mL→0.5 mg/mL final) and auxotrophic DHFR selection with HT deficient medium in static flasks. The bulk pool was adapted into shake flasks upon recovery of cell viability to ~90%.

Further, the performance of the pool was assessed in shake flasks by seeding 125 mL shake flasks at 5×105 cells/mL in 50 mL of CD-OptiCHO media supplemented with 8 mM Glutamax. The shake flask was cultured at 37° C. and 5% $CO_2$, on a shaker platform equipped with a 25 mm orbital throw set up at 125 rpm. The cultures were fed with 5% (initial culture volume) of Cell Boost 7a with 10 mg/L Invitrogen recombinant human insulin and 0.5% of Cell Boost 7b (initial culture volume) from Hyclone on Days 3 and 6 and 8. Cell number was counted (FIG. 21) and conditioned media were taken on Days 3, 6, 8 and daily after Day 9. Cultures were harvested at ~80% viability by centrifuging at 2500 rpm for 5 min on day 11. The protein concentration in the conditioned media was measured by ForteBio Octet Red with a Protein A sensor using a purified IgG1 antibody as a standard. The expression levels obtained from the pools are presented on FIG. 22.

Lastly, the 8C3 HE-5 antibody in the condition media was purified on Protein A drip column, the purification fractions were analyzed by SDS-PAGE.

Generation of Mini-Pools

Mini-pools were generated three days after transfection by plating the transfected pools into mini-pools at 1,000 cells per well under auxotrophic DHFR selection in CD-OptiCHO medium supplemented with 8 mM Glutamax (18×96-well plates) in 200 μl of medium, plates were cultured at 37° C. and 5% $CO_2$. Beginning three days after plating, the mini-pools were subjected to a gradual increase of G418 concentration (0.25 mg/mL→0.5 mg/mL final) and methotrexate (MTX) (100 nM→200 nM→400 nM final) through media exchange over a 4-week period. Cell confluence was monitored by microscope during this time with higher selection applied upon cell growth (i.e., increase in cell confluence). After ~5 weeks, the plates were assayed by ELISA using Goat-anti-Human IgG-Fc and Goat-anti-Human kappa chain-HRP as coating and detecting antibodies, respectively (FIG. 23).

The 120-top expresser mini-pools obtained from the 96-well plate screening were expanded to 24-well plates and re-screened for expression in 24-well plates. Cells were plated in new 24-well plates at approximately 20% confluence in fresh media in CD-OptiCHO supplemented with 8 mM Glutamax. Condition media were collected on Day 7 and 11. The protein concentration in the conditioned media was measured by ForteBio Octet Red with a Protein A sensor using the 8C3 HE-5 antibody purified from the bulk pool as standard (FIG. 24).

After screening, the highest 24-well plates expresser mini-pools were pooled in three super pools. The list of mini-pools selected for the three super-pools is presented in the FIG. 25. Super-pool 1 was composed of the three highest expresser mini-pools with titers ranging from 106 to 129 μg/mL, the Super-pool 2 was composed of five mini-pools with titers ranging from 60 to 75 μg/mL and the Super-pool 3 was composed of seven mini-pools with titers ranging from 40 to 58 μg/mL.

The Super-Pools were passaged in CD-OptiCHO medium supplemented with 8 mM Glutamax, 0.5 mg/mL G418 and 400 nM MTX for approximately 2 weeks until viability approached 85%. At that time, the Super-pools were cryopreserved, processed with limited dilution and evaluated in fed batch shaker flasks for expression.

Shake Flasks Evaluation of the Super Pools.

The super-pools were evaluated in fed batch shake flasks. Cells were seeded at 5×105 cells/mL in 50 mL of CD-OptiCHO medium supplemented with 8 mM L-glutamine, in 250 ml shake flasks. The shake flasks were cultured at 37° C. and 5% $CO_2$, on a shaker platform equipped with a 25 mm orbital throw rotating at 125 rpm. The cultures were fed with 5% of Cell Boost 7a supplemented with 10 mg/L Invitrogen recombinant human insulin and 0.5% of Cell Boost 7b, daily on Day 3, 6, 8 and 10. NOVA readings were performed on Days 3, 6, 8 and as needed until harvest to monitor and adjust for glucose and L-glutamine. Cell counts, and samples of cultures were taken on Days 3, 6, 8, 10 and everyday thereafter until harvest. The cultures were harvested at <80% viability. The growth curve and viability are presented in the FIGS. 26 and 27. Super-pool-1 adapted slower than cells from Super-pool-2 and -3 to suspension growth in shake flasks, as a consequence two runs of fed batch evaluations were performed for Super-pool-1. The expression profiles are presented in the FIG. 28 below. The highest expression, 792.3 mg/L, was obtained with Super-pool-1 repeat and super-pool 2 had 462 mg/L.

Limited Dilution of Mini-Pool Derived Super-Pools

Limited Dilution and ELISA Screening Clones

Three super-pools were cloned by limited dilution method. Each culture was seeded in 96-well plates at 0.5 cells/well. Twenty 96-well plates were plated for each superpool. Cloning medium were composed of CD OptiCHO supplemented with 8 mM Glutamax, 2 mM Glutamine, 5 µg/mL Insulin, 1×HT and equal volume of condition medium collected from bulk pool culture. Plates were incubated in a static incubator at 37° C. with 5% $CO_2$ for 14 days and each well was imaged on Day 0, 1, 2, 5 or 7 and day 13 or 14 by Solentim Imaging System. Fresh medium, 100 µL, was added into each well on Day 7 and medium were changed on Day 14. After fourteen or fifteen days incubation, all plates were screened by ELISA using Goat-anti-Human IgG-Fc and Goat-anti-Human kappa chain-HRP as coating and detecting antibodies, respectively.

Based on Solentim images and ELISA screening results, the top 135 clones, originated from single cells were expanded up to 24-well plates in CD-OptiCHO medium supplemented with 8 mM Glutamax, 0.5 mg/mL G418 and 400 nM MTX.

The top 135 clones expanded to 24-well plates were monitored periodically with a microscope. After approximately 7 days, the wells reached 80% confluence. At this time, each clone was seeded at 20% confluence in fresh media in a well of a new 24-well plate. Cultures were incubated for 11 days in static conditions at 37° C. and 5% $CO_2$. Condition media were collected on day 7 and 11. Clones were ranked based on expression levels measured on day 11 using a ForteBio Octet Red with a Protein A sensor and compared to a standard curve obtained with the 8C3 HE-5 antibody purified from the bulk pool (FIG. 29). Based on the 24-well expression level profile, a total of 36 clones with expression levels range from 95.7 to 221.8 µg/mL were expanded into T-75 and subsequently into 125 mL shake flasks. The expression level of the top 36 clones in 24 well stage is summarized in FIG. 30.

The top 36 clones expanded to shake flasks were cryo-preserved (3 vials each) in 7.5% DMSO and 92.5% CD-OptiCHO media. The vials were placed into Nalgene Cryo 1° C. Freezing. Container (−1° C./minute cooling rate) and stored at −80° C. After 48 hours, the vials were transferred and stored in a liquid nitrogen tank.

Shake Flask Evaluation of Top Clones

Thirty-five of the thirty-six top expressers sub-clones identified at the 24 well plates stage successfully adapted to suspension growth in shake flasks. These top sub-clones were evaluated for expression in 250 mL shake flasks in fed batch conditions. Shake flasks were seeded at 5×105 cells/mL in 50 mL of CD-OptiCHO medium supplemented with 8 mM L-glutamine. The shake flasks were cultured at 37° C. and 5% $CO_2$, on a shaker platform equipped with a 25 mm orbital throw rotating at 125 rpm. The cultures were fed with 5% of Cell Boost 7a and 0.5% of Cell Boos 7b, daily on Day 3, 6, 8 and 10. NOVA readings were performed on Days 3, 6, 8 and daily as needed until harvest to monitor and adjust for glucose and L-glutamine. Meanwhile, cell counts, and samples of cultures were taken on Days 3, 6, 8, 10 and daily thereafter until harvest. The cultures were harvested at <80% viability. Cells were centrifuged at 2500 rpm for 5 min and conditioned medium transferred and stored at −20° C.

Clones 2-3H2, 2-3H11, 2-11H12 and 2-20C3 reached the highest expression levels with respective expression levels of 1.29 g/L, 1.27 g/L, 1.26 g/L, and 1.25 g/L. Maximum Viable Cell Density (VCD), viability profile, titer at harvest, longevity of the cultures and clonality analyzed from Solentim images were summarized in FIG. 31.

Clones 2-3H2, 2-3H11 and 2-20C3 highlighted in FIG. 31 and were selected for the preparation of the research cell banks.

The harvest conditioned medium obtained from the five top expresser clones were analyzed by SDS-PAGE. Four microliters were loaded on each band in reduced and non-reduced condition. Expected molecular weight bands were obtained in reduced and non-reduced conditions with all five clones.

Preparation of Research Cell Banks

Clones 2-3H11, 2-3H3 and 2-20C3 were selected for the preparation of Research Cell Banks (RCB), based on their expression level at harvest and clonality from Solentim.

Each clone was expanded into 250 mL and RCB was prepared by banking 36 vials with 1×107 viable cells in 1 mL volume of 7.5% DMSO and 92.5% CD-OptiCHO media supplemented with 8 mM GlutaMax per vial. The vials were placed into Nalgene Cryo 1° C. Freezing Container (−1° C./minute cooling rate) and stored at −80° C. All vials were transferred and stored in a liquid nitrogen tank after 48 hours.

The invention claimed is:

1. A monoclonal antibody that specifically binds to melanin, wherein the antibody comprises:
   (a) a heavy chain comprising the amino acid sequence of SEQ ID NO: 2 and a light chain comprising the amino acid sequence of SEQ ID NO: 1;
   (b) a heavy chain comprising the amino acid sequence of SEQ ID NO: 3 and a light chain comprising the amino acid sequence of SEQ ID NO: 5;
   (c) a heavy chain comprising the amino acid sequence of SEQ ID NO: 3 and a light chain comprising the amino acid sequence of SEQ ID NO: 6;
   (d) a heavy chain comprising the amino acid sequence of SEQ ID NO: 3 and a light chain comprising the amino acid sequence of SEQ ID NO: 7;
   (e) a heavy chain comprising the amino acid sequence of SEQ ID NO: 4 and a light chain comprising the amino acid sequence of SEQ ID NO: 5;
   (f) a heavy chain comprising the amino acid sequence of SEQ ID NO: 4 and a light chain comprising the amino acid sequence of SEQ ID NO: 6; or
   (g) a heavy chain comprising the amino acid sequence of SEQ ID NO: 4 and a light chain comprising the amino acid sequence of SEQ ID NO: 7.

2. The antibody of claim 1, wherein the antibody comprises a heavy chain comprising the amino acid sequence of SEQ ID NO: 2 and a light chain comprising the amino acid sequence of SEQ ID NO: 1.

3. The antibody of claim 1, wherein the antibody comprises a heavy chain comprising the amino acid sequence of SEQ ID NO: 3 and a light chain comprising the amino acid sequence of SEQ ID NO: 5.

4. The antibody of claim 1, wherein the antibody comprises a heavy chain comprising the amino acid sequence of SEQ ID NO: 3 and a light chain comprising the amino acid sequence of SEQ ID NO: 6.

5. The antibody of claim 1, wherein the antibody comprises a heavy chain comprising the amino acid sequence of SEQ ID NO: 3 and a light chain comprising the amino acid sequence of SEQ ID NO: 7.

6. The antibody of claim 1, wherein the antibody comprises a heavy chain comprising the amino acid sequence of SEQ ID NO: 4 and a light chain comprising the amino acid sequence of SEQ ID NO: 5.

7. The antibody of claim 1, wherein the antibody comprises a heavy chain comprising the amino acid sequence of SEQ ID NO: 4 and a light chain comprising the amino acid sequence of SEQ ID NO: 6.

8. The antibody of claim 1, wherein the antibody comprises a heavy chain comprising the amino acid sequence of SEQ ID NO: 4 and a light chain comprising the amino acid sequence of SEQ ID NO: 7.

9. The antibody of claim 1, wherein the antibody is an antigen binding fragment.

10. The antibody of claim 1, wherein the antibody is a bispecific antibody.

11. The antibody of claim 10, wherein the bispecific antibody comprises a first arm that targets melanin and a second arm that targets an antigen comprising an immune checkpoint.

12. The antibody of claim 11, wherein the immune checkpoint is CTLA4, PD-1, or PD-L1.

13. The antibody of claim 1, wherein the antibody is conjugated to an agent.

14. The antibody of claim 13, wherein the agent is a radionuclide.

15. The antibody of claim 14, wherein the radionuclide is 213-Bi.

16. The antibody of claim 14, wherein the radionuclide is 177-Lu.

17. The antibody of claim 13, wherein the agent is conjugated to the antibody through a linker.

18. A kit comprising the antibody of claim 1.

19. A pharmaceutical composition comprising the antibody of claim 1 and a pharmacologically acceptable carrier.

20. A method for treating melanoma in a subject, comprising administering a therapeutically effective amount of the composition of claim 19 to a subject in need thereof.

21. One or more polynucleotides encoding the amino acid sequences of an antibody of claim 1.

* * * * *

SEQUENCE LISTING

<160> NUMBER OF SEQ ID NOS: 38

<210> SEQ ID NO 1
<211> LENGTH: 218
<212> TYPE: PRT
<213> ORGANISM: Artificial Sequence
<220> FEATURE:
<223> OTHER INFORMATION: Light Chain of a melanin Chimeric Antibody
      (8C3-hKappa)

<400> SEQUENCE: 1

Asp Ile Leu Met Thr Gln Ser Pro Ala Ser Leu Ala Val Ser Leu Gly
1               5                   10                  15

```
Gln Arg Ala Thr Ile Ser Cys Arg Ala Ser Glu Ser Val Asp Ser Tyr
                20                  25                  30

Gly Thr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 2
<211> LENGTH: 453
<212> TYPE: PRT
<213> ORGANISM: Artificial Sequence
<220> FEATURE:
<223> OTHER INFORMATION: Heavy Chain of a melanin Chimeric Antibody
      (8C3-hIgG1)

<400> SEQUENCE: 2

Glu Val Gln Leu Glu Glu Ser Gly Gly Gly Leu Val Gln Pro Gly Gly
1               5                   10                  15

Ser Met Lys Val Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Ala His Asn His Ala Thr Tyr Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Thr Tyr
                85                  90                  95

Tyr Cys Thr Arg Gly Gly Tyr Tyr Gly Asn Tyr Gly Phe Phe Ala Tyr
            100                 105                 110

Trp Gly Gln Gly Thr Leu Val Thr Val Ser Ala Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
```

```
                145                 150                 155                 160
            Thr Val Ser Trp Asn Ser Gly Ala Leu Thr Ser Gly Val His Thr Phe
                                165                 170                 175

Pro Ala Val Leu Gln Ser Ser Gly Leu Tyr Ser Leu Ser Ser Val Val
                            180                 185                 190

Thr Val Pro Ser Ser Ser Leu Gly Thr Gln Thr Tyr Ile Cys Asn Val
                        195                 200                 205

Asn His Lys Pro Ser Asn Thr Lys Val Asp Lys Val Glu Pro Lys
                    210                 215                 220

Ser Cys Asp Lys Thr His Thr Cys Pro Pro Cys Pro Ala Pro Glu Leu
            225                 230                 235                 240

Leu Gly Gly Pro Ser Val Phe Leu Phe Pro Pro Lys Pro Lys Asp Thr
                                245                 250                 255

Leu Met Ile Ser Arg Thr Pro Glu Val Thr Cys Val Val Val Asp Val
                            260                 265                 270

Ser His Glu Asp Pro Glu Val Lys Phe Asn Trp Tyr Val Asp Gly Val
                        275                 280                 285

Glu Val His Asn Ala Lys Thr Lys Pro Arg Glu Glu Gln Tyr Asn Ser
                    290                 295                 300

Thr Tyr Arg Val Val Ser Val Leu Thr Val Leu His Gln Asp Trp Leu
            305                 310                 315                 320

Asn Gly Lys Glu Tyr Lys Cys Lys Val Ser Asn Lys Ala Leu Pro Ala
                                325                 330                 335

Pro Ile Glu Lys Thr Ile Ser Lys Ala Lys Gly Gln Pro Arg Glu Pro
                            340                 345                 350

Gln Val Tyr Thr Leu Pro Pro Ser Arg Asp Glu Leu Thr Lys Asn Gln
                        355                 360                 365

Val Ser Leu Thr Cys Leu Val Lys Gly Phe Tyr Pro Ser Asp Ile Ala
                    370                 375                 380

Val Glu Trp Glu Ser Asn Gly Gln Pro Glu Asn Asn Tyr Lys Thr Thr
            385                 390                 395                 400

Pro Pro Val Leu Asp Ser Asp Gly Ser Phe Phe Leu Tyr Ser Lys Leu
                                405                 410                 415

Thr Val Asp Lys Ser Arg Trp Gln Gln Gly Asn Val Phe Ser Cys Ser
                            420                 425                 430

Val Met His Glu Ala Leu His Asn His Tyr Thr Gln Lys Ser Leu Ser
                        435                 440                 445

Leu Ser Pro Gly Lys
                    450

<210> SEQ ID NO 3
<211> LENGTH: 453
<212> TYPE: PRT
<213> ORGANISM: Artificial Sequence
<220> FEATURE:
<223> OTHER INFORMATION: Heavy Chain of a melanin Humanized Antibody
      (8C3-HE-VH3A-hIgG1)

<400> SEQUENCE: 3

Glu Val Gln Leu Val Glu Ser Gly Gly Gly Leu Val Gln Pro Gly Gly
            1               5                   10                  15

Ser Met Arg Val Ser Cys Ala Ala Ser Gly Phe Thr Phe Ser Asp Ala
                            20                  25                  30

Trp Met Asp Trp Val Arg Gln Ala Pro Gly Lys Gly Leu Glu Trp Val
                        35                  40                  45
```

```
Ala Glu Ile Arg Ser Lys Ala His Asn His Ala Thr Tyr Tyr Ala Glu
 50                  55                  60
Ser Val Lys Gly Arg Phe Thr Ile Ser Arg Asp Asp Ser Lys Ser Thr
 65                  70                  75                  80
Val Tyr Leu Gln Met Asn Ser Leu Arg Ala Glu Asp Thr Gly Thr Tyr
                 85                  90                  95
Tyr Cys Thr Arg Gly Gly Tyr Gly Asn Tyr Gly Phe Phe Ala Tyr
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
                435                 440                 445
Leu Ser Pro Gly Lys
450
```

```
<210> SEQ ID NO 4
<211> LENGTH: 453
<212> TYPE: PRT
<213> ORGANISM: Artificial Sequence
<220> FEATURE:
<223> OTHER INFORMATION: Heavy Chain of a melanin Humanized Antibody
      (8C3-HE-VH3B-hIgG1)

<400> SEQUENCE: 4

Glu Val Gln Leu Val Glu Ser Gly Gly Gly Leu Val Gln Pro Gly Gly
1               5                   10                  15

Ser Met Arg Val Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala His Asn His Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Gly Val Tyr
                85                  90                  95

Tyr Cys Thr Arg Gly Gly Tyr Tyr Gly Asn Tyr Gly Phe Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365
```

-continued

```
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450
```

<210> SEQ ID NO 5
<211> LENGTH: 218
<212> TYPE: PRT
<213> ORGANISM: Artificial Sequence
<220> FEATURE:
<223> OTHER INFORMATION: Light Chain of a melanin Humanized Antibody
    (8C3-HE-VK1A-hKappa)

<400> SEQUENCE: 5

```
Asp Ile Gln Met Thr Gln Ser Pro Ser Ser Leu Ser Val Ser Leu Gly
1               5                   10                  15

Asp Arg Ala Thr Ile Thr Cys Arg Ala Ser Glu Ser Val Asp Ser Tyr
            20                  25                  30

Gly Thr Ser Phe Met His Trp Tyr Gln Gln Lys Pro Gly Lys Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Pro Val Gln Ala Glu Asp Phe Ala Thr Tyr Tyr Cys Gln Gln Asn Asn
                85                  90                  95

Glu Tyr Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 6
<211> LENGTH: 218
<212> TYPE: PRT
<213> ORGANISM: Artificial Sequence
<220> FEATURE:
<223> OTHER INFORMATION: Light Chain of a melanin Humanized Antibody
    (8C3-HE-VK1B-hKappa)

<400> SEQUENCE: 6

```
Asp Ile Gln Met Thr Gln Ser Pro Ser Ser Leu Ser Val Ser Val Gly
1               5                   10                  15

Asp Arg Ala Thr Ile Thr Cys Arg Ala Ser Glu Ser Val Asp Ser Tyr
            20                  25                  30

Gly Thr Ser Phe Met His Trp Tyr Gln Gln Lys Pro Gly Lys Pro Pro
        35                  40                  45

Lys Leu Leu Ile Tyr Leu Ala Ser Asn Leu Gln Ser Gly Val Pro Ser
    50                  55                  60

Arg Phe Ser Gly Ser Gly Ser Arg Thr Asp Phe Thr Leu Thr Ile Ser
65                  70                  75                  80

Pro Val Gln Ala Glu Asp Phe Ala Thr Tyr Tyr Cys Gln Gln Asn Asn
                85                  90                  95

Glu Tyr Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 7
<211> LENGTH: 218
<212> TYPE: PRT
<213> ORGANISM: Artificial Sequence
<220> FEATURE:
<223> OTHER INFORMATION: Light Chain of a melanin Humanized Antibody
(8C3-HE-VK4-hKappa)

<400> SEQUENCE: 7

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Ser Tyr
            20                  25                  30

Gly Thr Ser Phe Met His Trp Tyr Gln Gln Lys Pro Gly Gln Pro Pro
        35                  40                  45

Lys Leu Leu Ile Tyr Leu Ala Ser Asn Arg Glu Ser Gly Val Pro Asp
    50                  55                  60

Arg Phe Ser Gly Ser Gly Ser Arg Thr Asp Phe Thr Leu Thr Ile Ser
65                  70                  75                  80

Pro Val Gln Ala Glu Asp Val Ala Thr Tyr Tyr Cys Gln Gln Asn Asn
                85                  90                  95

Glu Tyr Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 8
<211> LENGTH: 9
<212> TYPE: PRT
<213> ORGANISM: Artificial Sequence
<220> FEATURE:
<223> OTHER INFORMATION: VH CDR1

<400> SEQUENCE: 8

Phe Thr Phe Ser Asp Ala Trp Met Asp
1               5

<210> SEQ ID NO 9
<211> LENGTH: 16
<212> TYPE: PRT
<213> ORGANISM: Artificial Sequence
<220> FEATURE:
<223> OTHER INFORMATION: VH CDR2

<400> SEQUENCE: 9

Trp Val Ala Glu Ile Arg Ser Lys Ala His Asn His Ala Thr Tyr Tyr
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: VH CDR3

<400> SEQUENCE: 10

Arg Gly Gly Tyr Tyr Gly Asn Tyr Gly Phe Phe Ala Tyr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: VL CDR1

<400> SEQUENCE: 11

Glu Ser Val Asp Ser Tyr Gly Thr Ser Phe Met His
1               5                   10

<210> SEQ ID NO 12
<211> LENGTH: 11
<212> TYPE: PRT
<213> ORGANISM: Artificial Sequence
<220> FEATURE:
<223> OTHER INFORMATION: VL CDR2
```

```
<400> SEQUENCE: 12

Leu Leu Ile Tyr Leu Ala Ser Asn Leu Glu Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: VL CDR2

<400> SEQUENCE: 13

Leu Leu Ile Tyr Leu Ala Ser Asn Leu Gln Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: VL CDR2

<400> SEQUENCE: 14

Leu Leu Ile Tyr Leu Ala Ser Asn Arg Glu Ser
1               5                   10

<210> SEQ ID NO 15
<211> LENGTH: 8
<212> TYPE: PRT
<213> ORGANISM: Artificial Sequence
<220> FEATURE:
<223> OTHER INFORMATION: VL CDR3

<400> SEQUENCE: 15

Gln Gln Asn Asn Glu Tyr Pro Tyr
1               5

<210> SEQ ID NO 16
<211> LENGTH: 21
<212> TYPE: PRT
<213> ORGANISM: Artificial Sequence
<220> FEATURE:
<223> OTHER INFORMATION: Signal peptide

<400> SEQUENCE: 16

Met Asp Met Arg Val Pro Ala Gln Leu Leu Gly Leu Leu Leu Leu Trp
1               5                   10                  15

Leu Arg Gly Ala Arg
            20

<210> SEQ ID NO 17
<211> LENGTH: 66
<212> TYPE: DNA
<213> ORGANISM: Artificial Sequence
<220> FEATURE:
<223> OTHER INFORMATION: Signal peptide nucleotide sequence

<400> SEQUENCE: 17
atggacatga gagtgccggc gcaactgctc ggcctgctgt tgctgtggct gaggggagcc      60
agatgc                                                                66

<210> SEQ ID NO 18
<211> LENGTH: 1362
<212> TYPE: DNA
<213> ORGANISM: Artificial Sequence
```

```
<220> FEATURE:
<223> OTHER INFORMATION: pAB11 625.69.1 heavy chain of a chimeric
      melanin antibody gene (8C3-hIgG1)

<400> SEQUENCE: 18
gaagtgcagc tcgaggaatc cggaggagga ctggtgcagc ctggcggaag catgaaggtg      60
tcatgcgcgg cttccggatt caccttctcg gacgcctgga tggattgggt cagacaaagc    120
cccgaaaaag gcctggaatg ggtggccgag attcggtcca aggcccataa ccacgccacc    180
tactacgccg agtccgtgaa ggggcgcttt actatctccc gggatgactc gaagtcgtcc    240
gtgtacctcc agatgaactc attgagggcc gaggacactg gacctactac tgtacccgc     300 ggaggctact acgggaacta tggtttcttc gcctactggg gccagggtac cctcgtgact    360
gtcagcgcgg ccagcaccaa gggcccagc gtgttcccac tggcccccaag ctccaagtca    420 acctccggcg gaactgctgc gctgggctgc ttggtgaagg actacttccc cgaaccggtc    480
accgtgtcct ggaacagcgg agccctgacc tcgggagtcc acactttccc cgctgtgctg    540
cagtcgtccg gcctgtactc gctctcgtcc gtggtcactg tcccgtcctc gtccctgggt    600
actcagacct acatttgcaa cgtcaaccac aagccttcaa acacgaaagt ggacaagaag    660
gtcgagccga gtcctgcga caaaacccat acttgccctc cttgtccggc tcccgaactg     720
ctgggcggac cttccgtgtt cctcttcccg cctaagccga agacaccct gatgatcagc     780 aggactccgg aagtgacatg cgtggtggtg gacgtgtcgc acgaggaccc ggaggtcaag    840
tttaattggt acgtggacgg agtggaagtc cacaacgcca agaccaagcc acgggaagaa    900
cagtacaatt ccacctatcg cgtggtgtcc gtgcttaccg tgcttcacca agactggctg    960
aacggaaagg agtacaagtg caaagtgtca aacaaagccc tgcctgcccc aatcgaaaag   1020
accatcagca aggccaaggg gcagcctcgg aaccccaag tgtacactct cccgccgtca    1080
agagatgaac tgaccaagaa ccaagtgtcc ctcacttgtc tcgtgaaggg attctacccc   1140
tccgatatcg ccgtggagtg ggaatccaac gggcaaccg agaacaacta caagaccacc    1200
cctccggtgc ttgattccga tggctccttc ttcctctact ccaagctgac cgtggacaag   1260
tcaagatggc agcagggaa cgtgttctcc tgctccgtca tgcacgaggc cctgcacaac    1320 cattcaccc agaagtctct gtcgctgagc ccgggaaaat aa                        1362

<210> SEQ ID NO 19
<211> LENGTH: 657
<212> TYPE: DNA
<213> ORGANISM: Artificial Sequence
<220> FEATURE:
<223> OTHER INFORMATION: pAB2 625.48.2 light chain of a chimeric melanin
      antibody gene (8C3-hKappa)

<400> SEQUENCE: 19
gacatcctga tgactcagtc acccgctagc cttgcggtgt ccctcggaca acgcgccacc     60
atctcctgtc gggcctccga atccgtggac tcctacggca cctccttcat gcactggtac    120
cagcagaagc caggacagcc tcccaagctg ttgatctatc tggcctcgaa tctggaatca    180
ggagtgccgg ctcggttcag cggctccgga tcacgcactg acttcacgct gaccattgac    240
cccgtggagg cagatgacgc cgcgacctac tactgccagc agaacaacga ataccttac     300 actttcggcg gggtaccaa gctcgaaatc aagcggacag tggcagcccc atcggtgttc    360
atttttccgc cgtcggatga gcagctcaag tccggtactg cctccgtggt ctgcctgctg    420 aacaacttt accctcgcga agcgaaggtc caatggaaag tggataacgc cctccagtcc    480
```
ggaaactccc aggagtctgt caccgagcag gactcaaagg acagcactta ctccctgtcc    540
tcgactctga ccctgtcgaa ggcagattac gagaagcaca aagtgtacgc ctgcgaagtg    600
acccatcaag gccttccag cccggtcacc aagagcttca tcgggggga gtgttag    657

```
<210> SEQ ID NO 20
<211> LENGTH: 726
<212> TYPE: DNA
<213> ORGANISM: Artificial Sequence
<220> FEATURE:
<223> OTHER INFORMATION: Light Chain of a melanin Humanized Antibody
      (8C3-HE-VK4-hKappa)

<400> SEQUENCE: 20
```
atggacatga gagtgccggc gcaactgctc ggcctgctgt tgctgtggct gagggagcc    60 agatgcgaca tcgtgatgac tcagtcaccc gatagccttg cggtgtccct cggagaacgc    120
gccaccatca actgtaaagc ctccgaatcc gtggactcct acggcacctc cttcatgcac    180
tggtaccagc agaagccagg acagcctccc aagctgttga tctatctggc ctcgaatcgg    240
gaatcaggag tgccggaccg gttcagcggc tccggatcac gcactgactt cacgctgacc    300
attagccccg tgcaagcaga ggacgtggcg acctactact gccagcagaa caacgaatac    360
ccttacactt tcggccaggg taccaagctc gaaatcaagc ggacagtggc agccccatcg    420
gtgttcattt tcccgccgtc ggatgagcag ctcaagtccg gtactgcctc cgtggtctgc    480
ctgctgaaca cttttaccc tcgcgaagcg aaggtccaat ggaaagtgga taacgccctc    540
cagtccggaa actcccagga gtctgtcacc gagcaggact caaaggacag cacttactcc    600
ctgtcctcga ctctgaccct gtcgaaggca gattacgaga agcacaaagt gtacgcctgc    660
gaagtgaccc atcaaggcct ttccagcccg gtcaccaaga gcttcaatcg ggggagtgt    720 tagtaa    726

```
<210> SEQ ID NO 21
<211> LENGTH: 726
<212> TYPE: DNA
<213> ORGANISM: Artificial Sequence
<220> FEATURE:
<223> OTHER INFORMATION: Light Chain of a melanin Humanized Antibody
      (8C3-HE-VK1A-hKappa)

<400> SEQUENCE: 21
```
atggacatga gagtgccggc gcaactgctc ggcctgctgt tgctgtggct gagggagcc    60 agatgcgaca tccagatgac tcagtcaccc tcgagcctta gcgtgtccct cggagatcgc    120
gccaccatca cctgtcgggc ctccgaatcc gtggactcct acggcacctc cttcatgcac    180
tggtaccagc agaagccagg aaagcctccc aagctgttga tctatctggc ctcgaatctg    240
gaatcaggag tgccgtcgcg gttcagcggc tccggatcac gcactgactt cacgctgacc    300
attagccccg tgcaagcaga ggactttgcg acctactact gccagcagaa caacgaatac    360
ccttacactt tcggccaggg taccaagctc gaaatcaagc ggacagtggc agccccatcg    420
gtgttcattt tcccgccgtc ggatgagcag ctcaagtccg gtactgcctc cgtggtctgc    480
ctgctgaaca cttttaccc tcgcgaagcg aaggtccaat ggaaagtgga taacgccctc    540
cagtccggaa actcccagga gtctgtcacc gagcaggact caaaggacag cacttactcc    600
ctgtcctcga ctctgaccct gtcgaaggca gattacgaga agcacaaagt gtacgcctgc    660
gaagtgaccc atcaaggcct ttccagcccg gtcaccaaga gcttcaatcg ggggagtgt    720 tagtaa    726

<210> SEQ ID NO 22
<211> LENGTH: 726
<212> TYPE: DNA
<213> ORGANISM: Artificial Sequence
<220> FEATURE:
<223> OTHER INFORMATION: Light Chain of a melanin Humanized Antibody
      (8C3-HE-VK1B-hKappa)

<400> SEQUENCE: 22

```
atggacatga gagtgccggc gcaactgctc ggcctgctgt tgctgtggct gaggggagcc      60
agatgcgaca tccagatgac tcagtcaccc tcgagcctta gcgtgtccgt gggagatcgc     120
gccaccatca cctgtcgggc ctccgaatcc gtggactcct acggcacctc cttcatgcac     180
tggtaccagc agaagccagg aaagcctccc aagctgttga tctatctggc ctcgaatctg     240
cagtcaggag tgccgtcgcg gttcagcggc tccggatcac gcactgactt cacgctgacc     300
attagccccg tgcaagcaga ggactttgcg acctactact gccagcagaa caacgaatac     360
ccttacactt tcggccaggg taccaagctc gaaatcaagc ggacagtggc agccccatcg     420
gtgttcattt tcccgccgtc ggatgagcag ctcaagtccg gtactgcctc cgtggtctgc     480
ctgctgaaca cttttacccc tcgcgaagcg aaggtccaat ggaaagtgga taacgccctc     540
cagtccggaa actcccagga gtctgtcacc gagcaggact caaaggacag cacttactcc     600
ctgtcctcga ctctgaccct gtcgaaggca gattacgaga agcacaaagt gtacgcctgc     660
gaagtgaccc catcaaggcct tccagcccg gtcaccaaga gcttcaatcg gggggagtgt     720
tagtaa                                                                726
```

<210> SEQ ID NO 23
<211> LENGTH: 1428
<212> TYPE: DNA
<213> ORGANISM: Artificial Sequence
<220> FEATURE:
<223> OTHER INFORMATION: Heavy Chain of a melanin Humanized Antibody
      (8C3-HE-VH3A-hIgG1)

<400> SEQUENCE: 23

```
atggacatgc gcgtgccggc acaactgctg gcctgctgc tgctttggct gcggggagct      60
agatgcgaag tgcagctcgt cgaatccgga ggaggactgg tgcagcctgg cggaagcatg     120
cgcgtgtcat gcgcggcttc cggattcacc ttctcgacg cctggatgga ttgggtcaga     180
caagcgcccg gcaaaggcct ggaatgggtg gccgagattc ggtccaaggc cataaccac     240
gccacctact acgccgagtc cgtgaagggg cgctttacta ctcccggga tgactcgaag     300
tcgacggtgt acctccagat gaactcattg agggccgagg acactgggac ctactactgt     360
acccgcggag gctactacgg gaactatggt ttcttcgcct actggggcca gggtaccctc     420
gtgactgtca gcagcgccag caccaagggc cccagcgtgt tcccactggc cccaagctcc     480
aagtcaacct ccggcggaac tgctgcgctg gctgcttgg tgaaggacta cttccccgaa     540
ccggtcaccg tgtcctggaa cagcggagcc ctgacctcgg agtccacac tttccccgct     600
gtgctgcagt cgtccggcct gtactcgctc tcgtccgtgg tcactgtccc gtcctcgtcc     660
ctgggtactc agacctacat ttgcaacgtc aaccacaagc cttcaaacac gaaagtggac     720
aagaaggtcg agccgaagtc ctgcgacaaa acccatactt gccctccttg tccggctccc     780
gaactgctgg gcgacccttc cgtgttcctc ttcccgccta gccgaaaga cacccctgatg     840
atcagcagga ctccggaagt gacatgcgtg gtggtggacg tgtcgcacga ggacccggag     900
```

```
gtcaagttta attggtacgt ggacggagtg aagtccaca acgccaagac caagccacgg    960
gaagaacagt acaattccac ctatcgcgtg gtgtccgtgc ttaccgtgct tcaccaagac   1020
tggctgaacg gaaaggagta caagtgcaaa gtgtcaaaca aagccctgcc tgccccaatc   1080
gaaaagacca tcagcaaggc caaggggcag cctcgggaac cccaagtgta cactctcccg   1140
ccgtcaagag atgaactgac caagaaccaa gtgtccctca cttgtctcgt gaagggattc   1200 taccccctccg atatcgccgt ggagtgggaa tccaacgggc aacccgagaa caactacaag   1260
accacccctc cggtgcttga ttccgatggc tccttcttcc tctactccaa gctgaccgtg   1320
gacaagtcaa gatggcagca ggggaacgtg ttctcctgct ccgtcatgca cgaggccctg   1380
cacaaccatt acacccagaa gtctctgtcg ctgagcccgg gaaaataa              1428

<210> SEQ ID NO 24
<211> LENGTH: 1428
<212> TYPE: DNA
<213> ORGANISM: Artificial Sequence
<220> FEATURE:
<223> OTHER INFORMATION: Heavy Chain of a melanin Humanized Antibody
      (8C3-HE-VH3B-hIgG1)

<400> SEQUENCE: 24
atggacatgc gcgtgccggc acaactgctg ggcctgctgc tgctttggct gcggggagct     60
agatgcgaag tgcagctcgt ggaatccgga ggaggactgg tgcagcctgg cggaagcatg    120
cgcgtgtcat gcgcggcttc cggattcacc ttctcggacg cctggatgga ttgggtcaga    180
caagcgcccg gcaaaggcct ggaatgggtg gccgagattc ggtccaaggc ccataaccac    240
gccacctact acgccgactc cgtgaagggg cgctttacta tctcccggga taactcgaag    300
aataccgtgt acctccagat gaactcattg agggccgagg acactggggt ctactactgt    360
acccgcggag gctactacgg gaactatggt ttcttcgcct actggggcca gggtaccctc    420
gtgactgtca gcagcgccag caccaagggc cccagcgtgt tcccactggc cccaagctcc    480
aagtcaacct ccggcggaac tgctgcgctg ggctgcttgg tgaaggacta cttccccgaa    540
ccggtcaccg tgtcctggaa cagcggagcc ctgacctcgg gagtccacac tttcccgct    600 gtgctgcagt cgtccggcct gtactcgctc tgtccgtgg tcactgtccc gtcctcgtcc    660
ctgggtactc agacctacat ttgcaacgtc aaccacaagc cttcaaacac gaaagtggac    720
aagaaggtcg agccgaagtc ctgcgacaaa acccatactt gccctccttg tccggctccc    780
gaactgctgg gcggaccttc cgtgttcctc ttcccgccta gccgaaaga caccctgatg    840 atcagcagga ctccggaagt gacatgcgtg gtggtggacg tgtcgcacga ggacccggag    900
gtcaagttta attggtacgt ggacggagtg aagtccaca acgccaagac caagccacgg    960
gaagaacagt acaattccac ctatcgcgtg gtgtccgtgc ttaccgtgct tcaccaagac   1020
tggctgaacg gaaaggagta caagtgcaaa gtgtcaaaca aagccctgcc tgccccaatc   1080
gaaaagacca tcagcaaggc caaggggcag cctcgggaac cccaagtgta cactctcccg   1140
ccgtcaagag atgaactgac caagaaccaa gtgtccctca cttgtctcgt gaagggattc   1200 taccccctccg atatcgccgt ggagtgggaa tccaacgggc aacccgagaa caactacaag   1260
accacccctc cggtgcttga ttccgatggc tccttcttcc tctactccaa gctgaccgtg   1320
gacaagtcaa gatggcagca ggggaacgtg ttctcctgct ccgtcatgca cgaggccctg   1380
cacaaccatt acacccagaa gtctctgtcg ctgagcccgg gaaaataa              1428

<210> SEQ ID NO 25
```

<211> LENGTH: 6833
<212> TYPE: DNA
<213> ORGANISM: Artificial Sequence
<220> FEATURE:
<223> OTHER INFORMATION: Plasmid encoding the Light Chain of a melanin Humanized Antibody (8C3-HE-VK4-hKappa)

<400> SEQUENCE: 25

| | | | | | |
|---|---|---|---|---|---|
| tgccgcaaaa | aagggaataa | gggcgacacg | gaaatgttga | atactcatac | tcttcctttt | 60 |
| tcaatattat | tgaagcattt | atcagggtta | ttgtctcatg | agcggataca | tatttgaatg | 120 |
| tatttagaaa | aataaacaaa | taggggttcc | gcgcacattt | ccccgaaaag | tgccacctgg | 180 |
| gaaattgtaa | acgttaatat | tttgttaaaa | ttcgcgttaa | attttgtta | aatcagctca | 240 |
| ttttttaacc | aataggccga | aatcggcaaa | atcccttata | aatcaaaaga | atagaccgag | 300 |
| atagggttga | gtgttgttcc | agtttggaac | aagagtccac | tattaaagaa | cgtggactcc | 360 |
| aacgtcaaag | ggcgaaaaac | cgtctatcag | ggcgatggcc | cactacgtga | accatcaccc | 420 |
| taatcaagtt | ttttggggtc | gaggtgccgt | aaagcactaa | atcggaaccc | taaagggagc | 480 |
| ccccgattta | gagcttgacg | gggaaagccg | gcgaacgtgg | cgagaaagga | agggaagaaa | 540 |
| gcgaaaggag | cgggcgctag | ggcgctggca | agtgtagcgg | tcacgctgcg | cgtaaccacc | 600 |
| acacccgccg | cgcttaatgc | gccgctacag | ggcgcgtccc | attcgccatt | caggctgcgc | 660 |
| aactgttggg | aagggcgatc | ggtgcgggcc | tcttcgctat | tacgccagct | ggcgaaaggg | 720 |
| ggatgtgctg | caaggcgatt | aagttgggta | acgccagggt | tttcccagtc | acgacgttgt | 780 |
| aaaacgacgg | ccagtgagcg | cgcgtaatac | gactcactat | agggcgaatt | gggtaccggg | 840 |
| ccccccctcg | aggtcgacgg | tatcgataag | cttgatatcg | aattcgctgg | gctgagaccc | 900 |
| gcagaggaag | acgctctagg | gatttgtccc | ggactagcga | gatggcaagg | ctgaggacgg | 960 |
| gaggctgatt | gagaggcgaa | ggtacaccct | aatctcaata | caaccttgg | agctaagcca | 1020 |
| gcaatggtag | agggaagatt | ctgcacgtcc | cttccaggcg | gcctcccgt | caccacccac | 1080 |
| cccaacccgc | cccgaccgga | gctgagagta | attcatacaa | aaggactcgc | ccctgccttg | 1140 |
| gggaatccca | gggaccgtcg | ttaaactccc | actaacgtag | aacccagaga | tcgctgcgtt | 1200 |
| cccgccccct | cacccgcccg | ctctcgtcat | cactgaggtg | gagaagagca | tgcgtgaggc | 1260 |
| tccggtgccc | gtcagtgggc | agagcgcaca | tcgcccacag | tccccgagaa | gttggggga | 1320 |
| ggggtcggca | attgaaccgg | tgcctagaga | aggtggcgcg | gggtaaactg | ggaaagtgat | 1380 |
| gtcgtgtact | ggctccgcct | ttttcccgag | ggtgggggag | aaccgtatat | aagtgcagta | 1440 |
| gtcgccgtga | acgttctttt | tcgcaacggg | tttgccgcca | gaacacaggt | aagtgccgtg | 1500 |
| tgtggttccc | gcgggcctgg | cctctttacg | ggttatggcc | cttgcgtgcc | ttgaattact | 1560 |
| tccacgcccc | tggctgcagt | acgtgattct | tgatcccgag | cttcggggttg | aaagtgggtg | 1620 |
| ggagagttcg | aggccttgcg | cttaaggagc | cccttcgcct | cgtgcttgag | ttgaggcctg | 1680 |
| gcttgggcgc | tggggccgcc | gcgtgcgaat | ctggtggcac | cttcgcgcct | atctcgctgc | 1740 |
| tttcgataag | tctctagcca | tttaaaattt | ttgatgacct | gctgcgacgc | tttttttctg | 1800 |
| gcaagatagt | cttgtaaatg | cgggccaaga | tctgcacact | ggtatttcgg | tttttggggc | 1860 |
| cgcgggcggc | gacggggccc | gtgcgtccca | gcgcacatgt | tcggcgaggc | ggggcctgcg | 1920 |
| agcgcggcca | ccgagaatcg | gacggggta | gtctcaagct | ggccggcctg | ctctggtgcc | 1980 |
| tggcctcgcg | ccgccgtgta | tcgccccgcc | ctgggcggca | aggctggccc | ggtcggcacc | 2040 |
| agttgcgtga | gcggaaagat | ggccgcttcc | cggccctgct | gcagggagct | caaaatggag | 2100 |

```
gacgcggcgc tcgggagagc gggcgggtga gtcacccaca caaaggaaaa gggcctttcc    2160
gtcctcagcc gtcgcttcat gtgactccac ggagtaccgg gcgccgtcca ggcacctcga    2220
ttagttctcg agcttttgga gtacgtcgtc tttaggttgg ggggaggggt tttatgcgat    2280
ggagtttccc cacactgagt gggtggagac tgaagttagg ccagcttggc acttgatgta    2340
attctccttg gaatttgccc ttttttgagtt tggatcttgg ttcattctca gcctcagac    2400 agtggttcaa agttttttcc ttccatttca ggtgtcgtga aaactacccc taaaagccaa    2460
atctagagcc accatggaca tgagagtgcc ggcgcaactg ctcggcctgc tgttgctgtg    2520
gctgagggga gccagatgcg acatcgtgat gactcagtca cccgatagcc ttgcggtgtc    2580
cctcggagaa cgcgccacca tcaactgtaa agcctccgaa tccgtggact cctacggcac    2640
ctccttcatg cactggtacc agcagaagcc aggacagcct cccaagctgt tgatctatct    2700
ggcctcgaat cgggaatcag gagtgccgga ccggttcagc ggctccggat cacgcactga    2760
cttcacgctg accattagcc ccgtgcaagc agaggacgtg gcgacctact actgccagca    2820
gaacaacgaa taccttaca ctttcggcca gggtaccaag ctcgaaatca gccggacagt    2880
ggcagcccca tcggtgttca ttttccccgcc gtcggatgag cagctcaagt ccggtactgc    2940
ctccgtggtc tgcctgctga caactttta ccctcgcgaa gcgaaggtcc aatggaaagt    3000
ggataacgcc ctccagtccg gaaactccca ggagtctgtc accgagcagg actcaaagga    3060
cagcacttac tccctgtcct cgactctgac cctgtcgaag gcagattacg agaagcacaa    3120
agtgtacgcc tgcgaagtga cccatcaagg cctttccagc ccggtcacca agagcttcaa    3180 tcgggggggag tgttagtaat gaggatcccc ctattctata gtgtcaccta aatgctagag    3240
ctcgctgatc agcctcgact gtgccttcta gttgccagcc atctgttgtt tgcccctccc    3300
ccgtgccttc cttgaccctg gaaggtgcca ctcccactgt cctttcctaa taaaatgagg    3360
aaattgcatc gcattgtctg agtaggtgtc attctattct ggggggtggg gtggggcagg    3420
acagcaaggg ggaggattgg gaagacaata gcaggcatgc tggggatgcg gtgggctcta    3480
tggcttctga ggcggaaaga accagctggg gctcgagcgg ccgcccttc tgaggcggaa    3540 agaaccagct gtggaatgtg tgtcagttag ggtgtggaaa gtccccaggc tccccagcag    3600
gcagaagtat gcaaagcatg catctcaatt agtcagcaac caggtgtgga agtccccag    3660 gctccccagc aggcagaagt atgcaaagca tgcatctcaa ttagtcagca accatagtcc    3720
cgcccctaac tccgcccatc ccgcccctaa ctccgcccag ttccgcccat tctccgcccc    3780
atggctgact aatttttttt atttatgcag aggccgaggc cgcctcggcc tctgagctat    3840
tccagaagta gtgaggaggc ttttttggag gcctaggctt ttgcaaaaaa gctagcttcc    3900
cgctgccatc atggttcgac cattgaactg catcgtcgcc gtgtcccaaa atatggggat    3960
tggcaagaac ggagacctac cctggcctcc gctcaggaac gagttcaagt acttccaaag    4020
aatgaccaca acctcttcag tggaaggtaa acagaatctg gtgattatgg gtaggaaaac    4080
ctggttctcc attcctgaga agaatcgacc tttaaaggac agaattaata tagttctcag    4140
tagagaactc aaagaaccac cacgaggagc tcattttctt gccaaaagtt tggatgatgc    4200
cttaagactt attgaacaac cggaattggc aagtaaagta gacatggttt ggatagtcgg    4260
aggcagttct gtttaccagg aagccatgaa tcaaccaggc caccttagac tctttgtgac    4320
aaggatcatg caggaatttg aaagtgacac gttttttccca gaaattgatt tggggaaata    4380
taaacttctc ccagaatacc caggcgtcct ctctgaggtc caggaggaaa aaggcatcaa    4440
gtataagttt gaagtctacg agaagaaaga ctaacaggaa gatgctttca gttctctgc    4500
```

```
tcccctccta aagctatgca tttttataag accatgggac ttttgctggc tttagatccc    4560
gcggagatcc agacatgata agatacattg atgagtttgg acaaaccaca actagaatgc    4620
agtgaaaaaa atgctttatt tgtgaaattt gtgatgctat tgctttattt gtaaccatta    4680
taagctgcaa taaacaagtt aacaacaaca attgcattca ttttatgttt caggttcagg    4740
gggaggtgtg ggaggttttt taaagcaagt aaaacctcta caaatgtggt atggctgatt    4800
atgagctcca gcttttgttc cctttagtga gggttaattg cgcgcttggc gtaatcatgg    4860
tcatagctgt ttcctgtgtg aaattgttat ccgctcacaa ttccacacaa catacgagcc    4920
ggaagcataa agtgtaaagc ctggggtgcc taatgagtga gctaactcac attaattgcg    4980
ttgcgctcac tgcccgcttt ccagtcggga acctgtcgt gccagctgca ttaatgaatc    5040
ggccaacgcg cggggagagg cggtttgcgt attgggcgct cttccgcttc ctcgctcact    5100
gactcgctgc gctcggtcgt tcggctgcgg cgagcggtat cagctcactc aaaggcggta    5160
atacggttat ccacagaatc aggggataac gcaggaaaga acatgtgagc aaaaggccag    5220
caaaaggcca ggaaccgtaa aaaggccgcg ttgctggcgt ttttccatag gctccgcccc    5280
cctgacgagc atcacaaaaa tcgacgctca agtcagaggt ggcgaaaccc gacaggacta    5340
taaagatacc aggcgtttcc ccctggaagc tccctcgtgc gctctcctgt tccgaccctg    5400
ccgcttaccg gatacctgtc cgcctttctc ccttcgggaa gcgtggcgct ttctcatagc    5460
tcacgctgta ggtatctcag ttcggtgtag tcgttcgct ccaagctggg ctgtgtgcac    5520
gaaccccccg ttcagcccga ccgctgcgcc ttatccggta actatcgtct tgagtccaac    5580
ccggtaagac acgacttatc gccactggca gcagccactg gtaacaggat tagcagagcg    5640
aggtatgtag gcggtgctac agagttcttg aagtggtggc ctaactacgg ctacactaga    5700
aggacagtat ttggtatctg cgctctgctg aagccagtta ccttcggaaa aagagttggt    5760
agctcttgat ccggcaaaca aaccaccgct ggtagcggtg gttttttgt ttgcaagcag    5820 cagattacgc gcagaaaaaa aggatctcaa gaagatcctt tgatcttttc tacggggtct    5880
gacgctcagt ggaacgaaaa ctcacgttaa gggattttgg tcatgagatt atcaaaaagg    5940
atcttcacct agatcctttt aaattaaaaa tgaagtttta atcaatcta aagtatatat    6000 gagtaaactt ggtctgacag ttaccaatgc ttaatcagtg aggcacctat ctcagcgatc    6060
tgtctatttc gttcatccat agttgcctga ctccccgtcg tgtagataac tacgatacgg    6120
gagggcttac catctggccc cagtgctgca atgataccgc gagacccacg ctcaccggct    6180
ccagatttat cagcaataaa ccagccagcc ggaagggccg agcgcagaag tggtcctgca    6240
actttatccg cctccatcca gtctattaat tgttgccggg aagctagagt aagtagttcg    6300
ccagttaata gtttgcgcaa cgttgttgcc attgctacag gcatcgtggt gtcacgctcg    6360
tcgtttggta tggcttcatt cagctccggt tcccaacgat caaggcgagt tacatgatcc    6420
cccatgttgt gcaaaaaagc ggttagctcc ttcggtcctc cgatcgttgt cagaagtaag    6480
ttggccgcag tgttatcact catggttatg gcagcactgc ataattctct tactgtcatg    6540
ccatccgtaa gatgcttttc tgtgactggt gagtactcaa ccaagtcatt ctgagaatag    6600
tgtatgcggc gaccgagttg ctcttgcccg gcgtcaatac gggataatac cgcgccacat    6660
agcagaactt taaaagtgct catcattgga aaacgttctt cggggcgaaa actctcaagg    6720
atcttaccgc tgttgagatc cagttcgatg taacccactc gtgcacccaa ctgatcttca    6780
gcatctttta ctttcaccag cgtttctggg tgagcaaaaa caggaaggca aaa           6833
```

<210> SEQ ID NO 26
<211> LENGTH: 6833
<212> TYPE: DNA
<213> ORGANISM: Artificial Sequence
<220> FEATURE:
<223> OTHER INFORMATION: Plasmid encoding the Light Chain of a melanin Humanized Antibody (8C3-HE-VK1A-hKappa)

<400> SEQUENCE: 26

| | | | | | |
|---|---|---|---|---|---|
| cggtgcgggc | ctcttcgcta | ttacgccagc | tggcgaaagg | gggatgtgct | gcaaggcgat | 60 |
| taagttgggt | aacgccaggg | ttttcccagt | cacgacgttg | taaaacgacg | gccagtgagc | 120 |
| gcgcgtaata | cgactcacta | tagggcgaat | tgggtaccgg | ccccccctc | gaggtcgacg | 180 |
| gtatcgataa | gcttgatatc | gaattcgctg | gctgagacc | cgcagaggaa | gacgctctag | 240 |
| ggatttgtcc | cggactagcg | agatggcaag | gctgaggacg | gaggctgat | tgagaggcga | 300 |
| aggtacaccc | taatctcaat | acaacccttg | gagctaagcc | agcaatggta | gagggaagat | 360 |
| tctgcacgtc | cctccaggc | ggcctcccg | tcaccaccca | ccccaacccg | ccccgaccgg | 420 |
| agctgagagt | aattcataca | aaaggactcg | cccctgcctt | ggggaatccc | agggaccgtc | 480 |
| gttaaactcc | cactaacgta | gaacccagag | atcgctgcgt | tcccgccccc | tcacccgccc | 540 |
| gctctcgtca | tcactgaggt | ggagaagagc | atgcgtgagg | ctccggtgcc | cgtcagtggg | 600 |
| cagagcgcac | atcgcccaca | gtccccgaga | agttgggggg | aggggtcggc | aattgaaccg | 660 |
| gtgcctagag | aaggtggcgc | ggggtaaact | gggaaagtga | tgtcgtgtac | tggctccgcc | 720 |
| ttttcccga | gggtggggga | gaaccgtata | taagtgcagt | agtcgccgtg | aacgttcttt | 780 |
| tcgcaacgg | gtttgccgcc | agaacacagg | taagtgccgt | gtgtggttcc | cgcgggcctg | 840 |
| gcctctttac | gggttatggc | ccttgcgtgc | cttgaattac | ttccacgccc | ctggctgcag | 900 |
| tacgtgattc | ttgatcccga | gcttcgggtt | gaaagtgggg | gggagagttc | gaggccttgc | 960 |
| gcttaaggag | cccccttcgcc | tcgtgcttga | gttgaggcct | ggcttgggcg | ctggggccgc | 1020 |
| cgcgtgcgaa | tctggtggca | ccttcgcgcc | tatctcgctg | ctttcgataa | gtctctagcc | 1080 |
| atttaaaatt | tttgatgacc | tgctgcgacg | cttttttct | ggcaagatag | tcttgtaaat | 1140 |
| gcgggccaag | atctgcacac | tggtatttcg | gttttgggg | ccgcgggcgg | cgacggggcc | 1200 |
| cgtgcgtccc | agcgcacatg | ttcggcgagg | cggggcctgc | gagcgcggcc | accgagaatc | 1260 |
| ggacggggt | agtctcaagc | tggccggcct | gctctggtgc | ctggcctcgc | gccgccgtgt | 1320 |
| atcgccccgc | cctgggcggc | aaggctggcc | cggtcggcac | cagttgcgtg | agcggaaaga | 1380 |
| tggccgcttc | ccggccctgc | tgcagggagc | tcaaaatgga | ggacgcggcg | ctcgggagag | 1440 |
| cgggcgggtg | agtcacccac | acaaaggaaa | agggccttc | cgtcctcagc | cgtcgcttca | 1500 |
| tgtgactcca | cggagtaccg | ggcgccgtcc | aggcacctcg | attagttctc | gagcttttgg | 1560 |
| agtacgtcgt | ctttaggttg | gggggagggg | ttttatgcga | tggagtttcc | ccacactgag | 1620 |
| tgggtggaga | ctgaagttag | gccagcttgg | cacttgatgt | aattctcctt | ggaatttgcc | 1680 |
| cttttttgagt | ttggatcttg | gttcattctc | aagcctcaga | cagtggttca | agtttttttc | 1740 |
| cttccatttc | aggtgtcgtg | aaaactaccc | ctaaaagcca | aatctagagc | caccatggac | 1800 |
| atgagagtgc | cggcgcaact | gctcggcctg | ctgttgctgt | ggctgagggg | agccagatgc | 1860 |
| gacatccaga | tgactcagtc | accctcgagc | cttagcgtgt | ccctcggaga | tcgcgccacc | 1920 |
| atcacctgtc | gggcctccga | atccgtggac | tcctacggca | cctccttcat | gcactggtac | 1980 |
| cagcagaagc | caggaaaagcc | tcccaagctg | ttgatctatc | tggcctcgaa | tctggaatca | 2040 |

```
ggagtgccgt cgcggttcag cggctccgga tcacgcactg acttcacgct gaccattagc    2100
cccgtgcaag cagaggactt tgcgacctac tactgccagc agaacaacga atacccttac    2160
actttcggcc agggtaccaa gctcgaaatc aagcggacag tggcagcccc atcggtgttc    2220
attttcccgc cgtcggatga gcagctcaag tccggtactg cctccgtggt ctgcctgctg    2280
aacaactttt accctcgcga agcgaaggtc caatggaaag tggataacgc cctccagtcc    2340
ggaaactccc aggagtctgt caccgagcag gactcaaagg acagcactta ctccctgtcc    2400
tcgactctga ccctgtcgaa ggcagattac gagaagcaca agtgtacgc ctgcgaagtg    2460 acccatcaag gccttttccag cccggtcacc aagagcttca tcgggggga gtgttagtaa    2520 tgaggatccc cctattctat agtgtcacct aaatgctaga gctcgctgat cagcctcgac    2580
tgtgccttct agttgccagc catctgttgt ttgcccctcc ccgtgccttt ccttgaccct    2640
ggaaggtgcc actcccactg tcctttccta ataaaatgag gaaattgcat cgcattgtct    2700
gagtaggtgt cattctattc tggggggtgg ggtggggcag gacagcaagg ggaggattg    2760 ggaagacaat agcaggcatg ctggggatgc ggtgggctct atggcttctg aggcggaaag    2820
aaccagctgg ggctcgagcg gccgcccctt ctgaggcgga agaaccagc tgtggaatgt    2880 gtgtcagtta gggtgtggaa agtccccagg ctccccagca ggcagaagta tgcaaagcat    2940
gcatctcaat tagtcagcaa ccaggtgtgg aaagtcccca ggctcccag caggcagaag    3000 tatgcaaagc atgcatctca attagtcagc aaccatagtc ccgcccctaa ctccgcccat    3060
cccgccccta actccgccca gttccgccca ttctccgccc catggctgac taatttttt    3120 tatttatgca gaggccgagg ccgcctcggc ctctgagcta ttccagaagt agtgaggagg    3180
cttttttgga ggcctaggct tttgcaaaaa gctagcttc ccgctgccat catggttcga    3240
ccattgaact gcatcgtcgc cgtgtcccaa aatatgggga ttggcaagaa cggagaccta    3300
ccctggcctc cgctcaggaa cgagttcaag tacttccaaa gaatgaccac aacctcttca    3360
gtggaaggta aacagaatct ggtgattatg ggtaggaaaa cctggttctc cattcctgag    3420
aagaatcgac ctttaaagga cagaattaat atagttctca gtagagaact caaagaacca    3480
ccacgaggag ctcatttttct tgccaaaagt ttggatgatg ccttaagact tattgaacaa    3540
ccggaattgg caagtaaagt agacatggtt tggatagtcg gaggcagttc tgtttaccag    3600
gaagccatga tcaaccagg ccaccttaga ctctttgtga caaggatcat gcaggaattt    3660
gaaagtgaca cgttttttccc agaaattgat ttggggaaat ataaacttct cccagaatac    3720
ccaggcgtcc tctctgaggt ccaggaggaa aaaggcatca agtataagtt tgaagtctac    3780
gagaagaaag actaacagga agatgctttc aagttctctg ctcccctcct aaagctatgc    3840
atttttataa gaccatggga cttttgctgg ctttagatcc gcggagatc cagacatgat    3900 aagatacatt gatgagtttg gacaaaccac aactagaatg cagtgaaaaa aatgctttat    3960
ttgtgaaatt tgtgatgcta ttgctttatt tgtaaccatt ataagctgca ataaacaagt    4020
taacaacaac aattgcattc attttatgtt tcaggttcag ggggaggtgt gggaggttttt    4080 ttaaagcaag taaaacctct acaaatgtgg tatggctgat tatgagctcc agcttttgtt    4140 cccttttagtg agggttaatt gcgcgcttgg cgtaatcatg gtcatagctg tttcctgtgt    4200
gaaattgtta tccgctcaca attccacaca acatacgagc cggaagcata agtgtaaag    4260 cctggggtgc ctaatgagtg agctaactca cattaattgc gttgcgctca ctgcccgctt    4320
tccagtcggg aaacctgtcg tgccagctgc attaatgaat cggccaacgc gcggggagag    4380
gcggtttgcg tattgggcgc tcttccgctt cctcgctcac tgactcgctg cgctcggtcg    4440
```

```
ttcggctgcg gcgagcggta tcagctcact caaaggcggt aatacggtta tccacagaat    4500
cagggaataa cgcaggaaag aacatgtgag caaaaggcca gcaaaaggcc aggaaccgta    4560
aaaaggccgc gttgctggcg ttttccata ggctccgccc ccctgacgag catcacaaaa     4620
atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcatag ctcacgctgt aggtatctca    4800
gttcggtgta ggtcgttcgc tccaagctgg gctgtgtgca cgaaccccc gttcagcccg     4860 accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggtttttttg tttgcaagca gcagattacg cgcagaaaaa    5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct tcggggcgaa aactctcaag gatcttaccg ctgttgagat    6060
ccagttcgat gtaacccact cgtgcaccca actgatcttc agcatctttt actttcacca    6120
gcgtttctgg gtgagcaaaa acaggaaggc aaaatgccgc aaaaaaggga ataagggcga    6180
cacggaaatg ttgaatactc atactcttcc ttttcaata ttattgaagc atttatcagg     6240
gttattgtct catgagcgga tacatatttg aatgtattta gaaaaataaa caaatagggg    6300
ttccgcgcac atttccccga aaagtgccac ctgggaaatt gtaaacgtta atattttgtt    6360
aaaattcgcg ttaaattttt gttaaatcag ctcatttttt aaccaatagg ccgaaatcgg    6420
caaaatccct tataaatcaa agaatagac cgagataggg ttgagtgttg ttccagtttg     6480
gaacaagagt ccactattaa agaacgtgga ctccaacgtc aaagggcgaa aaaccgtcta    6540
tcagggcgat ggcccactac gtgaaccatc accctaatca agttttttgg ggtcgaggtg    6600
ccgtaaagca ctaaatcgga acctaaagg gagcccccga tttagagctt gacggggaaa     6660
gccggcgaac gtggcgagaa aggaagggaa gaaagcgaaa ggagcgggcg ctagggcgct    6720
ggcaagtgta gcggtcacgc tgcgcgtaac caccacaccc gccgcgctta atgcgccgct    6780
```

-continued

| | |
|---|---|
| acagggcgcg tcccattcgc cattcaggct gcgcaactgt tgggaagggc gat | 6833 |

<210> SEQ ID NO 27
<211> LENGTH: 6833
<212> TYPE: DNA
<213> ORGANISM: Artificial Sequence
<220> FEATURE:
<223> OTHER INFORMATION: Plasmid encoding the Light Chain of a melanin Humanized Antibody (8C3-HE-VK1B-hKappa)

<400> SEQUENCE: 27

| | |
|---|---|
| cggtgcgggc tcttcgcta ttacgccagc tggcgaaagg gggatgtgct gcaaggcgat | 60 |
| taagttgggt aacgccaggg ttttcccagt cacgacgttg taaaacgacg gccagtgagc | 120 |
| gcgcgtaata cgactcacta tagggcgaat tgggtaccgg ccccccctc gaggtcgacg | 180 |
| gtatcgataa gcttgatatc gaattcgctg ggctgagacc cgcagaggaa gacgctctag | 240 |
| ggatttgtcc cggactagcg agatggcaag gctgaggacg ggaggctgat tgagaggcga | 300 |
| aggtacaccc taatctcaat acaaccttg gagctaagcc agcaatggta gagggaagat | 360 |
| tctgcacgtc ccttccaggc ggcctccccg tcaccaccca ccccaacccg ccccgaccgg | 420 |
| agctgagagt aattcataca aaaggactcg cccctgcctt ggggaatccc agggaccgtc | 480 |
| gttaaactcc cactaacgta gaacccagag atcgctgcgt tcccgccccc tcacccgccc | 540 |
| gctctcgtca tcactgaggt ggagaagagc atgcgtgagg ctccggtgcc cgtcagtggg | 600 |
| cagagcgcac atcgcccaca gtccccgaga agttgggggg aggggtcggc aattgaaccg | 660 |
| gtgcctagag aaggtggcgc ggggtaaact gggaaagtga tgtcgtgtac tggctccgcc | 720 |
| tttttcccga gggtggggga gaaccgtata taagtgcagt agtcgccgtg aacgttcttt | 780 |
| ttcgcaacgg gtttgccgcc agaacacagg taagtgccgt gtgtggttcc cgcgggcctg | 840 |
| gcctctttac gggttatggc ccttgcgtgc cttgaattac ttccacgccc ctggctgcag | 900 |
| tacgtgattc ttgatcccga gcttcgggtt gaaagtgggt gggagagttc gaggccttgc | 960 |
| gcttaaggag cccccttcgcc tcgtgcttga gttgaggcct ggcttgggcg ctggggccgc | 1020 |
| cgcgtgcgaa tctggtggca ccttcgcgcc tatctcgctg ctttcgataa gtctctagcc | 1080 |
| atttaaaatt tttgatgacc tgctgcgacg ctttttttct ggcaagatag tcttgtaaat | 1140 |
| gcgggccaag atctgcacac tggtatttcg gtttttgggg ccgcgggcgg cgacggggcc | 1200 |
| cgtgcgtccc agcgcacatg ttcggcgagg cggggcctgc gagcgcggcc accgagaatc | 1260 |
| ggacggggt agtctcaagc tggccggcct gctctggtgc ctggcctcgc gccgccgtgt | 1320 |
| atcgccccgc cctgggcggc aaggctggcc cggtcggcac cagttgcgtg agcggaaaga | 1380 |
| tggccgcttc ccggccctgc tgcagggagc tcaaaatgga ggacgcggcg ctcgggagag | 1440 |
| cgggcgggtg agtcacccac acaaaggaaa agggcctttc cgtcctcagc cgtcgcttca | 1500 |
| tgtgactcca cggagtaccg ggcgccgtcc aggcacctcg attagttctc gagcttttgg | 1560 |
| agtacgtcgt ctttaggttg ggggagggg ttttatgcga tggagtttcc ccacactgag | 1620 |
| tgggtggaga ctgaagttag gccagcttgg cacttgatgt aattctcctt ggaatttgcc | 1680 |
| ctttttgagt ttggatcttg gttcattctc aagcctcaga cagtggttca aagttttttc | 1740 |
| cttccatttc agtgtcgtg aaaactaccc ctaaaagcca atctagagc caccatggac | 1800 |
| atgagagtgc cggcgcaact gctcggcctg ctgttgctgt ggctgagggg agccagatgc | 1860 |
| gacatccaga tgactcagtc accctcgagc ttagcgtgt ccgtgggaga tcgcgccacc | 1920 |
| atcacctgtc gggcctccga atccgtggac tcctacggca cctccttcat gcactggtac | 1980 |

```
cagcagaagc caggaaagcc tcccaagctg ttgatctatc tggcctcgaa tctgcagtca    2040
ggagtgccgt cgcggttcag cggctccgga tcacgcactg acttcacgct gaccattagc    2100
cccgtgcaag cagaggactt tgcgacctac tactgccagc agaacaacga atacccttac    2160
actttcggcc agggtaccaa gctcgaaatc aagcggacag tggcagcccc atcggtgttc    2220
attttcccgc cgtcggatga gcagctcaag tccggtactg cctccgtggt ctgcctgctg    2280
aacaactttt accctcgcga agcgaaggtc aatggaaag tggataacgc cctccagtcc    2340
ggaaactccc aggagtctgt caccgagcag gactcaaagg acagcactta ctccctgtcc    2400
tcgactctga ccctgtcgaa ggcagattac gagaagcaca aagtgtacgc ctgcgaagtg    2460
acccatcaag gccttccag cccggtcacc aagagcttca atcggggga gtgttagtaa    2520 tgaggatccc cctattctat agtgtcacct aaatgctaga gctcgctgat cagcctcgac    2580
tgtgccttct agttgccagc catctgttgt ttgcccctcc cccgtgcctt ccttgaccct    2640
ggaaggtgcc actcccactg tccttttccta ataaaatgag gaaattgcat cgcattgtct    2700
gagtaggtgt cattctattc tggggggtgg ggtggggcag gacagcaagg gggaggattg    2760
ggaagacaat agcaggcatg ctggggatgc ggtgggctct atggcttctg aggcggaaag    2820
aaccagctgg ggctcgagcg gccgcccctt ctgaggcgga agaaccagc tgtggaatgt    2880 gtgtcagtta gggtgtggaa agtccccagg ctccccagca ggcagaagta tgcaaagcat    2940
gcatctcaat tagtcagcaa ccaggtgtgg aaagtcccca ggctcccag caggcagaag    3000 tatgcaaagc atgcatctca attagtcagc aaccatagtc ccgcccctaa ctccgcccat    3060
cccgccccta actccgccca gttccgccca ttctccgccc catggctgac taattttttt    3120
tatttatgca gaggccgagg ccgcctcggc ctctgagcta ttccagaagt agtgaggagg    3180
cttttttgga ggcctaggct tttgcaaaaa gctagcttc ccgctgccat catggttcga    3240
ccattgaact gcatcgtcgc cgtgtcccaa aatatgggga ttggcaagaa cggagaccta    3300
ccctggcctc cgctcaggaa cgagttcaag tacttccaaa gaatgaccac aacctcttca    3360
gtggaaggta aacagaatct ggtgattatg ggtaggaaaa cctggttctc cattcctgag    3420
aagaatcgac ctttaaagga cagaattaat atagttctca gtagagaact caaagaacca    3480
ccacgaggag ctcattttct tgccaaaagt ttggatgatg ccttaagact tattgaacaa    3540
ccggaattgg caagtaaagt agacatggtt tggatagtcg gaggcagttc tgtttaccag    3600
gaagccatga atcaaccagg ccaccttaga ctctttgtga caaggatcat gcaggaattt    3660
gaaagtgaca cgttttttccc agaaattgat ttggggaaat ataaacttct cccagaatac    3720
ccaggcgtcc tctctgaggt ccaggaggaa aaaggcatca agtataagtt tgaagtctac    3780
gagaagaaag actaacagga agatgctttc aagttctctg ctcccctcct aaagctatgc    3840
atttttataa gaccatggga cttttgctgg ctttagatcc cgcggagatc cagacatgat    3900
aagatacatt gatgagtttg gacaaaccac aactagaatg cagtgaaaaa aatgctttat    3960
ttgtgaaatt tgtgatgcta ttgctttatt tgtaaccatt ataagctgca ataaacaagt    4020
taacaacaac aattgcattc attttatgtt tcaggttcag ggggaggtgt gggaggtttt    4080
ttaaagcaag taaaacctct acaaatgtgg tatggctgat tatgagctcc agcttttgtt    4140
ccctttagtg agggttaatt gcgcgcttgg cgtaatcatg gtcatagctg tttcctgtgt    4200
gaaattgtta tccgctcaca attccacaca acatacgagc cggaagcata aagtgtaaag    4260
cctggggtgc ctaatgagtg agctaactca cattaattgc gttgcgctca ctgcccgctt    4320
tccagtcggg aaacctgtcg tgccagctgc attaatgaat cggccaacgc gcggggagag    4380
```

```
gcggtttgcg tattgggcgc tcttccgctt cctcgctcac tgactcgctg cgctcggtcg    4440
ttcggctgcg gcgagcggta tcagctcact caaaggcggt aatacggtta ccacagaat     4500 caggggataa cgcaggaaag aacatgtgag caaaaggcca gcaaaaggcc aggaaccgta    4560
aaaaggccgc gttgctggcg ttttccata ggctccgccc ccctgacgag catcacaaaa     4620
atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcatag ctcacgctgt aggtatctca    4800
gttcggtgta ggtcgttcgc tccaagctgg gctgtgtgca cgaaccccc gttcagcccg     4860 accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggttttttg tttgcaagca gcagattacg cgcagaaaaa     5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct cggggcgaa aactctcaag gatcttaccg ctgttgagat     6060
ccagttcgat gtaacccact cgtgcaccca actgatcttc agcatctttt actttcacca    6120
gcgtttctgg gtgagcaaaa acaggaaggc aaaatgccgc aaaaaaggga ataagggcga    6180
cacggaaatg ttgaatactc atactcttcc tttttcaata ttattgaagc atttatcagg    6240
gttattgtct catgagcgga tacatatttg aatgtattta gaaaaataaa caaataggg     6300 ttccgcgcac atttccccga aaagtgccac ctggaaatt gtaaacgtta atattttgtt     6360
aaaattcgcg ttaaattttt gttaaatcag ctcattttt aaccaatagg ccgaaatcgg     6420
caaaatccct tataaatcaa agaatagac cgagataggg ttgagtgttg ttccagtttg     6480
gaacaagagt ccactattaa agaacgtgga ctccaacgtc aaagggcgaa aaaccgtcta    6540
tcagggcgat ggcccactac gtgaaccatc accctaatca gtttttggg ggtcgaggtg     6600 ccgtaaagca ctaaatcgga acctaaagg gagcccccga tttagagctt gacggggaaa     6660
gccggcgaac gtggcgagaa aggaagggaa gaaagcgaaa ggagcgggcg ctagggcgct    6720
```

```
ggcaagtgta gcggtcacgc tgcgcgtaac caccacaccc gccgcgctta atgcgccgct    6780
acagggcgcg tcccattcgc cattcaggct gcgcaactgt gggaagggc gat            6833
```

<210> SEQ ID NO 28
<211> LENGTH: 7679
<212> TYPE: DNA
<213> ORGANISM: Artificial Sequence
<220> FEATURE:
<223> OTHER INFORMATION: Plasmid encoding the Heavy Chain of a melanin
      Humanized Antibody (8C3-HE-VH3A-hIgG1)

<400> SEQUENCE: 28

```
cggtgcgggc tcttcgcta ttacgccagc tggcgaaagg gggatgtgct gcaaggcgat     60
taagttgggt aacgccaggg ttttcccagt cacgacgttg taaaacgacg gccagtgagc   120
gcgcgtaata cgactcacta tagggcgaat tgggtaccgg gccccccctc gaggtcgacg   180
gtatcgataa gcttgatatc gaattcgctg gctgagacc cgcagaggaa gacgctctag    240
ggatttgtcc cggactagcg agatggcaag gctgaggacg ggaggctgat tgagaggcga   300
aggtacaccc taatctcaat acaacccttg gagctaagcc agcaatggta gagggaagat   360
tctgcacgtc ccttccaggc ggcctcccccg tcaccaccca ccccaaccccg ccccgaccgg  420 agctgagagt aattcataca aaaggactcg cccctgcctt ggggaatccc agggaccgtc   480
gttaaactcc cactaacgta gaacccagag atcgctgcgt tcccgccccc tcacccgccc   540
gctctcgtca tcactgaggt ggagaagagc atgcgtgagg ctccggtgcc cgtcagtggg   600
cagagcgcac atcgcccaca gtccccgaga agttggggg aggggtcggc aattgaaccg   660
gtgcctagag aaggtggcgc ggggtaaact gggaaagtga tgtcgtgtac tggctccgcc   720 ttttcccga gggtggggga gaaccgtata taagtgcagt agtcgccgtg aacgttcttt     780
ttcgcaacgg gtttgccgcc agaacacagg taagtgccgt gtgtggttcc gcgggcctg    840 gcctctttac gggttatggc ccttgcgtgc cttgaattac ttccacgccc ctggctgcag   900
tacgtgattc ttgatcccga gcttcgggtt gaaagtgggg gggagagttc gaggccttgc   960
gcttaaggag ccccttcgcc tcgtgcttga gttgaggcct ggcttgggcg ctggggccgc  1020
cgcgtgcgaa tctggtggca ccttcgcgcc tatctcgctg ctttcgataa gtctctagcc  1080
atttaaaatt tttgatgacc tgctgcgacg cttttttttct ggcaagatag tcttgtaaat  1140
gcgggccaag atctgcacac tggtatttcg gttttttgggg ccgcgggcgg cgacggggcc  1200
cgtgcgtccc agcgcacatg ttcggcgagg cggggcctgc gagcgcggcc accgagaatc  1260 ggacggggt agtctcaagc tggccggcct gtctctggtgc ctggcctcgc gccgcgtgt   1320 atcgccccgc cctgggcggc aaggctggcc cggtcggcac cagttgcgtg agcggaaaga  1380
tggccgcttc ccggccctgc tgcagggagc tcaaaatgga ggacgcggcg ctcgggagag  1440
cgggcgggtg agtcacccac acaaaggaaa agggcctttc cgtcctcagc cgtcgcttca  1500
tgtgactcca cggagtaccg ggcgccgtcc aggcacctcg attagttctc gagcttttgg  1560
agtacgtcgt ctttaggttg ggggaggg tttatgcga tggagtttcc ccacactgag     1620
tgggtggaga ctgaagttag gccagcttgg cacttgatgt aattctcctt ggaatttgcc   1680 cttttgagt ttggatcttg gttcattctc aagcctcaga cagtggttca agttttttc    1740 cttccatttc aggtgtcgtg aaaactaccc ctaaaagcca aatctagagc caccatggac  1800
atgcgcgtgc cggcacaact gctgggcctg ctgctgcttt ggctgcgggg agctagatgc  1860
gaagtgcagc tcgtcgaatc cggaggagga ctggtgcagc ctggcggaag catgcgcgtg  1920
```

```
tcatgcgcgg cttccggatt caccttctcg gacgcctgga tggattgggt cagacaagcg    1980
cccggcaaag gcctggaatg ggtggccgag attcggtcca aggcccataa ccacgccacc    2040
tactacgccg agtccgtgaa ggggcgcttt actatctccc gggatgactc gaagtcgacg    2100
gtgtacctcc agatgaactc attgagggcc gaggacactg ggacctacta ctgtacccgc    2160
ggaggctact acgggaacta tggtttcttc gcctactggg gccagggtac cctcgtgact    2220
gtcagcagcg ccagcaccaa gggcccagc gtgttccac tggccccaag ctccaagtca      2280
acctccggcg gaactgctgc gctgggctgc ttggtgaagg actacttccc cgaaccggtc    2340
accgtgtcct ggaacagcgg agccctgacc tcgggagtcc acacttccc cgctgtgctg     2400
cagtcgtccg gcctgtactc gctctcgtcc gtggtcactg tcccgtcctc gtccctgggt    2460
actcagacct acatttgcaa cgtcaaccac aagccttcaa acacgaaagt ggacaagaag    2520
gtcgagccga agtcctgcga caaaacccat acttgccctc cttgtccggc tcccgaactg    2580
ctgggcggac cttccgtgtt cctcttcccg cctaagccga agacaccct gatgatcagc     2640
aggactccgg aagtgacatg cgtggtggtg gacgtgtcgc acgaggaccc ggaggtcaag    2700
tttaattggt acgtggacgg agtggaagtc cacaacgcca agaccaagcc acgggaagaa    2760
cagtacaatt ccacctatcg cgtggtgtcc gtgcttaccg tgcttcacca agactggctg    2820
aacggaaagg agtacaagtg caaagtgtca aacaaagccc tgcctgcccc aatcgaaaag    2880
accatcagca aggccaaggg gcagcctcgg gaaccccaag tgtacactct cccgccgtca    2940
agagatgaac tgaccaagaa ccaagtgtcc ctcacttgtc tcgtgaaggg attctacccc    3000
tccgatatcg ccgtggagtg ggaatccaac gggcaacccg agaacaacta caagaccacc    3060
cctccggtgc ttgattccga tggctccttc ttcctctact ccaagctgac cgtggacaag    3120
tcaagatggc agcaggggaa cgtgttctcc tgctccgtca gcacgaggc cctgcacaac     3180
cattcacccc agaagtctct gtcgctgagc ccgggaaaat aatgaggatc ccctattct     3240
atagtgtcac ctaaatgcta gagctcgctg atcagcctcg actgtgcctt ctagttgcca    3300
gccatctgtt gtttgccct cccccgtgcc ttccttgacc ctggaaggtg ccactcccac      3360
tgtcctttcc taataaaatg aggaaattgc atcgcattgt ctgagtaggt gtcattctat    3420
tctgggggt ggggtggggc aggacagcaa ggggaggat tgggaagaca atagcaggca      3480
tgctggggat gcggtgggct ctatggcttc tgaggcggaa agaaccagct ggggctcgag    3540
cggccgcaga ttgtaccttc tgaggcggaa agaaccagct gtggaatgtg tgtcagttag    3600
ggtgtggaaa gtccccaggc tccccagcag gcagaagtat gcaaagcatg catctcaatt    3660
agtcagcaac caggtgtgga aagtccccag gctccccagc aggcagaagt atgcaaagca    3720
tgcatctcaa ttagtcagca accatagtcc cgccctaac tccgcccatc cgcccctaa      3780
ctccgcccag ttccgcccat tctccgcccc atggctgact aatttttttt atttatgcag    3840
aggccgaggc cgcctcggcc tctgagctat tccagaagta gtgaggaggc ttttttggag    3900
gcctaggctt ttgcaaaaag cttaccatga ttgaacaaga tggattgcac gcaggttctc    3960
cggccgcttg ggtggagagg ctattcggct atgactgggc acaacagaca atcggctgct    4020
ctgatgccgc cgtgttccgg ctgtcagcgc aggggcgccc ggttcttttt gtcaagaccg    4080
acctgtccgg tgccctgaat gaactgcagg acgaggcagc gcggctatcg tggctggcca    4140
cgacgggcgt tccttgcgca gctgtgctcg acgttgtcac tgaagcggga agggactggc    4200
tgctattggg cgaagtgccg gggcaggatc tcctgtcatc tcaccttgct cctgccgaga    4260
aagtatccat catggctgat gcaatgcggc ggctgcatac gcttgatccg gctacctgcc    4320
```

```
cattcgacca ccaagcgaaa catcgcatcg agcgagcacg tactcggatg gaagccggtc    4380
ttgtcgatca ggatgatctg gacgaagagc atcaggggct cgcgccagcc gaactgttcg    4440
ccaggctcaa ggcgcgcatg cccgacggcg aggatctcgt cgtgacccat ggcgatgcct    4500
gcttgccgaa tatcatggtg gaaaatggcc gcttttctgg attcatcgac tgtggccggc    4560
tgggtgtggc ggaccgctat caggacatag cgttggctac ccgtgatatt gctgaagagc    4620
ttggcggcga atgggctgac cgcttcctcg tgctttacgg tatcgccgct cccgattcgc    4680
agcgcatcgc cttctatcgc cttcttgacg agttcttctg agggatcgcg gagatccaga    4740
catgataaga tacattgatg agtttggaca aaccacaact agaatgcagt gaaaaaaatg    4800
ctttatttgt gaaatttgtg atgctattgc tttatttgta accattataa gctgcaataa    4860
acaagttaac aacaacaatt gcattcattt tatgtttcag gttcaggggg aggtgtggga    4920
ggttttttaa agcaagtaaa acctctacaa atgtggtatg gctgattatg agctccagct    4980
tttgttccct ttagtgaggg ttaattgcgc gcttggcgta atcatggtca tagctgtttc    5040
ctgtgtgaaa ttgttatccg ctcacaattc cacacaacat acgagccgga agcataaagt    5100
gtaaagcctg gggtgcctaa tgagtgagct aactcacatt aattgcgttg cgctcactgc    5160
ccgctttcca gtcgggaaac ctgtcgtgcc agctgcatta atgaatcggc caacgcgcgg    5220
ggagaggcgg tttgcgtatt gggcgctctt ccgcttcctc gctcactgac tcgctgcgct    5280
cggtcgttcg gctgcggcga gcggtatcag ctcactcaaa ggcggtaata cggttatcca    5340
cagaatcagg ggataacgca ggaaagaaca tgtgagcaaa aggccagcaa aaggccagga    5400
accgtaaaaa ggccgcgttg ctggcgtttt tccataggct ccgcccccct gacgagcatc    5460
acaaaaatcg acgctcaagt cagaggtggc gaaacccgac aggactataa agataccagg    5520
cgtttccccc tggaagctcc ctcgtgcgct ctcctgttcc gaccctgccg cttaccggat    5580
acctgtccgc ctttctccct tcgggaagcg tggcgctttc tcatagctca cgctgtaggt    5640
atctcagttc ggtgtaggtc gttcgctcca agctgggctg tgtgcacgaa ccccccgttc    5700
agcccgaccg ctgcgcctta tccggtaact atcgtcttga gtccaacccg gtaagacacg    5760
acttatcgcc actggcagca gccactggta acaggattag cagagcgagg tatgtaggcg    5820
gtgctacaga gttcttgaag tggtggccta actacggcta cactagaagg acagtatttg    5880
gtatctgcgc tctgctgaag ccagttacct tcggaaaaag agttggtagc tcttgatccg    5940
gcaaacaaac caccgctggt agcggtggtt tttttgtttg caagcagcag attacgcgca    6000
gaaaaaaagg atctcaagaa gatcctttga tcttttctac ggggtctgac gctcagtgga    6060
acgaaaactc acgttaaggg attttggtca tgagattatc aaaaaggatc ttcacctaga    6120
tccttttaaa ttaaaaatga agttttaaat caatctaaag tatatatgag taaacttggt    6180
ctgacagtta ccaatgctta atcagtgagg cacctatctc agcgatctgt ctatttcgtt    6240
catccatagt tgcctgactc cccgtcgtgt agataactac gatacgggag gcttaccat     6300 ctggccccag tgctgcaatg ataccgcgag acccacgctc accggctcca gatttatcag    6360
caataaacca gccagccgga agggccgagc gcagaagtgg tcctgcaact ttatccgcct    6420
ccatccagtc tattaattgt tgccgggaag ctagagtaag tagttcgcca gttaatagtt    6480
tgcgcaacgt tgttgccatt gctacaggca tcgtggtgtc acgctcgtcg tttggtatgg    6540
cttcattcag ctccggttcc caacgatcaa ggcgagttac atgatccccc atgttgtgca    6600
aaaaagcggt tagctccttc ggtcctccga tcgttgtcag aagtaagttg gccgcagtgt    6660
```

```
tatcactcat ggttatggca gcactgcata attctcttac tgtcatgcca tccgtaagat    6720
gcttttctgt gactggtgag tactcaacca agtcattctg agaatagtgt atgcggcgac    6780
cgagttgctc ttgcccggcg tcaatacggg ataataccgc gccacatagc agaactttaa    6840
aagtgctcat cattggaaaa cgttcttcgg ggcgaaaact ctcaaggatc ttaccgctgt    6900
tgagatccag ttcgatgtaa cccactcgtg cacccaactg atcttcagca tcttttactt    6960
tcaccagcgt ttctgggtga gcaaaaacag gaaggcaaaa tgccgcaaaa aagggaataa    7020
gggcgacacg gaaatgttga atactcatac tcttcctttt tcaatattat tgaagcattt    7080
atcagggtta ttgtctcatg agcggataca tatttgaatg tatttagaaa aataaacaaa    7140
taggggttcc gcgcacattt ccccgaaaag tgccacctgg gaaattgtaa acgttaatat    7200
tttgttaaaa ttcgcgttaa attttttgtta aatcagctca ttttttaacc aataggccga    7260
aatcggcaaa atcccttata atcaaaaga atagaccgag ataggqttga gtgttgttcc    7320 agtttggaac aagagtccac tattaaagaa cgtggactcc aacgtcaaag ggcgaaaaac    7380
cgtctatcag ggcgatggcc cactacgtga accatcaccc taatcaagtt ttttggggtc    7440
gaggtgccgt aaagcactaa atcggaaccc taaagggagc ccccgattta gagcttgacg    7500
gggaaagccg gcgaacgtgg cgagaaagga agggaagaaa gcgaaggag cgggcgctag    7560 ggcgctggca agtgtagcgg tcacgctgcg cgtaaccacc acacccgccg cgcttaatgc    7620
gccgctacag ggcgcgtccc attcgccatt caggctgcgc aactgttggg aagggcgat    7679
```

<210> SEQ ID NO 29
<211> LENGTH: 7679
<212> TYPE: DNA
<213> ORGANISM: Artificial Sequence
<220> FEATURE:
<223> OTHER INFORMATION: Plasmid encoding the Heavy Chain of a melanin Humanized Antibody (8C3-HE-VH3B-hIgG1)

<400> SEQUENCE: 29

```
cggtgcgggc ctcttcgcta ttacgccagc tggcgaaagg gggatgtgct gcaaggcgat      60
taagttgggt aacgccaggg ttttcccagt cacgacgttg taaaacgacg gccagtgagc     120
gcgcgtaata cgactcacta tagggcgaat tgggtaccgg gccccccctc gaggtcgacg     180
gtatcgataa gcttgatatc gaattcgctg gctgagacc cgcagaggaa gacgctctag     240
ggatttgtcc cggactagcg agatggcaag gctgaggacg ggaggctgat tgagaggcga     300
aggtacaccc taatctcaat acaacccttg gagctaagcc agcaatggta gagggaagat     360
tctgcacgtc ccttccaggc ggcctccccg tcaccaccca cccaaccccg ccccgaccgg     420
agctgagagt aattcataca aaaggactcg cccctgcctt ggggaatccc agggaccgtc     480
gttaaactcc cactaacgta gaaccagag atcgctgcgt tcccgccccc tcacccgccc     540
gctctcgtca tcactgaggt ggagaagagc atgcgtgagg ctccggtgcc cgtcagtggg     600
cagagcgcac atcgcccaca gtccccgaga agttgggggg aggggtcggc aattgaaccg     660
gtgcctagag aaggtggcgc ggggtaaact gggaaagtga tgtcgtgtac tggctccgcc     720
tttttcccga gggtggggga gaaccgtata taagtgcagt agtcgccgtg aacgttcttt     780
ttcgcaacgg gtttgccgcc agaacacagg taagtgccgt gtgtggttcc cgcgggcctg     840
gcctctttac gggttatggc ccttgcgtgc cttgaattac ttccacgccc ctggctgcag     900
tacgtgattc ttgatcccga gcttcgggtt gaaagtgggt gggagagttc gaggccttgc     960
gcttaaggag ccccttcgcc tcgtgcttga gttgaggcct ggcttgggcg ctggggccgc    1020
```

-continued

```
cgcgtgcgaa tctggtggca ccttcgcgcc tatctcgctg ctttcgataa gtctctagcc    1080
atttaaaatt tttgatgacc tgctgcgacg ctttttttct ggcaagatag tcttgtaaat    1140
gcgggccaag atctgcacac tggtatttcg gttttggggg ccgcgggcgg cgacggggcc    1200
cgtgcgtccc agcgcacatg ttcggcgagg cggggcctgc gagcgcggcc accgagaatc    1260 ggacggggt agtctcaagc tggccggcct gctctggtgc ctggcctcgc gccgccgtgt    1320
atcgccccgc cctgggcggc aaggctggcc cggtcggcac cagttgcgtg agcggaaaga    1380
tggccgcttc ccggccctgc tgcagggagc tcaaaatgga ggacgcggcg ctcgggagag    1440
cgggcgggtg agtcacccac acaaaggaaa agggcctttc cgtcctcagc cgtcgcttca    1500
tgtgactcca cggagtaccg ggcgccgtcc aggcacctcg attagttctc gagcttttgg    1560
agtacgtcgt ctttaggttg gggggagggg ttttatgcga tggagtttcc ccacactgag    1620
tgggtggaga ctgaagttag gccagcttgg cacttgatgt aattctcctt ggaatttgcc    1680
ctttttgagt ttggatcttg gttcattctc aagcctcaga cagtggttca aagttttttc    1740
cttccatttc aggtgtcgtg aaaactaccc ctaaaagcca aatctagagc caccatggac    1800
atgcgcgtgc cggcacaact gctgggcctg ctgctgcttt ggctgcgggg agctagatgc    1860
gaagtgcagc tcgtggaatc cggaggagga ctggtgcagc ctggcggaag catgcgcgtg    1920
tcatgcgcgg cttccggatt caccttctcg gacgcctgga tggattgggt cagacaagcg    1980
cccggcaaag gctggaatg gtggccgag attcggtcca aggcccataa ccacgccacc    2040
tactacgccg actccgtgaa ggggcgcttt actatctccc gggataactc gaagaatacc    2100
gtgtacctcc agatgaactc attgagggcc gaggacactg ggtctacta ctgtacccgc    2160 ggaggctact acgggaacta tggtttcttc gcctactggg gccagggtac cctcgtgact    2220
gtcagcagcg ccagcaccaa gggccccagc gtgttccac tggcccaag ctccaagtca    2280 acctccggcg gaactgctgc gctgggctgc ttggtgaagg actacttccc cgaaccggtc    2340
accgtgtcct ggaacagcgg agccctgacc tcgggagtcc acactttccc cgctgtgctg    2400
cagtcgtccg gcctgtactc gctctcgtcc gtggtcactg tcccgtcctc gtccctgggt    2460
actcagacct acatttgcaa cgtcaaccac aagccttcaa acacgaaagt ggacaagaag    2520
gtcgagccga agtcctgcga caaaacccat acttgccctc cttgtccggc tcccgaactg    2580
ctgggcggac cttccgtgtt cctcttcccg cctaagccga agacaccct gatgatcagc    2640 aggactccgg aagtgacatg cgtggtggtg gacgtgtcgc acgaggaccc ggaggtcaag    2700
tttaattggt acgtggacgg agtggaagtc cacaacgcca agaccaagcc acggaagaa    2760 cagtacaatt ccacctatcg cgtggtgtcc gtgcttaccg tgcttcacca agactggctg    2820
aacggaaagg agtacaagtg caaagtgtca aacaaagccc tgcctgcccc aatcgaaaag    2880
accatcagca aggccaaggg gcagcctcgg gaaccccaag tgtacactct cccgccgtca    2940
agagatgaac tgaccaagaa ccaagtgtcc ctcacttgtc tcgtgaaggg attctacccc    3000
tccgatatcg ccgtggagtg ggaatccaac gggcaacccg agaacaacta caagaccacc    3060
cctccggtgc ttgattccga tggctccttc ttcctctact ccaagctgac cgtggacaag    3120
tcaagatggc agcagggga cgtgttctcc tgctccgtca tgcacgaggc cctgcacaac    3180
cattacaccc agaagtctct gtcgctgagc ccgggaaaat aatgaggatc ccctattct    3240 atagtgtcac ctaaatgcta gagctcgctg atcagcctcg actgtgcctt ctagttgcca    3300
gccatctgtt gtttgcccct ccccgtgcc ttccttgacc ctggaaggtg ccactcccac    3360
tgtccttccc taataaaatg aggaaattgc atcgcattgt ctgagtaggt gtcattctat    3420
```

```
tctgggggt ggggtggggc aggacagcaa gggggaggat tgggaagaca atagcaggca   3480
tgctggggat gcggtgggct ctatggcttc tgaggcggaa agaaccagct ggggctcgag   3540
cggccgcaga ttgtaccttc tgaggcggaa agaaccagct gtggaatgtg tgtcagttag   3600
ggtgtggaaa gtccccaggc tccccagcag gcagaagtat gcaaagcatg catctcaatt   3660
agtcagcaac caggtgtgga aagtccccag gctccccagc aggcagaagt atgcaaagca   3720
tgcatctcaa ttagtcagca accatagtcc cgccccTaac tccgcccatc ccgcccctaa   3780
ctccgcccag ttccgcccat tctccgcccc atggctgact aatttttttt atttatgcag   3840
aggccgaggc cgcctcggcc tctgagctat tccagaagta gtgaggaggc ttttttggag   3900
gcctaggctt ttgcaaaaag cttaccatga ttgaacaaga tggattgcac gcaggttctc   3960
cggccgcttg ggtggagagg ctattcggct atgactgggc acaacagaca atcggctgct   4020
ctgatgccgc cgtgttccgg ctgtcagcgc aggggcgccc ggttcttttt gtcaagaccg   4080
acctgtccgg tgccctgaat gaactgcagg acgaggcagc gcggctatcg tggctggcca   4140
cgacgggcgt tccttgcgca gctgtgctcg acgttgtcac tgaagcggga agggactggc   4200
tgctattggg cgaagtgccg gggcaggatc tcctgtcatc tcaccttgct cctgccgaga   4260
aagtatccat catggctgat gcaatgcggc ggctgcatac gcttgatccg gctacctgcc   4320
cattcgacca ccaagcgaaa catcgcatcg agcgagcacg tactcggatg aagccggtc   4380 ttgtcgatca ggatgatctg gacgaagagc atcaggggct cgcgccagcc gaactgttcg   4440
ccaggctcaa ggcgcgcatg cccgacggcg aggatctcgt cgtgacccat ggcgatgcct   4500
gcttgccgaa tatcatggtg gaaaatggcc gcttttctgg attcatcgac tgtggccggc   4560
tgggtgtggc ggaccgctat caggacatag cgttggctac ccgtgatatt gctgaagagc   4620
ttggcggcga atgggctgac cgcttcctcg tgctttacgg tatcgccgct cccgattcgc   4680
agcgcatcgc cttctatcgc cttcttgacg agttcttctg agggatcgcg gagatccaga   4740
catgataaga tacattgatg agtttggaca aaccacaact agaatgcagt gaaaaaaatg   4800
ctttatttgt gaaatttgtg atgctattgc tttatttgta accattataa gctgcaataa   4860
acaagttaac aacaacaatt gcattcattt tatgtttcag gttcagggg aggtgtggga   4920 ggttttttaa gcaagtaaaa cctctacaa atgtggtatg gctgattatg agctccagct   4980
tttgttccct ttagtgaggg ttaattgcgc gcttggcgta atcatggtca tagctgtttc   5040
ctgtgtgaaa ttgttatccg ctcacaattc cacacaacat acgagccgga agcataaagt   5100
gtaaagcctg ggGtgcctaa tgagtgagct aactcacatt aattgcgttg cgctcactgc   5160
ccgctttcca gtcgggaaac ctgtcgtgcc agctgcatta atgaatcggc caacgcgcgg   5220
ggagaggcgg tttgcgtatt gggcgctctt ccgcttcctc gctcactgac tcgctgcgct   5280
cggtcgttcg gctgcggcga gcggtatcag ctcactcaaa ggcggtaata cggttatcca   5340
cagaatcagg ggataacgca ggaaagaaca tgtgagcaaa aggccagcaa aaggccagga   5400
accgtaaaaa ggccgcgttg ctggcgtttt tccataggct ccgccccct gacgagcatc   5460 acaaaaatcg acgctcaagt cagaggtggc gaaacccgac aggactataa agataccagg   5520
cgtttccccc tggaagctcc ctcgtgcgct ctcctgttcc gaccctgccg cttaccggat   5580
acctgtccgc ctttctccct tcgggaagcg tggcgctttc tcatagctca cgctgtaggt   5640
atctcagttc ggtgtaggtc gttcgctcca agctgggctg tgtgcacgaa ccccccgttc   5700
agcccgaccg ctgcgcctta tccggtaact atcgtcttga gtccaacccg gtaagacacg   5760
```

| | |
|---|---|
| acttatcgcc actggcagca gccactggta acaggattag cagagcgagg tatgtaggcg | 5820 |
| gtgctacaga gttcttgaag tggtggccta actacggcta cactagaagg acagtatttg | 5880 |
| gtatctgcgc tctgctgaag ccagttacct tcggaaaaag agttggtagc tcttgatccg | 5940 |
| gcaaacaaac caccgctggt agcggtggtt ttttgtttg caagcagcag attacgcgca | 6000 |
| gaaaaaaagg atctcaagaa gatcctttga tcttttctac ggggtctgac gctcagtgga | 6060 |
| acgaaaactc acgttaaggg attttggtca tgagattatc aaaaggatc ttcacctaga | 6120 |
| tccttttaaa ttaaaaatga gttttaaat caatctaaag tatatatgag taaacttggt | 6180 |
| ctgacagtta ccaatgctta atcagtgagg cacctatctc agcgatctgt ctatttcgtt | 6240 |
| catccatagt tgcctgactc cccgtcgtgt agataactac gatacgggag ggcttaccat | 6300 |
| ctggccccag tgctgcaatg ataccgcgag acccacgctc accggctcca gatttatcag | 6360 |
| caataaacca gccagccgga agggccgagc gcagaagtgg tcctgcaact ttatccgcct | 6420 |
| ccatccagtc tattaattgt tgccgggaag ctagagtaag tagttcgcca gttaatagtt | 6480 |
| tgcgcaacgt tgttgccatt gctacaggca tcgtggtgtc acgctcgtcg tttggtatgg | 6540 |
| cttcattcag ctccggttcc caacgatcaa ggcgagttac atgatccccc atgttgtgca | 6600 |
| aaaaagcggt tagctccttc ggtcctccga tcgttgtcag aagtaagttg gccgcagtgt | 6660 |
| tatcactcat ggttatggca gcactgcata attctcttac tgtcatgcca tccgtaagat | 6720 |
| gcttttctgt gactggtgag tactcaacca agtcattctg agaatagtgt atgcggcgac | 6780 |
| cgagttgctc ttgcccggcg tcaatacggg ataataccgc gccacatagc agaactttaa | 6840 |
| aagtgctcat cattggaaaa cgttcttcgg ggcgaaaact ctcaaggatc ttaccgctgt | 6900 |
| tgagatccag ttcgatgtaa cccactcgtg cacccaactg atcttcagca tcttttactt | 6960 |
| tcaccagcgt ttctgggtga gcaaaaacag gaaggcaaaa tgccgcaaaa aagggaataa | 7020 |
| gggcgacacg gaaatgttga atactcatac tcttcctttt tcaatattat tgaagcattt | 7080 |
| atcagggtta ttgtctcatg agcggataca tatttgaatg tatttagaaa aataaacaaa | 7140 |
| taggggttcc gcgcacattt ccccgaaaag tgccacctgg gaattgtaa acgttaatat | 7200 |
| tttgttaaaa ttcgcgttaa attttttgtta aatcagctca tttttttaacc aataggccga | 7260 |
| aatcggcaaa atcccttata aatcaaaaga atagaccgag atagggttga gtgttgttcc | 7320 |
| agtttggaac aagagtccac tattaaagaa cgtggactcc aacgtcaaag ggcgaaaaac | 7380 |
| cgtctatcag ggcgatggcc cactacgtga accatcaccc taatcaagtt ttttggggtc | 7440 |
| gaggtgccgt aaagcactaa atcggaaccc taaagggagc ccccgattta gagcttgacg | 7500 |
| gggaaagccg gcgaacgtgg cgagaaagga agggaagaaa gcgaaaggag cgggcgctag | 7560 |
| ggcgctggca agtgtagcgg tcacgctgcg cgtaaccacc acaccgccg cgcttaatgc | 7620 |
| gccgctacag ggcgcgtccc attcgccatt caggctgcgc aactgttggg aagggcgat | 7679 |

<210> SEQ ID NO 30
<211> LENGTH: 475
<212> TYPE: PRT
<213> ORGANISM: Artificial Sequence
<220> FEATURE:
<223> OTHER INFORMATION: 8C3-hIgG1 Chimera heavy chain

<400> SEQUENCE: 30

Met Asp Met Arg Val Pro Ala Gln Leu Leu Gly Leu Leu Leu Leu Trp
1               5                   10                  15

Leu Arg Gly Ala Arg Cys Glu Val Gln Leu Glu Glu Ser Gly Gly Gly
            20                  25                  30

```
Leu Val Gln Pro Gly Gly Ser Met Lys Val Ser Cys Ala Ala Ser Gly
            35                  40                  45

Phe Thr Phe Ser Asp Ala Trp Met Asp Trp Val Arg Gln Ser Pro Glu
    50                  55                  60

Lys Gly Leu Glu Trp Val Ala Glu Ile Arg Ser Lys Ala His Asn His
65                  70                  75                  80

Ala Thr Tyr Tyr Ala Glu Ser Val Lys Gly Arg Phe Thr Ile Ser Arg
                85                  90                  95

Asp Asp Ser Lys Ser Ser Val Tyr Leu Gln Met Asn Ser Leu Arg Ala
                100                 105                 110

Glu Asp Thr Gly Thr Tyr Tyr Cys Thr Arg Gly Gly Tyr Tyr Gly Asn
                115                 120                 125

Tyr Gly Phe Phe Ala Tyr Trp Gly Gln Gly Thr Leu Val Thr Val Ser
            130                 135                 140

Ala Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
            210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
            435                 440                 445
```

-continued

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 31
<211> LENGTH: 475
<212> TYPE: PRT
<213> ORGANISM: Artificial Sequence
<220> FEATURE:
<223> OTHER INFORMATION: 8C3-HE-VH3A-hIgG1 heavy chain

<400> SEQUENCE: 31

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Gln Pro Gly Gly Ser Met Arg Val Ser Cys Ala Ala Ser Gly
            35                  40                  45

Phe Thr Phe Ser Asp Ala Trp Met Asp Trp Val Arg Gln Ala Pro Gly
        50                  55                  60

Lys Gly Leu Glu Trp Val Ala Glu Ile Arg Ser Lys Ala His Asn His
65                  70                  75                  80

Ala Thr Tyr Tyr Ala Glu Ser Val Lys Gly Arg Phe Thr Ile Ser Arg
                85                  90                  95

Asp Asp Ser Lys Ser Thr Val Tyr Leu Gln Met Asn Ser Leu Arg Ala
            100                 105                 110

Glu Asp Thr Gly Thr Tyr Tyr Cys Thr Arg Gly Gly Tyr Tyr Gly Asn
        115                 120                 125

Tyr Gly Phe Phe Ala Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 32
<211> LENGTH: 475
<212> TYPE: PRT
<213> ORGANISM: Artificial Sequence
<220> FEATURE:
<223> OTHER INFORMATION: 8C3-HE-VH3B-hIgG1 heavy chain

<400> SEQUENCE: 32

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Met Arg Val Ser Cys Ala Ala Ser Gly
        35                  40                  45

Phe Thr Phe Ser Asp Ala Trp Met Asp Trp Val Arg Gln Ala Pro Gly
    50                  55                  60

Lys Gly Leu Glu Trp Val Ala Glu Ile Arg Ser Lys Ala His Asn His
65                  70                  75                  80

Ala Thr Tyr Tyr Ala Asp Ser Val Lys Gly Arg Phe Thr Ile Ser Arg
                85                  90                  95

Asp Asn Ser Lys Asn Thr Val Tyr Leu Gln Met Asn Ser Leu Arg Ala
            100                 105                 110

Glu Asp Thr Gly Val Tyr Tyr Cys Thr Arg Gly Gly Tyr Tyr Gly Asn
        115                 120                 125

Tyr Gly Phe Phe Ala Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

```
Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 33
<211> LENGTH: 475
<212> TYPE: PRT
<213> ORGANISM: Artificial Sequence
<220> FEATURE:
<223> OTHER INFORMATION: Heavy Chain Alignment Consensus

<400> SEQUENCE: 33

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Met Arg Val Ser Cys Ala Ala Ser Gly
        35                  40                  45

Phe Thr Phe Ser Asp Ala Trp Met Asp Trp Val Arg Gln Ala Pro Gly
    50                  55                  60

Lys Gly Leu Glu Trp Val Ala Glu Ile Arg Ser Lys Ala His Asn His
65                  70                  75                  80

Ala Thr Tyr Tyr Ala Glu Ser Val Lys Gly Arg Phe Thr Ile Ser Arg
                85                  90                  95

Asp Asp Ser Lys Ser Thr Val Tyr Leu Gln Met Asn Ser Leu Arg Ala
            100                 105                 110
```

Glu Asp Thr Gly Thr Tyr Tyr Cys Thr Arg Gly Gly Tyr Gly Asn
            115                 120                 125

Tyr Gly Phe Phe Ala Tyr Trp Gly Gln Gly Thr Leu Val Thr Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 34
<211> LENGTH: 240
<212> TYPE: PRT
<213> ORGANISM: Artificial Sequence
<220> FEATURE:
<223> OTHER INFORMATION: 8C3-HE-VK1A-hKappa light chain

<400> SEQUENCE: 34

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Val Ser Leu Gly Asp Arg Ala Thr Ile Thr Cys Arg Ala Ser
            35                  40                  45

Glu Ser Val Asp Ser Tyr Gly Thr Ser Phe Met His Trp Tyr Gln Gln
    50                  55                  60

Lys Pro Gly Lys Pro Lys Leu Leu Ile Tyr Leu Ala Ser Asn Leu
65                  70                  75                  80

Glu Ser Gly Val Pro Ser Arg Phe Ser Gly Ser Gly Ser Arg Thr Asp
                85                  90                  95

Phe Thr Leu Thr Ile Ser Pro Val Gln Ala Glu Asp Phe Ala Thr Tyr
                100                 105                 110

Tyr Cys Gln Gln Asn Asn Glu Tyr Pro Tyr Thr Phe Gly Gln Gly Thr
            115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 35
<211> LENGTH: 240
<212> TYPE: PRT
<213> ORGANISM: Artificial Sequence
<220> FEATURE:
<223> OTHER INFORMATION: 8C3-HE-VK1B-hKappa light chain

<400> SEQUENCE: 35

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Val Ser Val Gly Asp Arg Ala Thr Ile Thr Cys Arg Ala Ser
            35                  40                  45

Glu Ser Val Asp Ser Tyr Gly Thr Ser Phe Met His Trp Tyr Gln Gln
    50                  55                  60

Lys Pro Gly Lys Pro Lys Leu Leu Ile Tyr Leu Ala Ser Asn Leu
65                  70                  75                  80

Gln Ser Gly Val Pro Ser Arg Phe Ser Gly Ser Gly Ser Arg Thr Asp
                85                  90                  95

Phe Thr Leu Thr Ile Ser Pro Val Gln Ala Glu Asp Phe Ala Thr Tyr
                100                 105                 110

Tyr Cys Gln Gln Asn Asn Glu Tyr Pro Tyr Thr Phe Gly Gln Gly Thr
            115                 120                 125
```

Lys Leu Glu Ile Lys Arg Thr Val Ala Ala Pro Ser Val Phe Ile Phe
            130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 36
<211> LENGTH: 240
<212> TYPE: PRT
<213> ORGANISM: Artificial Sequence
<220> FEATURE:
<223> OTHER INFORMATION: 8C3-HE-VK4-hKappa light chain

<400> SEQUENCE: 36

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Asp Ser
            20                  25                  30

Leu Ala Val Ser Leu Gly Glu Arg Ala Thr Ile Asn Cys Lys Ala Ser
        35                  40                  45

Glu Ser Val Asp Ser Tyr Gly Thr Ser Phe Met His Trp Tyr Gln Gln
50                  55                  60

Lys Pro Gly Gln Pro Pro Lys Leu Leu Ile Tyr Leu Ala Ser Asn Arg
65                  70                  75                  80

Glu Ser Gly Val Pro Asp Arg Phe Ser Gly Ser Gly Ser Arg Thr Asp
                85                  90                  95

Phe Thr Leu Thr Ile Ser Pro Val Gln Ala Glu Asp Val Ala Thr Tyr
            100                 105                 110

Tyr Cys Gln Gln Asn Asn Glu Tyr Pro Tyr Thr Phe Gly Gln Gly Thr
        115                 120                 125

Lys Leu Glu Ile Lys Arg Thr Val Ala Ala Pro Ser Val Phe Ile Phe
            130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 37
<211> LENGTH: 240

```
<212> TYPE: PRT
<213> ORGANISM: Artificial Sequence
<220> FEATURE:
<223> OTHER INFORMATION: 8C3-hKappa Chimera light chain

<400> SEQUENCE: 37

Met Asp Met Arg Val Pro Ala Gln Leu Leu Gly Leu Leu Leu Leu Trp
1               5                   10                  15

Leu Arg Gly Ala Arg Cys Asp Ile Leu Met Thr Gln Ser Pro Ala Ser
                20                  25                  30

Leu Ala Val Ser Leu Gly Gln Arg Ala Thr Ile Ser Cys Arg Ala Ser
            35                  40                  45

Glu Ser Val Asp Ser Tyr Gly Thr Ser Phe Met His Trp Tyr Gln Gln
    50                  55                  60

Lys Pro Gly Gln Pro Pro Lys Leu Leu Ile Tyr Leu Ala Ser Asn Leu
65                  70                  75                  80

Glu Ser Gly Val Pro Ala Arg Phe Ser Gly Ser Gly Ser Arg Thr Asp
                85                  90                  95

Phe Thr Leu Thr Ile Asp Pro Val Glu Ala Asp Ala Ala Thr Tyr
            100                 105                 110

Tyr Cys Gln Gln Asn Asn Glu Tyr Pro Tyr Thr Phe Gly Gly Gly Thr
            115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 38
<211> LENGTH: 240
<212> TYPE: PRT
<213> ORGANISM: Artificial Sequence
<220> FEATURE:
<223> OTHER INFORMATION: Light Chain Alignment Consensus

<400> SEQUENCE: 38

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ala Val Ser Leu Gly Asp Arg Ala Thr Ile Thr Cys Arg Ala Ser
            35                  40                  45

Glu Ser Val Asp Ser Tyr Gly Thr Ser Phe Met His Trp Tyr Gln Gln
    50                  55                  60

Lys Pro Gly Gln Pro Pro Lys Leu Leu Ile Tyr Leu Ala Ser Asn Leu
65                  70                  75                  80

Glu Ser Gly Val Pro Ser Arg Phe Ser Gly Ser Gly Ser Arg Thr Asp
                85                  90                  95
```

```
Phe Thr Leu Thr Ile Ser Pro Val Gln Ala Glu Asp Phe Ala Thr Tyr
            100                 105                 110

Tyr Cys Gln Gln Asn Asn Glu Tyr Pro Tyr Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```